(12) United States Patent
Zadno-Azizi

(10) Patent No.: US 6,986,778 B2
(45) Date of Patent: Jan. 17, 2006

(54) EXCHANGE METHOD FOR EMBOLI CONTAINMENT

(75) Inventor: Gholam-Reza Zadno-Azizi, Newark, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 801 days.

(21) Appl. No.: 09/768,031

(22) Filed: Jan. 23, 2001

(65) Prior Publication Data

US 2002/0065507 A1 May 30, 2002

Related U.S. Application Data

(63) Continuation of application No. 09/049,712, filed on Mar. 27, 1998, now Pat. No. 6,544,276, which is a continuation-in-part of application No. 09/026,106, filed on Feb. 19, 1998, now Pat. No. 6,312,407, which is a continuation-in-part of application No. 08/975,723, filed on Nov. 20, 1997, now Pat. No. 6,050,972, which is a continuation-in-part of application No. 08/812,139, filed on Mar. 6, 1997, now abandoned, which is a continuation-in-part of application No. 08/650,464, filed on May 20, 1996, now abandoned.

(51) Int. Cl.
*A61M 29/00* (2006.01)

(52) U.S. Cl. .................... 606/200; 606/194; 604/96.01; 604/107

(58) Field of Classification Search ...... 604/96.01–109, 604/528, 19, 35; 606/1, 108, 151, 159, 167, 606/180, 190–200, 170, 171; 600/434, 585
See application file for complete search history.

(56) References Cited

U.S. PATENT DOCUMENTS

| | | |
|---|---|---|
| 3,087,492 A | 4/1963 | Garth |
| 3,211,150 A | 10/1965 | Foderick |
| 4,517,979 A | 5/1985 | Pecenka |
| 4,540,404 A | 9/1985 | Wolvek |
| 4,573,966 A | 3/1986 | Weikl et al. |
| 4,602,633 A | 7/1986 | Goodfriend et al. |
| 4,610,662 A | 9/1986 | Weitel et al. |

(Continued)

FOREIGN PATENT DOCUMENTS

| | | |
|---|---|---|
| EP | 0 380 873 A2 | 8/1990 |
| EP | 0 638 327 A1 | 2/1995 |
| WO | WO 92/13589 | 8/1992 |
| WO | WO 96/01591 | 1/1996 |
| WO | WO 97/27896 | 8/1997 |
| WO | WO 97/44082 | 11/1997 |
| WO | WO 97/44084 | 11/1997 |
| WO | WO 97/44085 | 11/1997 |
| WO | WO 98/33443 | 8/1998 |
| WO | WO 98/38930 | 9/1998 |
| WO | WO 99/44542 | 9/1999 |

*Primary Examiner*—Glenn K. Dawson
(74) *Attorney, Agent, or Firm*—Knobbe Martens Olson & Bear LLP

(57) ABSTRACT

The present invention provides a method for exchanging catheters while containing emboli within a blood vessel such as a saphenous vein graft, coronary artery, carotid artery, or other similar vessels. A guidewire is inserted through the vasculature of a patient until it reaches a desired treatment site. A therapy catheter is then inserted over the guidewire until the distal end of the therapy catheter reaches the treatment site. The guidewire has a distally mounted balloon which is inflated to occlude the blood vessel. Then, the therapy catheter provides means for treating the vessel at the treatment site. After treatment, the therapy catheter is removed from the guidewire and exchanged with an aspiration catheter which rides over the guidewire until the distal end of the aspiration catheter reaches the treatment site. The aspiration catheter applies negative pressure to remove any emboli formed by the treatment procedure.

15 Claims, 37 Drawing Sheets

U.S. PATENT DOCUMENTS

| | | |
|---|---|---|
| 4,655,746 A | 4/1987 | Daniels et al. |
| 4,748,982 A | 6/1988 | Horzewski et al. |
| 4,781,677 A | 11/1988 | Wilcox |
| 4,794,928 A | 1/1989 | Kletschka |
| 4,808,153 A | 2/1989 | Parisi |
| 4,827,941 A | 5/1989 | Taylor et al. |
| 4,842,579 A | 6/1989 | Shiber |
| 4,846,193 A | 7/1989 | Tremulis et al. |
| 4,867,742 A | 9/1989 | Calderon |
| 4,884,573 A | 12/1989 | Wijay et al. |
| 4,911,163 A | 3/1990 | Fina |
| 4,926,858 A | 5/1990 | Gifford et al. |
| 4,932,413 A | 6/1990 | Shockey et al. |
| 4,944,740 A | 7/1990 | Buchbinder et al. |
| 4,947,864 A | 8/1990 | Shockey et al. |
| 4,955,385 A | 9/1990 | Kvalo et al. |
| 4,976,689 A | 12/1990 | Buchbinder et al. |
| 5,011,469 A | 4/1991 | Buckberg et al. |
| 5,011,488 A | 4/1991 | Ginsburg |
| 5,024,651 A | 6/1991 | Shiber |
| 5,035,686 A | 7/1991 | Crittenden et al. |
| 5,040,548 A | 8/1991 | Yock |
| 5,064,416 A | 11/1991 | Newgard et al. |
| 5,071,407 A | 12/1991 | Termin et al. |
| 5,090,958 A | 2/1992 | Sahota |
| 5,092,839 A | 3/1992 | Kipperman |
| 5,100,388 A | 3/1992 | Behl et al. |
| 5,160,321 A | 11/1992 | Sahota |
| 5,163,911 A | 11/1992 | Sirimanne et al. ..... 604/164.13 |
| 5,167,239 A | 12/1992 | Cohen et al. ............... 600/585 |
| 5,171,221 A | 12/1992 | Samson |
| 5,234,002 A | 8/1993 | Chan |
| 5,234,407 A | 8/1993 | Teirstein et al. |
| 5,250,060 A | 10/1993 | Carbo et al. |
| 5,256,145 A | 10/1993 | Atkinson et al. |
| 5,263,932 A | 11/1993 | Jang |
| RE34,466 E | 12/1993 | Taylor et al. |
| 5,267,958 A | 12/1993 | Buchbinder et al. |
| 5,273,527 A | 12/1993 | Schatz et al. |
| 5,279,546 A | 1/1994 | Mische et al. |
| RE34,633 E | 6/1994 | Sos et al. |
| 5,318,527 A | 6/1994 | Hyde et al. |
| 5,320,604 A | 6/1994 | Walker et al. |
| 5,320,605 A | 6/1994 | Sahota |
| 5,324,259 A | 6/1994 | Taylor et al. |
| 5,350,397 A | 9/1994 | Palermo et al. |
| 5,358,472 A | 10/1994 | Vance et al. |
| 5,364,376 A | 11/1994 | Horzewski et al. |
| 5,368,567 A | 11/1994 | Lee |
| 5,395,335 A | 3/1995 | Jang |
| 5,413,557 A | 5/1995 | Solar et al. |
| 5,415,636 A | 5/1995 | Forman |
| 5,423,742 A | 6/1995 | Theron |
| 5,425,709 A | 6/1995 | Gambale |
| 5,449,343 A | 9/1995 | Samson et al. |
| 5,454,788 A | 10/1995 | Walker et al. |
| 5,456,667 A | 10/1995 | Ham et al. |
| 5,462,529 A | 10/1995 | Simpson et al. |
| 5,478,309 A | 12/1995 | Sweezer et al. |
| 5,484,412 A | 1/1996 | Pierpont |
| 5,490,837 A | 2/1996 | Blaeser et al. |
| 5,496,346 A | 3/1996 | Horzewski et al. |
| 5,505,699 A | 4/1996 | Forman et al. |
| 5,516,336 A | 5/1996 | McInnes et al. |
| 5,520,645 A | 5/1996 | Imran et al. |
| 5,536,252 A | 7/1996 | Imran et al. |
| 5,569,215 A | 10/1996 | Crocker |
| 5,571,169 A | 11/1996 | Plaia et al. |
| 5,607,466 A | 3/1997 | Imbert et al. |
| 5,609,574 A | 3/1997 | Kaplan et al. |
| 5,613,949 A | 3/1997 | Miraki |
| 5,634,894 A | 6/1997 | Magram |
| 5,639,274 A | 6/1997 | Fischell et al. |
| 5,645,533 A | 7/1997 | Blaeser et al. |
| 5,658,262 A | 8/1997 | Castaneda et al. |
| 5,667,521 A | 9/1997 | Keown |
| 5,681,336 A | 10/1997 | Clement et al. ............ 606/159 |
| 5,690,613 A | 11/1997 | Verbeek |
| 5,693,015 A | 12/1997 | Walker et al. |
| 5,695,468 A | 12/1997 | Lafontaine et al. |
| 5,695,519 A | 12/1997 | Summers et al. |
| 5,728,123 A | 3/1998 | Lemelson et al. |
| 5,779,688 A | 7/1998 | Imran et al. |
| 5,807,330 A | 9/1998 | Teitelbaum |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran ........................ 604/509 |
| 5,849,016 A | 12/1998 | Suhr |
| 5,868,705 A | 2/1999 | Bagaoisan et al. |
| 5,876,367 A | 3/1999 | Kaganov et al. |
| 5,879,361 A | 3/1999 | Nash |
| 5,906,606 A | 5/1999 | Chee et al. |
| 5,908,405 A | 6/1999 | Imran et al. |
| 5,925,016 A | 7/1999 | Chornenky et al. |
| 6,001,118 A | 12/1999 | Daniel et al. |
| 6,013,085 A | 1/2000 | Howard |
| 6,022,336 A | 2/2000 | Zadno-Azizi et al. |
| 6,042,598 A | 3/2000 | Tsugita et al. |
| 6,050,972 A | 4/2000 | Zadno-Azizi et al. .... 604/97.01 |
| 6,053,932 A | 4/2000 | Daniel et al. |
| 6,059,814 A | 5/2000 | Ladd |
| 6,066,149 A | 5/2000 | Samson et al. |
| 6,068,623 A | 5/2000 | Zadno-Azizi et al. |
| 6,074,357 A | 6/2000 | Kaganov et al. |
| 6,080,170 A | 6/2000 | Nash et al. |
| 6,090,083 A | 7/2000 | Sell et al. |
| 6,126,635 A | 10/2000 | Simpson et al. |
| 6,129,739 A | 10/2000 | Khosravi |
| 6,135,991 A | 10/2000 | Muni et al. ................. 604/509 |
| 6,152,909 A | 11/2000 | Bagaoisan et al. |
| 6,159,195 A | 12/2000 | Ha et al. |
| 6,165,200 A | 12/2000 | Tsugita et al. |
| 6,176,844 B1 | 1/2001 | Lee |
| 6,251,084 B1 | 6/2001 | Coelho ....................... 600/585 |

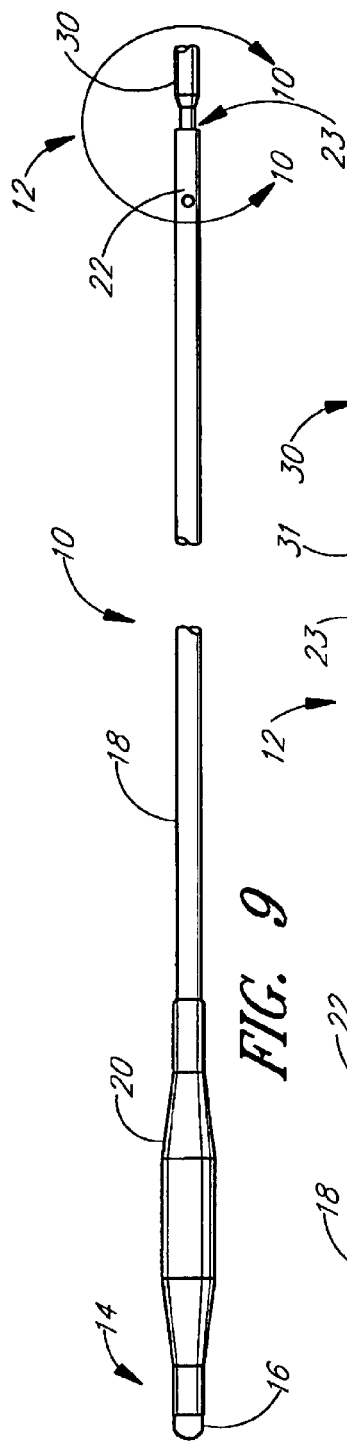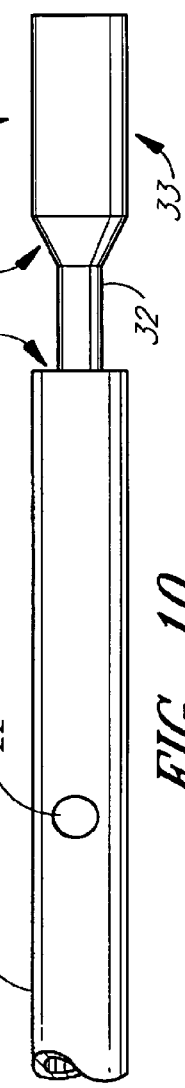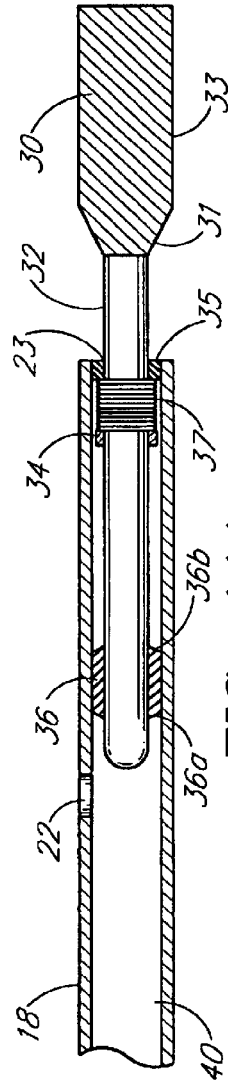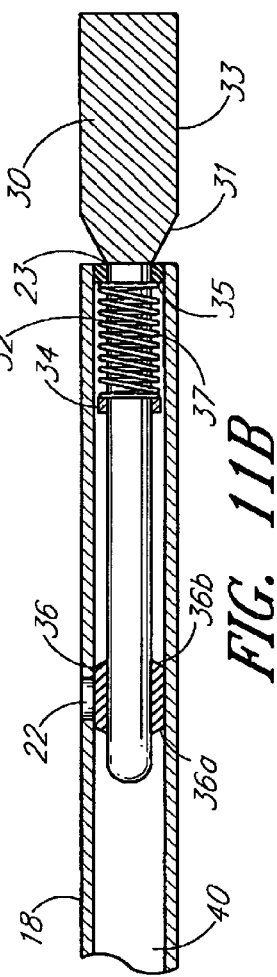
FIG. 9
FIG. 10
FIG. 11A
FIG. 11B

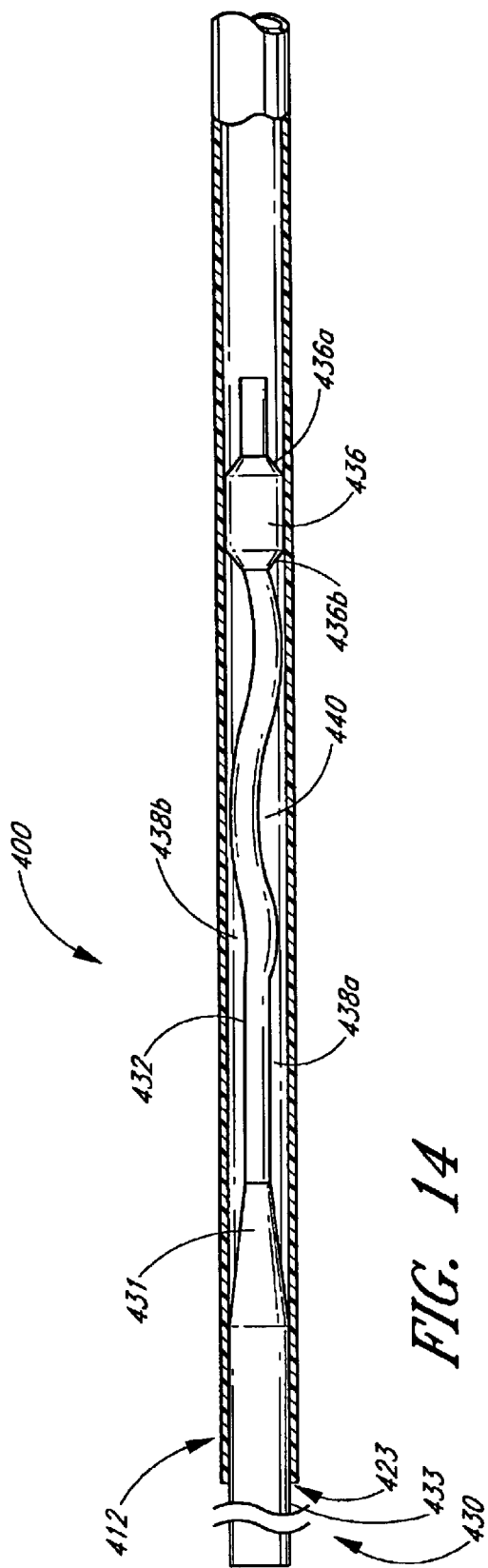
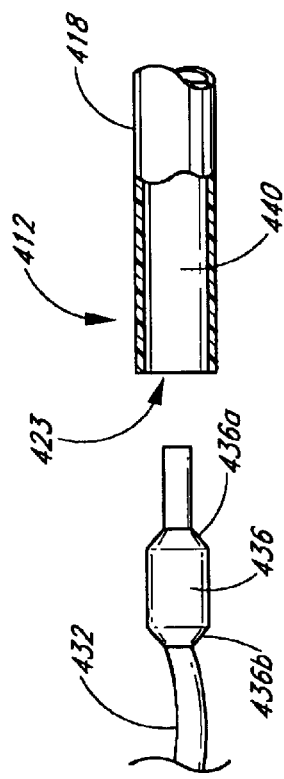
FIG. 14
FIG. 15

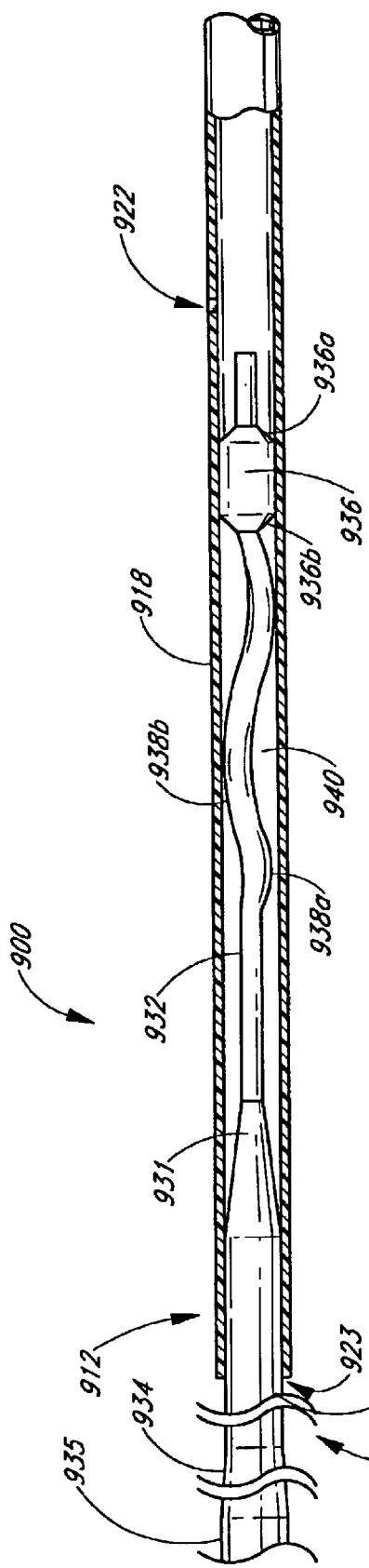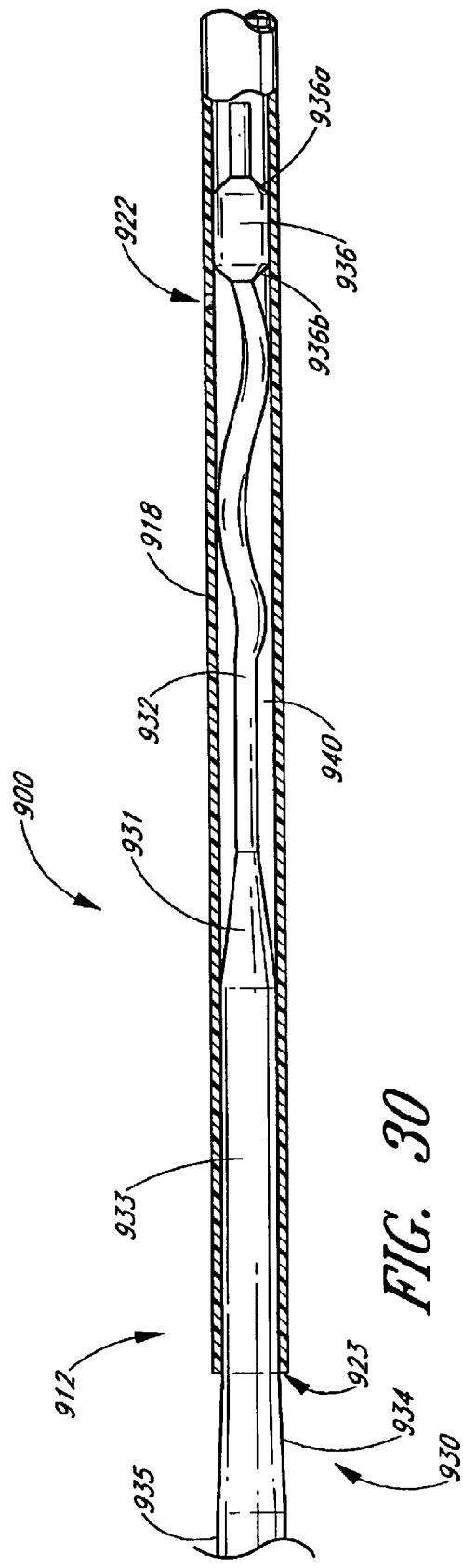

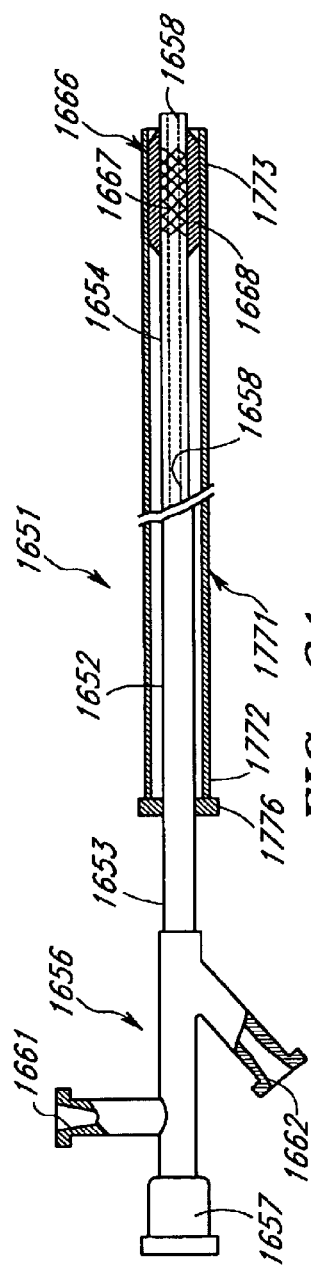
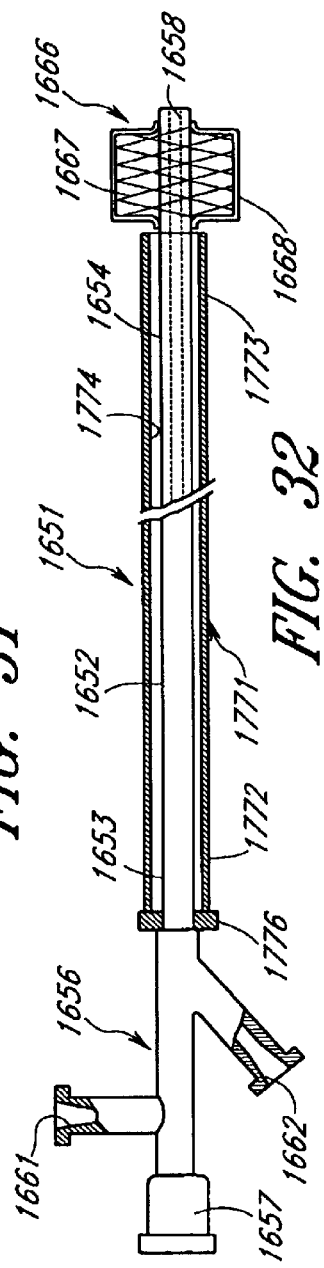
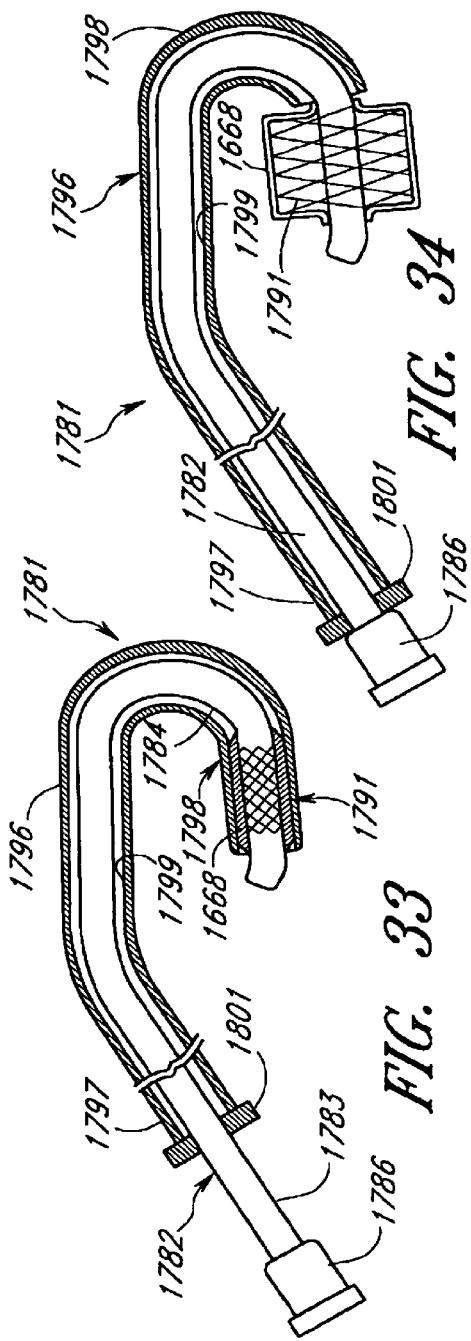

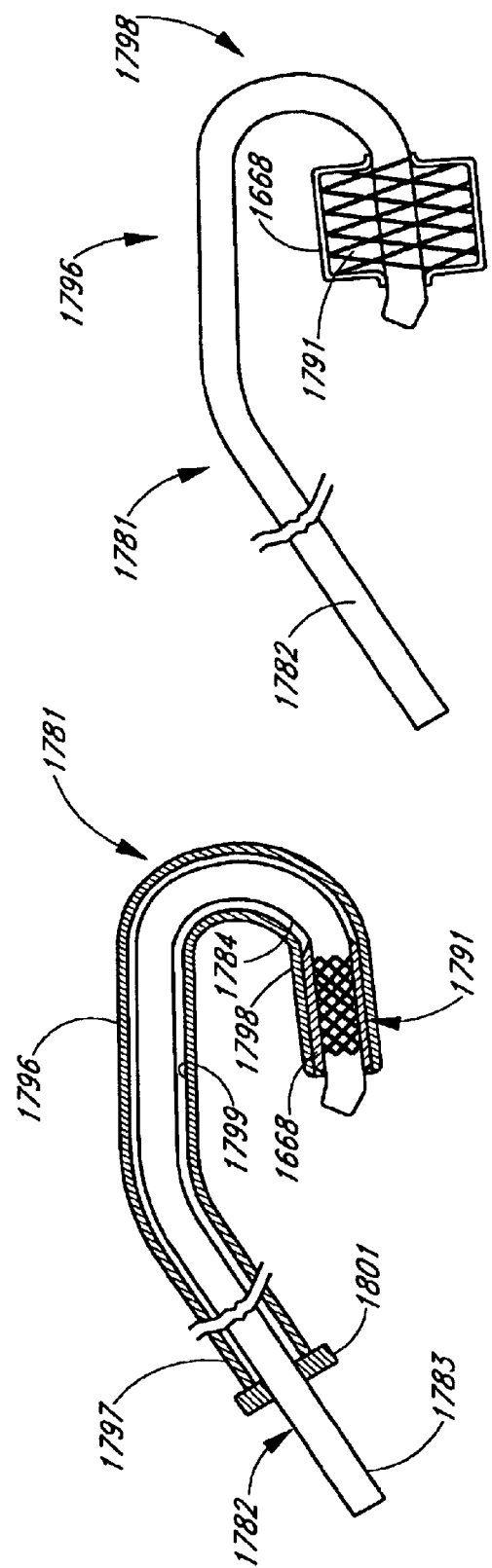

EXCHANGE METHOD FOR EMBOLI CONTAINMENT

RELATED APPLICATIONS

This application is a continuation of application Ser. No. 09/049,712, entitled EXCHANGE METHOD FOR EMBOLI CONTAINMENT, filed Mar. 27, 1998, now U.S. Pat. No. 6,544,276, which is a continuation-in-part of application Ser. No. 08/975,723 entitled LOW PROFILE CATHETER VALVE AND INFLATION ADAPTER, filed Nov. 20, 1997, now U.S. Pat. No. 6,050,972, the entirety of which is hereby incorporated by reference. U.S. Pat. No. 6,050,972 is a continuation-in-part of application Ser. No. 08/812,139, filed Mar. 6, 1997, abandoned, which is a continuation-in-part of application Ser. No. 08/650,464, filed May 20, 1996, abandoned. Application Ser. No. 09/049,712, is also a continuation-in-part of application Ser. No. 09/026,106, entitled OCCLUSION OF A VESSEL, filed Feb. 19, 1998, now U.S. Pat. No. 6,312,407, which is also a continuation-in-part of application Ser. No. 08/650,464, filed May 20, 1996, abandoned.

BACKGROUND OF THE INVENTION

1. Field of the Invention

The present invention relates to medical catheters used in treating saphenous vein grafts, coronary arteries, and other blood vessels, and more particularly, to a method for exchanging catheters during emboli containment in such vessels.

2. Description of the Related Art

Guidewires are conventionally used to guide the insertion of various medical instruments, such as catheters, to a desired treatment location within a patient's vasculature. In a typical procedure, the clinician forms an access point for the guidewire by creating an opening in a peripheral blood vessel, such as the femoral artery. The highly flexible guidewire is then introduced through the opening into the peripheral blood vessel, and is then advanced by the clinician through the patient's blood vessels until the guidewire extends across the vessel segment to be treated. Various treatment catheters, such as a balloon dilatation catheter for a percutaneous transluminal coronary angioplasty, may then be inserted over the guidewire and similarly advanced through vasculature until they reach the treatment site.

In certain treatment procedures, it is desirable to successively introduce and then remove a number of different treatment catheters over a guidewire that has been placed in a particular location. In other words, one treatment catheter is "exchanged" for another over a single guidewire. Such an exchange typically involves withdrawing the treatment catheter over the guidewire until the treatment catheter is fully removed from the patient and the portion of the guidewire which extends from the patient. The guidewire is then available to act as a guide for a different treatment catheter.

As can be readily appreciated, the withdrawal of treatment catheters over a placed guidewire may result in the guidewire being displaced from its position. To overcome this difficulty, the prior art has developed "anchorable" guidewires, which generally feature some structure on their distal ends to releasably secure the guidewire at a particular location in the patient for the duration of the medical procedure. One such anchorable guidewire is disclosed in U.S. Pat. No. 5,167,239 to Cohen et al., which discloses a hollow guidewire with an inflation lumen and an expandable balloon on its end. The Cohen device includes a removable inflation manifold, and a check valve to maintain the balloon in the inflated state when the manifold is removed. The check valve apparatus used by the Cohen device is relatively bulky, and is described as having an outer diameter in its preferred embodiment of 0.0355 inches. Consequently, any treatment catheter intended to be inserted over the Cohen device must have an interior guidewire lumen larger than the outer diameter of the Cohen valve, which for the preferred embodiment, requires an interior lumen with a diameter of more than 0.0355 inches. Cohen also does not address the problem of emboli containment.

As is readily appreciated by those of skill in the art, increasing the interior lumen size of a treatment catheter results in an increase in the outer diameter of the treatment catheter. However, many blood vessels where it is desirable to apply catheter treatment are quite narrow. For example, the left coronary arteries are blood vessels having diameters ranging from 2 to 4 mm, and are susceptible to plaque. Similarly, saphenous vein grafts (SVG) and the carotid arteries are also quite small and susceptible to plaque, and could not practically be treated by larger diameter devices.

Human blood vessels often become occluded or completely blocked by plaque, thrombi, other deposits, emboli or other substances, which reduce the blood carrying capacity of the vessel. Should the blockage occur at a critical place in the circulatory system, serious and permanent injury, or even death, can occur. To prevent this, some form of medical intervention is usually performed when significant occlusion is detected.

Coronary heart disease is an extremely common disorder in developed countries, and is the leading cause of death in the U.S. Damage to or malfunction of the heart is caused by narrowing or blockage of the coronary arteries (atherosclerosis) that supply blood to the heart. The coronary arteries are first narrowed and may eventually be completely blocked by plaque, and may further be complicated by the formation of thrombi (blood clots) on the roughened surfaces of the plaques. Myocardial infarction can result from atherosclerosis, especially from an occlusive or near occlusive thrombi overlying or adjacent to the atherosclerotic plaque, leading to death of portions of the heart muscle. Thrombi and emboli also often result from myocardial infarction, and these clots can block the coronary arteries, or can migrate further downstream, causing additional complications.

Various types of intervention techniques have been developed which facilitate the reduction or removal of the blockage in the blood vessel, allowing increased blood flow through the vessel. One technique for treating stenosis or occlusion of a blood vessel is balloon angioplasty. A balloon catheter is inserted into the narrowed or blocked area, and the balloon is inflated to expand the constricted area. In many cases, near normal blood flow is restored. It can be difficult, however, to treat plaque deposits and thrombi in the coronary arteries, because the coronary arteries are small, which makes accessing them with commonly used catheters difficult.

Other types of intervention include atherectomy, deployment of stents, introduction of specific medication by infusion, and bypass surgery. Each of these methods are not without the risk of embolism caused by the dislodgement of the blocking material which then moves downstream. In addition, the size of the blocked vessel may limit percutaneous access to the vessel.

In coronary bypass surgery, a more costly and invasive form of intervention, a section of a vein, usually the saphenous vein taken from the leg, is used to form a connection between the aorta and the coronary artery distal to the obstruction. Over time, however, the saphenous vein graft may itself become diseased, stenosed, or occluded, similar to the bypassed vessel. Atherosclerotic plaque in saphenous vein grafts tends to be more friable and less fibrocalcific than its counterpart in native coronary arteries.

Diffusely diseased old saphenous vein grafts with friable atherosclerotic lesions and thrombi have therefore been associated with iatrogenic distal embolic debris. Balloon dilatation of saphenous vein grafts is more likely to produce symptomatic embolization than dilatation of the coronary arteries, not only because of the difference in the plaque but also because vein grafts and their atheromatous plaques are generally larger than the coronary arteries to which they are anastomosed. Once the plaque and thrombi are dislodged from the vein, they can move downstream, completely blocking another portion of the coronary artery and causing myocardial infarction. In fact, coronary embolization as a complication of balloon angioplasty of saphenous vein grafts is higher than that in balloon angioplasty of native coronary arteries. Therefore, balloon angioplasty of vein grafts is performed with the realization that involvement by friable atherosclerosis is likely and that atheroembolization represents a significant risk.

Because of these complications and high recurrence rates, old diffusely diseased saphenous vein grafts have been considered contraindications for angioplasty and atherectomy, severely limiting the options for minimally invasive treatment. However, some diffusely diseased or occluded saphenous vein grafts may be associated with acute ischemic syndromes, necessitating some form of intervention.

Furthermore, attempts heretofore have been made to treat occlusions in the carotid arteries leading to the brain. However, such arteries have been very difficult to treat because of the possibility of dislodging plaque which can enter various arterial vessels of the brain and cause permanent brain damage. Attempts to treat such occlusions with balloon angioplasty have been very limited because of such dangers. In surgical treatments, such as endarterectomy, the carotid artery is slit and plaque is removed from the vessel in the slit area. Such surgical procedures have substantial risk associated with them which can lead to morbidity and mortality.

In other procedures, such as in angioplasty and in the treatment of peripheral arteries and veins, there is the possibility that the guide wires and catheters used in such procedures during deployment of the same may cause dislodgement of debris or emboli which can flow downstream and cause serious damage, such as stroke, if they occlude blood flow in smaller vessels. Moreover, when treating aneurysms, coils or other objects deployed to fill the aneurysm may break free and become lost downstream. Thus, in summary, embolization and migration of micro-emboli downstream to an end organ is a major concern of cardiologists during catheterizations.

Accordingly, what is needed is an exchange method for use during treatment of narrow blood vessels such as the carotid arteries, coronary arteries and saphenous vein grafts. Specifically, what is needed is a method which allows an exchange of catheters while a distal occluding device is deployed to perform treatment within the vessel and to contain emboli produced, created, or used during the treatment procedure. Furthermore, because a distal occluding device may block the flow of blood to vital organs, it is desirable that the exchange be performed quickly and easily in order to minimize the time that the blood vessel is occluded.

SUMMARY OF THE INVENTION

The present invention satisfies the above needs by providing a method for exchanging catheters during an emboli containment procedure. As described herein, the term "emboli" may refer to any debris, particles, or other objects found, created or placed in a blood vessel. "Emboli containment" may refer to emboli removal, neutralization, disintegration, minimization, or simply to preventing emboli from moving downstream. In essence, "containment" refers to any procedure which reduces the deleterious effects that emboli may have on the patient. The preferred exchange method is particularly useful in angioplasty and similar procedures in smaller blood vessels such as the coronary or carotid arteries or in saphenous vein grafts. The exchange method described herein can be accomplished rapidly to minimize the time that a treated blood vessel is occluded for treatment.

For example, in most angioplasty procedures, a guidewire is first introduced into the vasculature of a patient until the distal end of the guidewire is near the occlusion or stenosis. The guidewire preferably bears a distal occlusion device, such as a balloon, filter, coil, or combination of these elements. The occlusive device is preferably activated prior to performing therapy to remove or reduce an occlusion or stenosis, to provide a working area and to prevent particles and debris produced during therapy from migrating downstream. The occlusive device may completely or partially occlude the vessel.

In order to perform an exchange over the guidewire catheter, the catheter must be made such that the occlusive device remains activated in order to minimize particles from going downstream. Furthermore, the proximal end of the guidewire must have a low profile to accommodate other catheters which are to be advanced over the guidewire. In one preferred method, a therapy catheter is advanced over a proximal end of the guidewire to the site of the plaque or lesion. After deploying the occlusive device on the end of the guidewire, therapy is performed on the lesion by the therapy device. One preferred therapy device is a dilatation catheter which compresses the lesion against the walls of the vasculature. In addition to dilatation balloon catheters, other forms of therapy may be used to dislodge, disintegrate, or neutralize the plaque. One method is to provide an ultrasonic catheter which targets the plaque and destroys it using shock waves. Another method is to use a vibration delivery catheter, which causes the plaque to break up due to a vibrating wire. Another method uses a drug delivery catheter provided over the guidewire, which provides fluids to dissolve the plaque. Other types of therapy include radiation therapy.

After treatment of the plaque by an appropriate therapy method, emboli often remain in the working area. The therapy catheter can then be removed and exchanged with an emboli removal catheter, such as an aspiration catheter for aspirating the emboli from the working area. The aspiration catheter can then be exchanged with another therapy catheter, such as a catheter bearing a stent which is deployed onto the lesion for maintaining the opening of the blood vessel.

The present invention in a preferred embodiment allows for the rapid and easy exchange of catheters by deploying the occlusive device in stages. For instance, when a guidewire with a distal occlusion balloon is used, the balloon is inflated only when there is danger of emboli moving downstream. Thus, if treatment of the stenosis consists of a dilatation procedure and deployment of a stent, the occlusion balloon will be inflated for a first inflation period during which the dilatation balloon works on the plaque, the dilatation catheter is exchanged with an aspiration catheter, and the aspiration catheter removes emboli from the vessel. After aspiration, the occlusion balloon can safely be deflated to allow blood flow for a period to organs downstream. An exchange can then be performed with another therapy catheter, such as a stent deploying catheter, and the occlusion balloon is reinflated for a second inflation period to deploy a stent to the location of the stenosis. By employing an exchange method with vessel occlusion occurring in stages, the time that blood flow is occluded in the vessel decreases, thereby minimizing the risks to the patient and presenting significant advantages over known technology. The speed of exchange is also improved by using an adaptor which allows for easy and quick handling of the guidewire for inflation and deflation.

BRIEF DESCRIPTION OF THE DRAWINGS

FIG. 9 is a side view of a catheter incorporating the low profile valve in a preferred aspect of the present invention.

FIG. 10 is an enlarged view of the proximal portion of the catheter of FIG. 10 showing an exterior view of the catheter segment featuring the low profile valve in a preferred aspect of the present invention.

FIG. 11A is a longitudinal cross-sectional view of the catheter segment of FIG. 10 showing the low profile valve in the open position.

FIG. 11B is a longitudinal cross-sectional view of the catheter segment of FIG. 10 showing the low profile valve in the closed position.

FIG. 14 is a longitudinal cross-sectional view of an alternative embodiment of the low profile valve, depicting the valve in the open position FIG. 15 is a longitudinal cross-sectional view of the embodiment of FIG. 14 depicting the valve in the closed position.

FIGS. 29 and 30 are cross-sectional views of a proximal section of a catheter having an alternative embodiment of the valve in a preferred aspect of the present invention.

FIG. 31 is a side-elevational view in section of one embodiment of a catheter apparatus incorporating a preferred aspect of the present invention for treating occluded vessels.

FIG. 32 is a side-elevational view in section similar to FIG. 31 but showing the apparatus in FIG. 31 with the expansion member (in this case, a self-expandable seal) deployed.

FIG. 33 is a side-elevational view in section of another embodiment of a catheter apparatus incorporating a preferred aspect of the present invention for treating occluded vessels.

FIG. 34 is a view similar to FIG. 33 but showing the expansion member (in this case, a self-expandable seal) deployed.

FIG. 35 is a side-elevational view in section of another embodiment of a catheter apparatus incorporating a preferred aspect of the present invention for treating occluded vessels.

FIG. 36 is a view similar to FIG. 35 but showing the expansion member deployed and the sleeve completely removed.

DESCRIPTION OF THE PREFERRED EMBODIMENTS

I. Exchange Method During Emboli Containment

The method discussed herein allows for the rapid exchange of catheters during angioplasty and similar procedures. In particular, the preferred method of the present invention is adapted for use in the treatment and removal of an occlusion in a blood vessel in which the occlusion has a length and a width or thickness which at least partially occludes the vessel's lumen. Thus, the catheters of a preferred aspect of the present invention are effective in treating both partial and complete occlusions of the blood vessels. As used herein, "occlusion" includes both partial and complete occlusions, stenoses, emboli, thrombi, plaque and any other substance which at least partially occludes the vessel's lumen.

The method and apparatus of the present invention preferably can be used in any vessel of the body where the pressure is at least 0.2 psi at any stage of the heart pumping cycle, and more preferably, is about 1.2 psi, with a flow rate of at least 10 cc per minute. The method and apparatus are particularly suited for use in removal of occlusions from saphenous vein grafts, coronary and carotid arteries, and in other non-branching vessels having similar pressures and flow where a suitable working area can be created. Although the present invention will be described in connection with a saphenous vein graft, it should be understood that this application is merely exemplary, and the method can be used in other blood vessels as well. For example, it will be appreciated that the described method can also be applied to coronary arteries, carotid arteries, or any other arteries or veins where treatment and containment of emboli is desired.

A. The Preferred Treatment Method

Figure 1A:
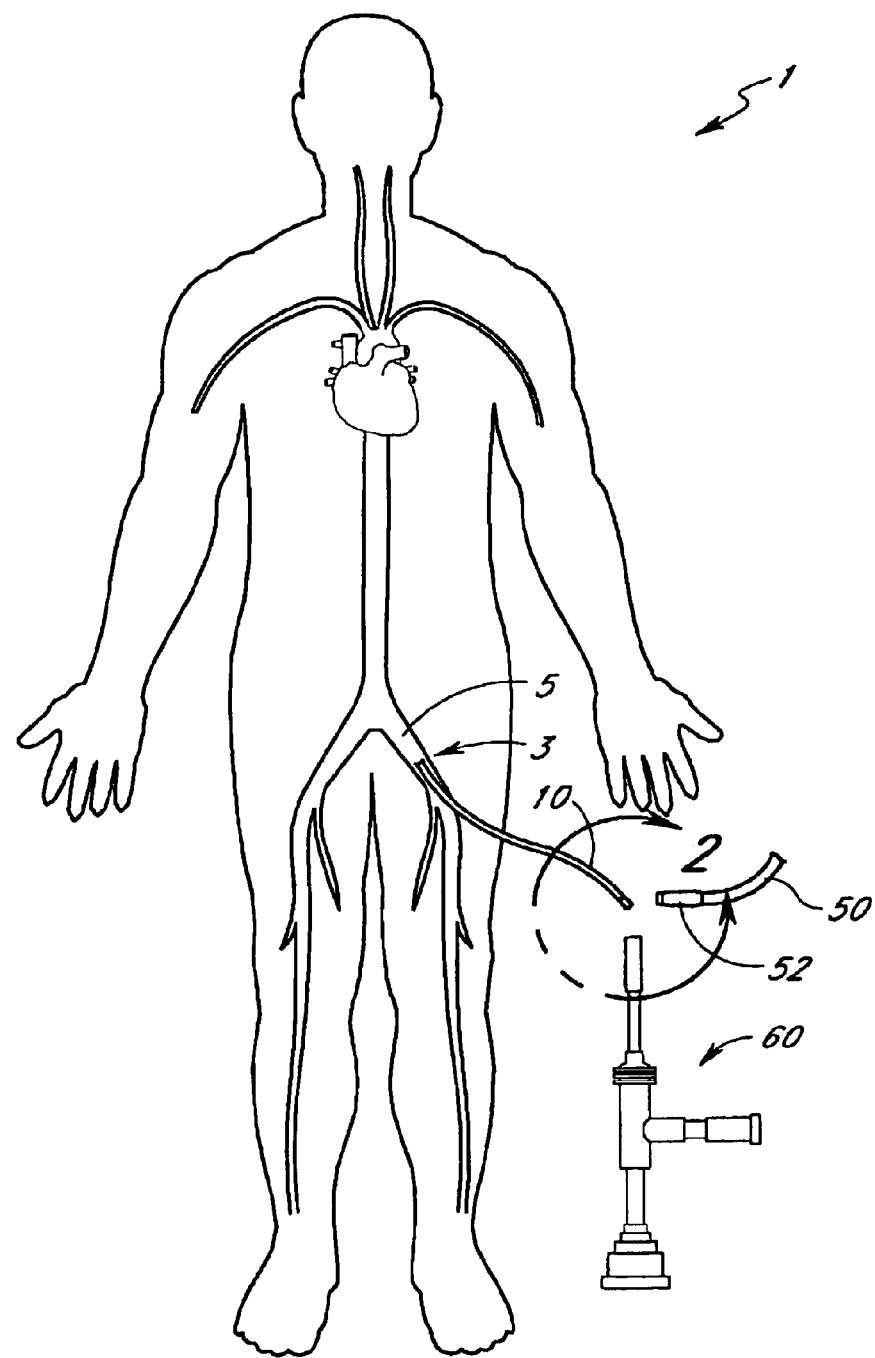
FIG. 1A is a schematic view of a patient undergoing treatment by a preferred aspect of the exchange method of the present invention.
Figure 1B:
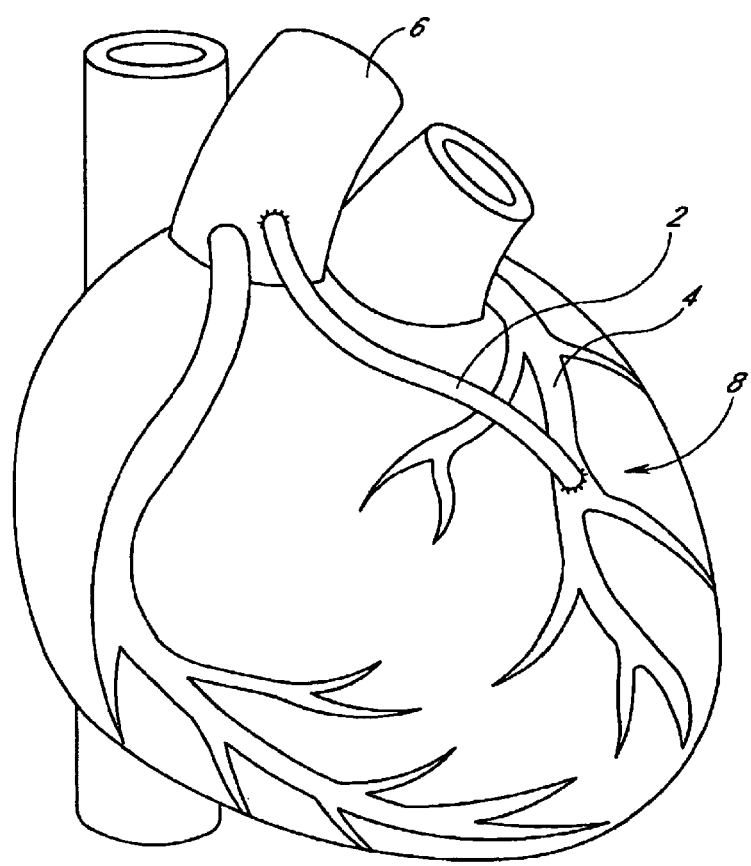
FIG. 1B is a perspective view of a human heart with a saphenous vein graft.

In one preferred aspect of the present invention, a catheter or guidewire 10 is inserted into the human body 1 through a groin insertion site 3, as shown in FIG. 1A. The guidewire 10 is passed through the femoral artery 5 and into the blood vessel network until it reaches the intended treatment site, which, as shown in FIG. 1B, is a saphenous vein graft 2. The graft 2 is used to bypass one of the occluded coronary arteries 4, and connects the aorta 6 to the coronary artery at a location distal the occlusion 8. Fluoroscopy is typically used to guide the guidewire and other devices to the desired location within the patient. The devices are frequently marked with radiopaque markings to facilitate visualization of the insertion and positioning of the devices within the patient's vasculature.

The catheter 10 used for the preferred method is shown in FIGS. 9–11B. As described in further detail below, the catheter 10 comprises a tubular body 18 having a central lumen 40 extending between a proximal end 12 and a distal end 14. An inflation port 22 is provided near the proximal end 12 of the tubular body, which allows inflation fluid to pass through central lumen 40 to a distally mounted occlusive device, such as a balloon 20. A sealing member 30 is inserted to the lumen 40 at opening 23 of the tubular body. This sealing member extends into the lumen 40 and plugs the inflation port 22 to maintain balloon inflation, as described in more detail with respect to FIGS. 11A and 11B below.

Figure 2:
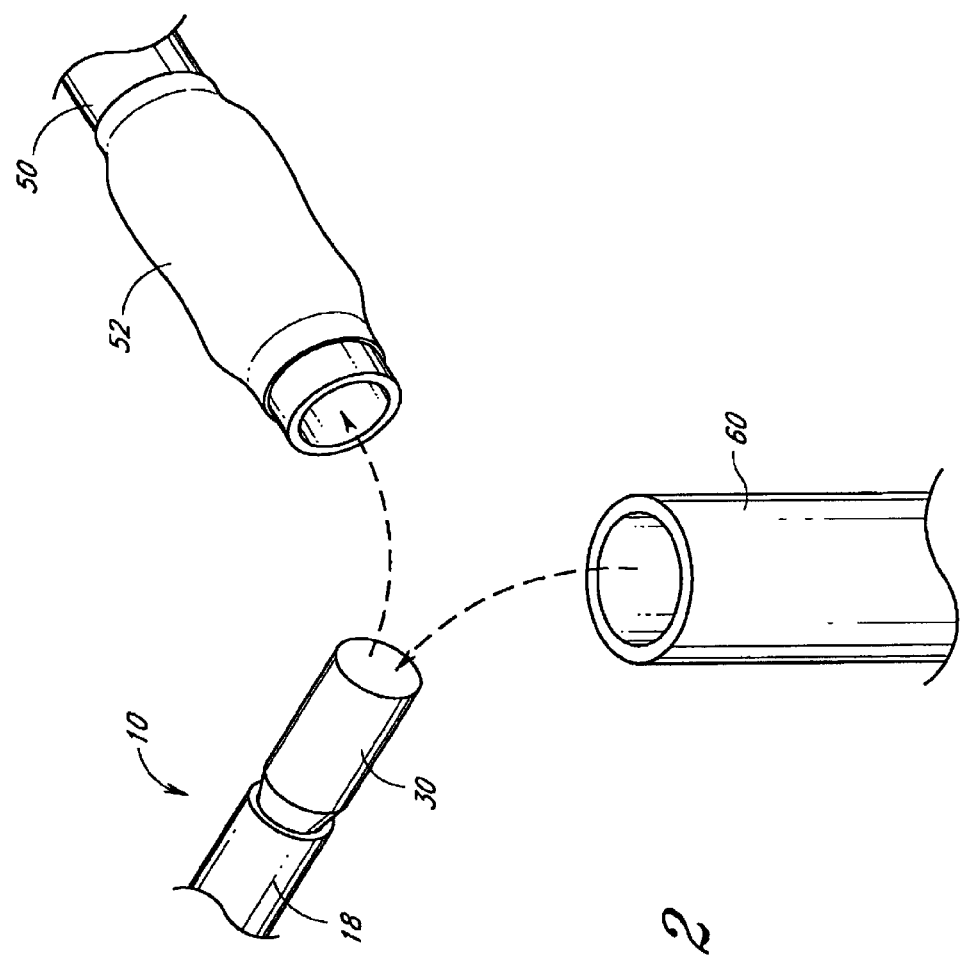
FIG. 2 is an enlarged perspective view of the proximal end of the guidewire shown in FIG. 1A, particularly showing an exchange method between a therapy catheter and an aspiration catheter.

FIG. 2 shows an enlarged view of the proximal end of the guidewire 10 with sealing member 30 inserted therein. Both the guidewire 10 and the sealing member 30 have substantially the same diameter, thereby allowing a catheter or guidewire having at least one inner lumen to pass over the two. This inner lumen can be made small to have substantially the same diameter as the outer diameter of the guidewire and sealing member. In the preferred embodiment, the outer diameter of the tubular body 18 and the sealing member 30 is about 0.014 inches. Therefore, catheters having a lumen with a diameter as small as 0.014 inches may be exchanged over the guidewire 10.

FIG. 2 also illustrates an exemplary exchange method. Where guidewire 10 carries a first treatment catheter such as a therapy catheter 50 having a dilatation balloon 52, this therapy catheter 50 can be slid off the proximal end of the guidewire 10 and sealing member 30. Then, a second treatment catheter such as an aspiration catheter 60 may be slid over the proximal ends of the sealing member 30 and the guidewire 10 toward the treatment location. Further details regarding this exchange are described below.

1. Insertion of the Guidewire

Figure 3A:
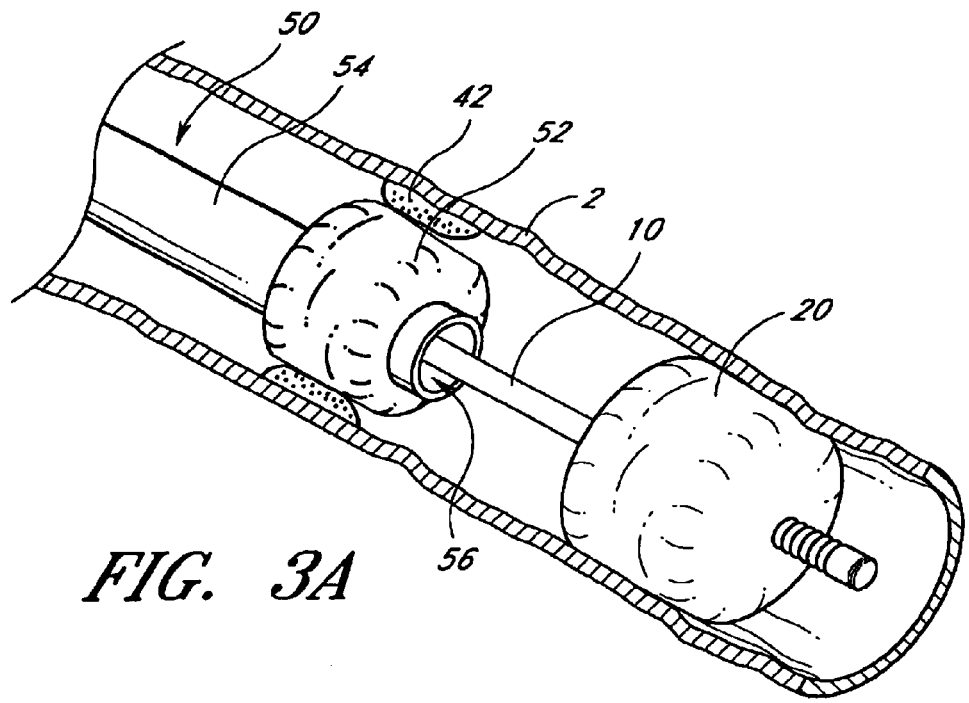
FIGS. 3A is a perspective view of an over-the-wire therapy catheter having a dilatation balloon on its distal end and guidewire inserted into a saphenous vein graft in accordance with a preferred aspect of the present invention, with the vein graft shown partially cut away.

FIGS. 3A–3D show more explicitly a preferred method of containing and aspirating embolic material while performing a balloon angioplasty and stenting therapy. FIG. 3A shows a lesion or plaque 42 on the walls of a saphenous vein graft 2. A catheter or guidewire 10 is advanced into the blood vessel to a point distal of the lesion 42. The method of a preferred aspect of the present invention can effectively be carried out using a number of guidewires or catheters that perform the function of occluding the vessel and allowing for the slidable insertion of various other catheters and devices. The term "catheter" as used herein is therefore intended to include both guidewires and catheters with these desired characteristics. As described in further detail below, the catheter has an occlusive device, such as an inflatable balloon, filter or other mechanical occlusive device, attached at its distal end. The occlusive device should be capable of preventing the migration of particles and debris from the working area, either through total or partial occlusion of the vessel. Note that the occlusion of the vessel need not be complete. Substantial occlusion of the vessel can be sufficient for purposes of the present invention.

The guidewire 10 should be sized so as to be slidable with respect to the therapy, aspiration or other catheters to be inserted over the guidewire. When the guidewire is properly positioned inside the vessel, the occlusive device at the distal end of the guidewire is actuated to occlude the vessel distal to the existing lesion to create a working area. With the occlusive device effectively blocking the flow of emboli downstream, various catheters may be exchanged over the guidewire 10 to treat the vessel without the risk of emboli flowing downstream and cutting off blood flow to vital organs.

In non-bifurcated areas of the blood vessels, it has been discovered that fluid from the proximal portion of the same vessel acts as an infusion source. One therefore need only occlude the distal portion of the vessel to create a working area surrounding the occlusion and allow blood to flow from the proximal portion of the vessel into the working area. It should be noted that, as used herein, "proximal" refers to the portion of the apparatus closest to the end which remains outside the patient's body, and "distal" refers to the portion closest to the end inserted into the patient's body. Thus, the embodiment described above only provides an occlusive device distal to the working area.

However, an embodiment is also contemplated wherein the working area is defined by occlusive devices located both proximal and distal to the lesion 42. In this embodiment, a guide catheter having a single lumen is first introduced into the patient's vasculature through an incision made in the femoral artery or vein in the groin and used to guide the insertion of other catheters and devices to the desired site. This guide catheter carries an occlusion balloon or other occlusive device to occlude the vessel proximal to the lesion 42. Following insertion of the guide catheter, a second catheter is inserted through the guide catheter and past the site of the occlusion. This second catheter serves as the exchange catheter or guidewire over which various catheters may be advanced and removed.

2. Therapy Catheter/Aspiration Catheter Exchange

As shown in FIG. 3A, once the guidewire 10 is in place, a therapy catheter may then be delivered to the site of the occlusion. The therapy catheter can employ any number of means for treatment, including a balloon catheter used to perform angioplasty, a catheter which delivers a stent, a catheter for delivering enzymes, chemicals, or drugs to dissolve or treat the occlusion, an atherectomy device, or a laser or ultrasound device used to ablate the occlusion.

The therapy catheter 50 of the preferred embodiment includes a dilatation balloon 52 located on the distal end of an elongate tubular body 54. The tubular body 54 has a lumen 56 extending from a proximal end to the distal end of the tubular body which is sized to override the guidewire 10 until the dilatation balloon 52 reaches the point of the lesion 42. Once balloon 52 is in place, the occlusion balloon 20 on guidewire 10 is inflated to at least partially block blood flow. Then, the dilatation balloon 52 is inflated to compress the plaque 42 against the walls of the blood vessel. This inflation has the effect of dislodging some plaque and creating emboli 48 (shown in FIG. 3B) in the working area.

Figure 3B:
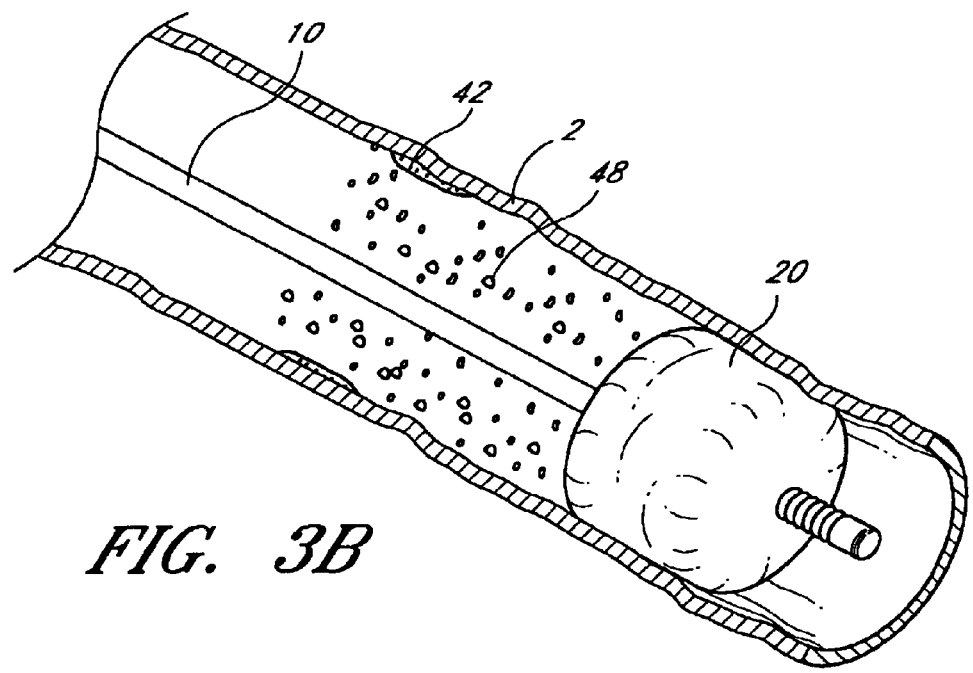
FIG. 3B is a perspective view of a guidewire inserted into a saphenous vein graft after the therapy catheter of FIG. 3A has been removed, with the vein graft shown partially cut away.
Figure 3C:
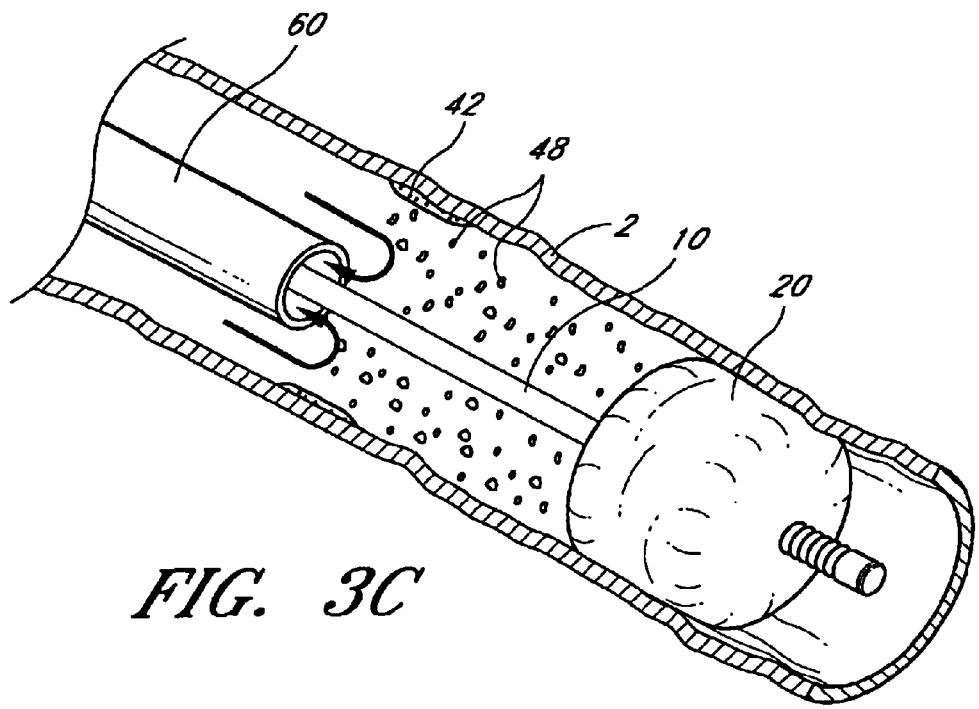
FIG. 3C is a perspective view of an over-the-wire aspiration catheter and a guidewire inserted into a saphenous vein graft after an exchange with the therapy catheter of FIG. 3A has been performed, with the vein graft shown partially cut away.

In the preferred method, after treatment by the therapy catheter 50 is completed, the therapy catheter is completely removed from the body by sliding the therapy catheter over the guidewire 10 in a proximal direction away from the lesion and out of the body, leaving only the guidewire 10 as shown in FIG. 3B. A rapid exchange is then performed and, as illustrated in FIG. 3C, an aspiration catheter 60 is deployed over the guidewire 10. The term "aspiration catheter" includes any device which creates an area of fluid turbulence and uses negative pressure and reverse flow to aspirate fluid and debris, and includes those devices which create a venturi effect within the vessel. Aspiration catheter 60 as shown in FIG. 3C is an elongate tubular body having a lumen extending from a proximal end to a distal end. It should be noted that any particles which break free during therapy and aspiration procedures will be kept at the site of the procedure within the working area by the occlusive device occluding the distal portion of the vessel in combination with the blood pressure coming from the proximal portion of the vessel. The debris is prevented from migrating elsewhere, and remains localized for removal by aspiration. Further details regarding aspiration catheters are described in assignee's pending application entitled ASPIRATION SYSTEM AND METHOD, application Ser. No. 09/026,013, filed Feb. 19, 1998, now U.S. Pat. No. 6,152,909, the entirety of which is hereby incorporated by reference. Once aspiration is completed, the balloon 20 may be deflated to resume blood flow through the vessel.

Preferably, the procedure described above is perform twice using a predilatation catheter and a dilatation catheter. The predilatation catheter is a first therapy catheter which is advanced over the proximal end of the guidewire 10 to the point of the lesion 42. The balloon on the distal end of the predilatation catheter has a first inflation diameter designed to perform a first treatment to the lesion 42. The predilatation catheter is then exchanged with an aspiration catheter to aspirate emboli formed by the first treatment, while the occlusion balloon remains inflated. After aspiration, the occlusion balloon 20 is deflated to allow blood to flow to organs downstream, and then reinflated after exchange of the aspiration catheter for the dilatation catheter. This second therapy catheter has a dilatation balloon with a larger inflation diameter than the first dilatation balloon so as to further compress the plaque 42 against the vessel walls. Once this treatment is completed, the second therapy catheter is exchanged with the aspiration catheter for removing emboli from the blood system.

Further exchanges of therapy catheters having successively larger dilatation balloons with aspiration catheters are also contemplated by the present invention, with each exchange occurring while the distal occlusion balloon is inflated. Moreover, it is not always necessary to follow treatment with a therapy catheter with an exchange for an aspiration catheter. Therapy catheters can be exchanged with other therapy catheters to perform further treatment in the blood vessel before an exchange with an aspiration catheter is made.

3. Stent Catheter Exchange

Figure 3D:
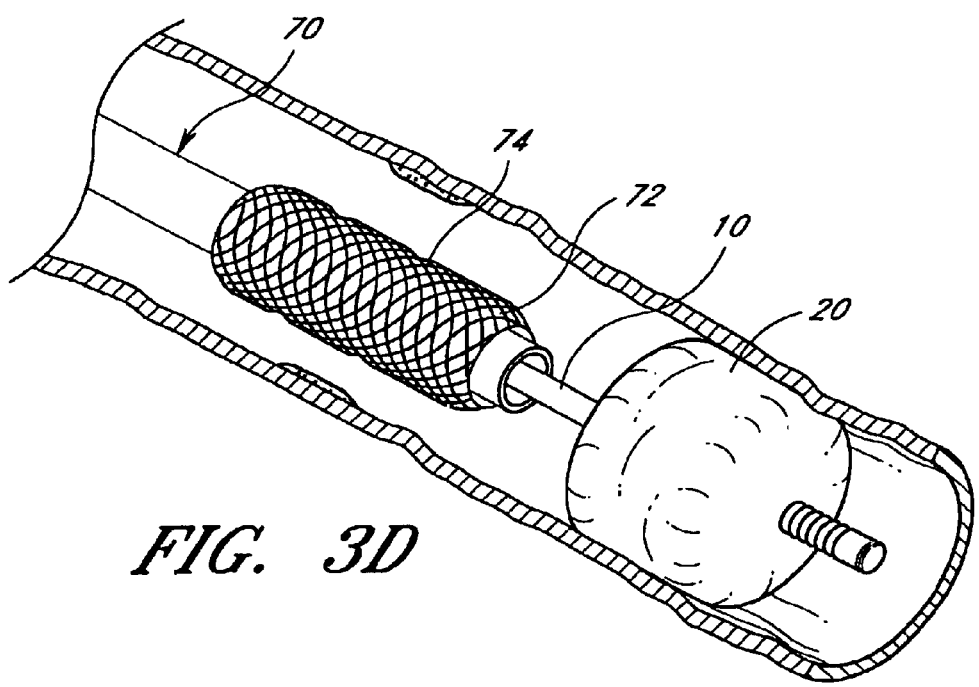
FIG. 3D is a perspective view of an over-the-wire stenting balloon and a guidewire inserted into a saphenous vein graft after an exchange with the aspiration catheter of FIG. 3C has been performed, with the vein graft shown partially cut away.

In the preferred method of the present invention, following treatment of the lesion and aspiration by one or more sequences as described above, the occlusion balloon 20 is deflated to resume blood flow to the vessel. Another catheter exchange is performed whereby the aspiration catheter is removed from the guidewire 10 and exchanged with a deployment catheter carrying a stent. As shown in FIG. 3D, the deployment device may be a catheter 70 carrying a balloon 72 holding an angioplasty stent 74. Once the catheter 70 reaches the point of lesion, the occlusion balloon 20 is reinflated to prevent any particles dislodged by the stenting process from migrating downstream. The balloon 70 is then inflated to expand the stent to its working diameter, and is sized to implant the stent into the vascular wall. Plastic deformation of the stent prevents it from collapsing once the balloon has been deflated and removed from the patient. Further details regarding stents are contained in assignee's pending application entitled STENT POSITIONING APPARATUS AND METHOD, application Ser. No. 08/744,632, filed Nov. 6, 1996, the entirety of which is hereby incorporated by reference. After the stent is in place, an exchange may be performed between the deployment catheter 70 and the aspiration catheter 60 to remove any debris formed by the stenting process. After aspiration, the occlusion balloon 20 is deflated and the aspiration catheter is removed.

B. Alternative Exchange Methods

The method described above is merely exemplary, and it should be recognized that the catheter exchange method may utilize a variety of exchanges of different types of catheters while emboli are being contained. The term "therapy catheter" is meant to include any of a number of known devices used to treat an occluded vessel. For example, a catheter carrying an inflatable balloon for use in balloon angioplasty can be delivered to dilate the occlusion. Thermal balloon angioplasty includes the use of heat to "mold" the vessel to the size and shape of the angioplasty balloon. Similarly, an intravascular stent can be delivered via a balloon catheter and deployed at the site of the occlusion to keep the vessel open. Cutting, shaving, scraping or pulverizing devices can be delivered to excise the occlusion in a procedure known as atherectomy. A laser or ultrasound device can also be delivered and used to ablate plaque in the vessel. Various thrombolytic or other types of drugs can be delivered locally in high concentrations to the site of the occlusion. It is also possible to deliver various chemical substances or enzymes via a catheter to the site of the stenosis to dissolve the obstruction. The term "therapy catheter" encompasses these and similar devices.

Figure 4:
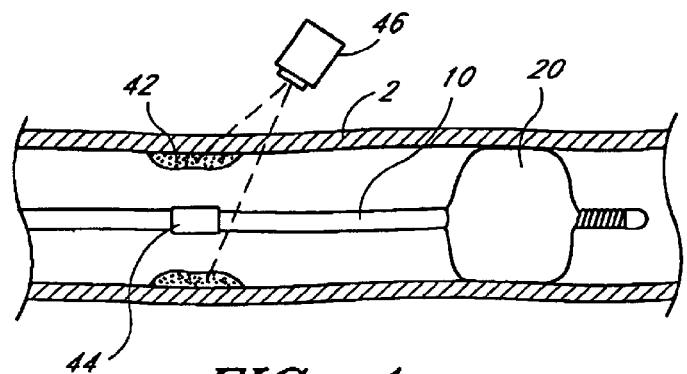
FIG. 4 is a side view of a guidewire inserted into a saphenous vein graft, the guidewire having a radiopaque marker for targeting by an external shock wave generator, with the vein graft shown partially cut away.

FIG. 4 shows an alternative embodiment employing a distal occlusion catheter for use in directing shockwaves to disintegrate the plaque 42. The catheter 10 comprises a radiopaque marker 44 located proximal to the distal balloon 20. The marker 44 is used to locate the plaque 42 for targeting by external shock wave generator 46. After inflation of the balloon, the shock wave generator 46 is focused onto the plaque 42 by use of the radiopaque marker to disintegrate the plaque.

After treatment of the plaque by the shock wave generator, an aspiration catheter 60 as described in FIG. 3C may be slid over the guidewire 10 for aspirating the emboli created by the shock wave treatment. Alternatively, the shock wave treatment may be performed with the aspiration catheter 60 already advanced over the guidewire 10. In such an embodiment, a radiopaque marker may either be placed on the guidewire or aspiration catheter itself for targeting the location of the plaque. Furthermore, the method described above may be implemented using ultrasounds for focusing of the shock wave generator to the plaque. For instance, a target balloon on a catheter may be advanced over the guidewire to the location of the lesion and inflated with air.

Air provides a medium with a significantly different acoustical impedance than body tissue. This results in good ultrasound visualization for targeting the lesion. This catheter is then exchanged with an aspiration catheter for removing emboli from the vessel. Further exchanges with a stent deployment catheter or other types of therapy catheters may be performed as described above.

Figure 5:
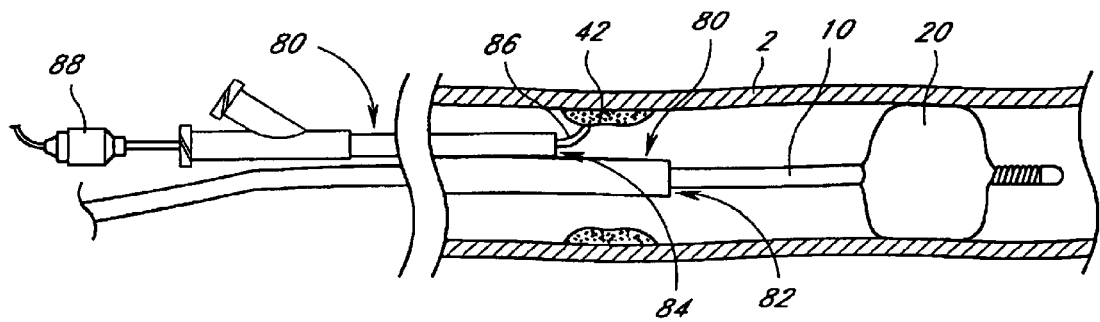
FIG. 5 is a side view of a vibration delivery catheter and a guidewire inserted into a saphenous vein graft, with the vein graft shown partially cut away.

FIG. 5 shows another alternative therapy method for treating the plaque 42. A vibration delivery catheter 80 is advanced over the guidewire 10 to a position adjacent the lesion 42. The vibration delivery catheter is preferably a monorail catheter having two lumens 82 and 84, lumen 82 serving as a passageway through which the guidewire 10 passes, and lumen 84 serving as a passageway for a waveguide or coupling member in the form of a wire 86. The guidewire lumen 82 as shown in FIG. 5 is located only on the distal end of the vibration delivery catheter. However, the lumen 82 can be made to extend the entire length of the catheter 80 if desired. One end of wire 86 contacts the lesion 42, while the other end extends out of the free end of catheter 80 outside the body of the patient and is attached to a transducer 88. With the occlusion balloon 20 inflated, by activating the transducer the wave guide 86 is caused to act on the lesion 42 with transverse and longitudinal motion of the end of the wave guide to machine away or disintegrate the lesion 42. Exchanges may be performed following this treatment with the aspiration, therapy or other catheters as described above.

Figure 6:
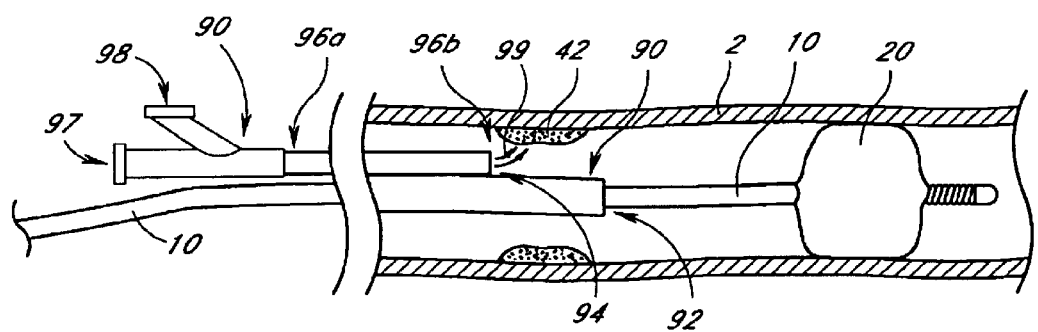
FIG. 6 is a side view of a drug delivery catheter and a guidewire inserted into a saphenous vein graft, with the vein graft shown partially cut away.

FIG. 6 shows an alternative therapy method wherein a drug delivery catheter 90 is advanced over guidewire 10 to dissolve the plaque 42. The catheter 90 is preferably a monorail catheter having two lumens 92 and 94, the lumen 92 riding over the guidewire 10. The drug delivery lumen 94 extends from a proximal end 96a to a distal end 96b, with the distal end 96b positioned adjacent the lesion to be treated. At the proximal end, an infusion port 97 is provided for delivering drugs 99 to the location of the lesion. Preferable materials for use in dissolving the lesion 42 are TPA (tissue plasminogen activator) available from Genentech, Inc., or pro-urokinase, available from Abbott Laboratories. Also at the proximal end, an aspiration port 98 is provided for removing emboli created by the procedure. Alternatively, the drug delivery catheter may be exchanged with a separate aspiration catheter for performing emboli containment. After dissolution of the lesion 42, exchanges may be made with stent carrying catheters or other catheters as described above.

Figure 7:
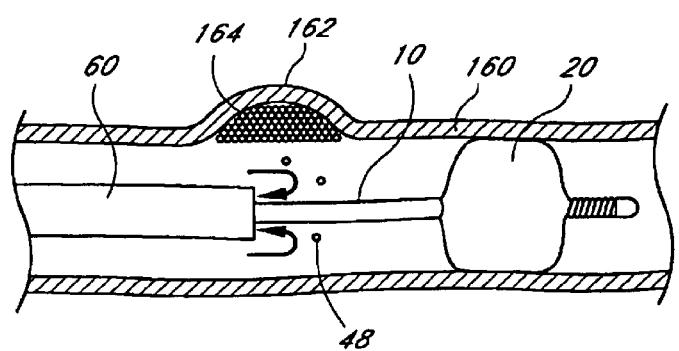
FIG. 7 is a side view of an aspiration catheter and a guidewire inserted into an artery being treated for an aneurysm, with the artery shown partially cut away.

The exchange method as described in a preferred aspect of the present invention is not applicable solely to procedures dislodging emboli. Rather, the present exchange method also applies to any situation wherein a distally occluding device prevents the migration of undesired particles downstream. For instance, as shown in FIG. 7, an aneurysm of an artery is shown, wherein a bulge 162 is found in artery 160. Guidewire 10 carrying distal occlusion balloon 20 is advanced through the vessel such that the balloon 20 is located distal to the bulge 162. The balloon 20 is inflated so that various treatment and/or aspiration catheters may be exchanged to perform treatment on the aneurysm. In treating aneurysms, one preferred method is to fill the bulge 162 with embolization elements 164. The distal occlusion balloon 20 is necessary because some of these particles may break free and migrate downstream. An exchange is also desired for treating aneurysms because deployment of particles 164 must be done sequentially, with subsequent catheters delivering more and more embolization elements to fill bulge 162. Thus, a catheter exchange over the guidewire 10 is desirable for rapidly filling the bulge 162 while the distal occlusion balloon 20 is inflated. An exchange is further desired to advance an aspiration catheter into the vessel to remove any particles that may have come loose while treating the aneurysm.

C. Exchange Methods Over Alternative Occlusive Devices

Although the embodiments described above refer to a distally occluding balloon to prevent emboli from migrating downstream, other methods for occluding the blood vessel may be used while performing the exchange method described in a preferred aspect of the present invention. With respect to all of these methods, the proximal ends of the expansion members are sized to allow an exchange of catheters over the catheter or guidewire bearing the expansion member. These methods as briefly discussed herein are described in further detail below in the section entitled "Expansion Members."

In FIGS. 35–36, a catheter apparatus is shown having a self-expanding sealing mechanism. As shown in FIG. 35, the catheter apparatus 1781 comprises a guiding catheter 1782 with a self-expanding sealing mechanism 1791 mounted on distal end 1784. The sealing mechanism 1791 is enclosed by an elongate sleeve 1796 having a collar 1801 mounted on the proximal extremity 1797 of sleeve 1796. The collar 1801 serves as a mechanism for retracting the sleeve to uncover self-expanding sealing mechanism 1791 after the catheter has been deployed to permit the self-expanding sealing mechanism 1791 to expand and form a seal with the vessel adjacent the stenosis to be treated. Sleeve 1796 may be completely removed, as shown in FIG. 36, to permit catheters with inner lumen diameters substantially the same as the outer diameter of the guiding catheter to be exchanged over the catheter. The various types of occlusive devices provided at the distal end of these catheter apparatuses and their manner of operation are more particularly described below with respect to FIGS. 31–46.

Figure 47:
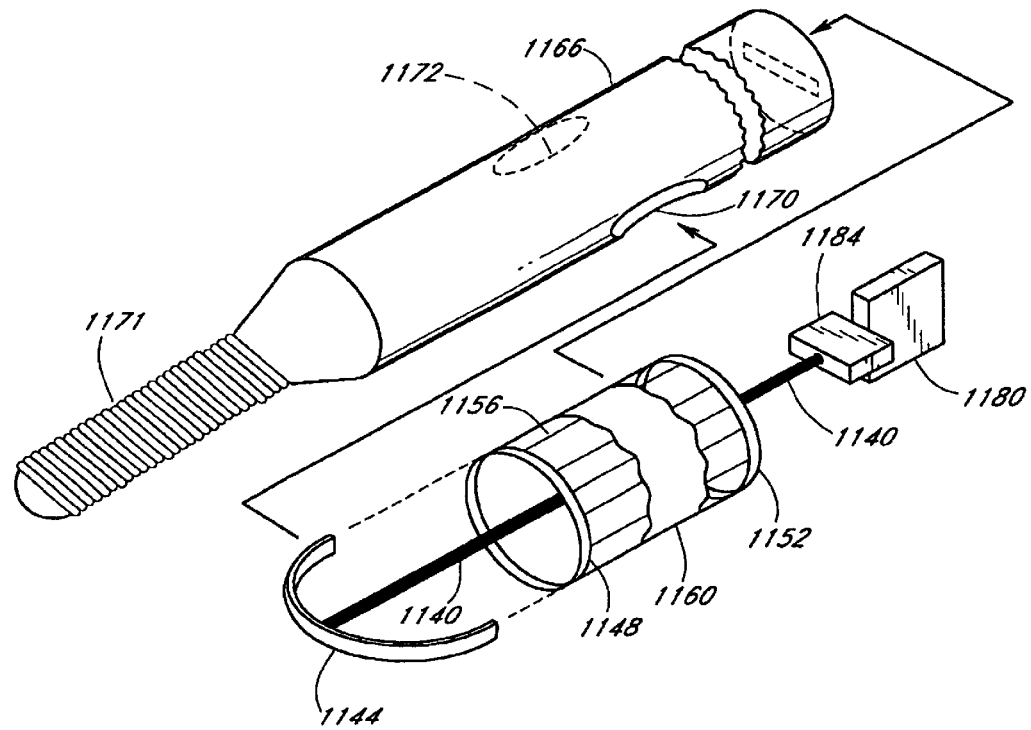
FIG. 47 is an isometric view of an embodiment of the invention in which a pull wire is used to deploy a plurality of non-self-expanding ribbons surrounded by a membrane.
Figure 48:
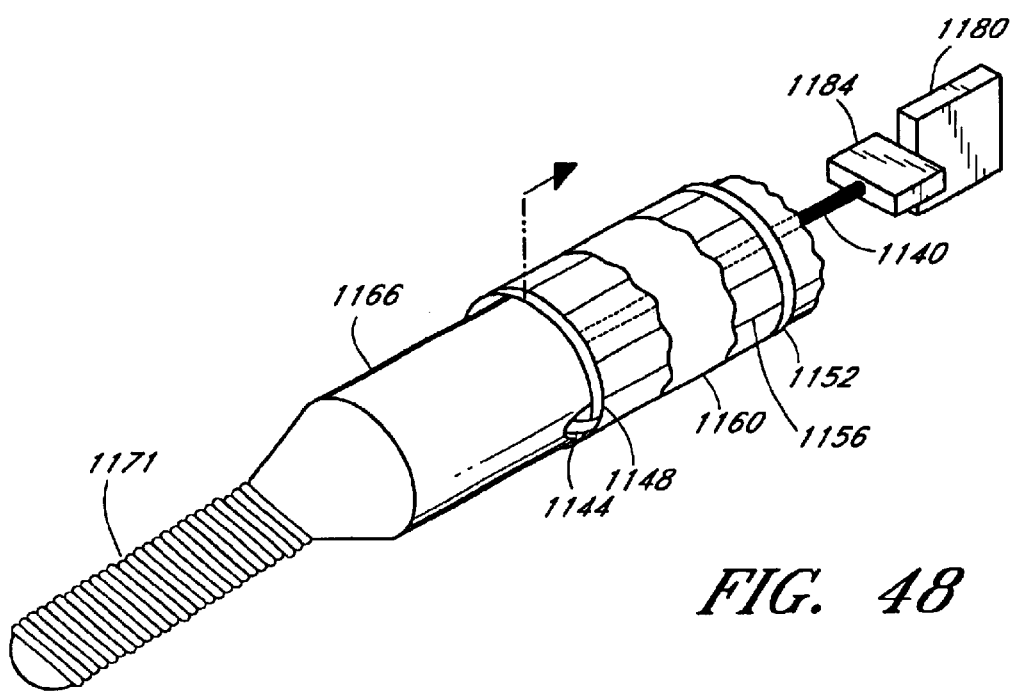
FIG. 48 is a side partial sectional view of the embodiment of FIG. 43 in which the ribbons are in their relaxed, undeployed position.
Figure 49:
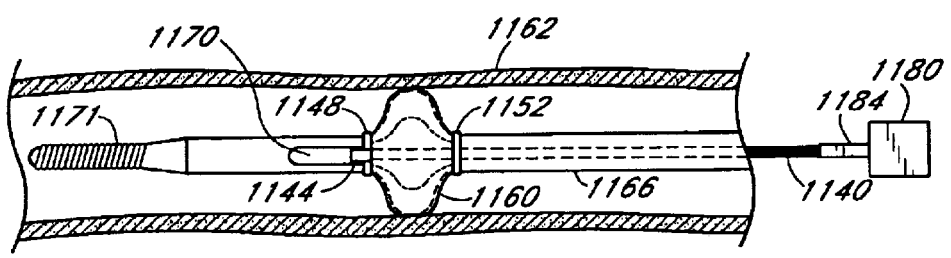
FIG. 49 is a side elevational view of the embodiment of FIG. 47 in which the ribbons are deployed, and the membrane makes a seal with the vessel.

The preferred exchange method of the present invention may also be performed over catheters or guidewires employing non-self-expanding or mechanically deployed sealing mechanisms. As shown in FIGS. 47–51B, described in further detail below, a pull wire device may be utilized for deploying an occlusive mechanism to a blood vessel while still maintaining a low profile at the proximal end of the device to allow for an exchange. As shown in FIG. 49, one pull wire device comprises an elongate member 1166 over which therapy, aspiration and other catheters may be advanced and removed. At the proximal end of the device, a rotatable handle 1180 is attached to a locking member 1184. The wire 1140 is pulled by handle 1180 from its configuration shown in FIG. 50A until the locking member 1184 clears the proximal end of elongate member 1166, at which point member 1184 is rotated to the configuration shown in FIG. 50B to hold the wire 1140 taut. The handle 1180 and locking member 1184 are dimensioned to be substantially the same size as the elongate member 1166, which preferably has an outer diameter of 0.014 inches, such that other catheters may be advanced and removed over the elongate body 166 without interference from the handle 1180 or locking member 1166.

Figure 51A:
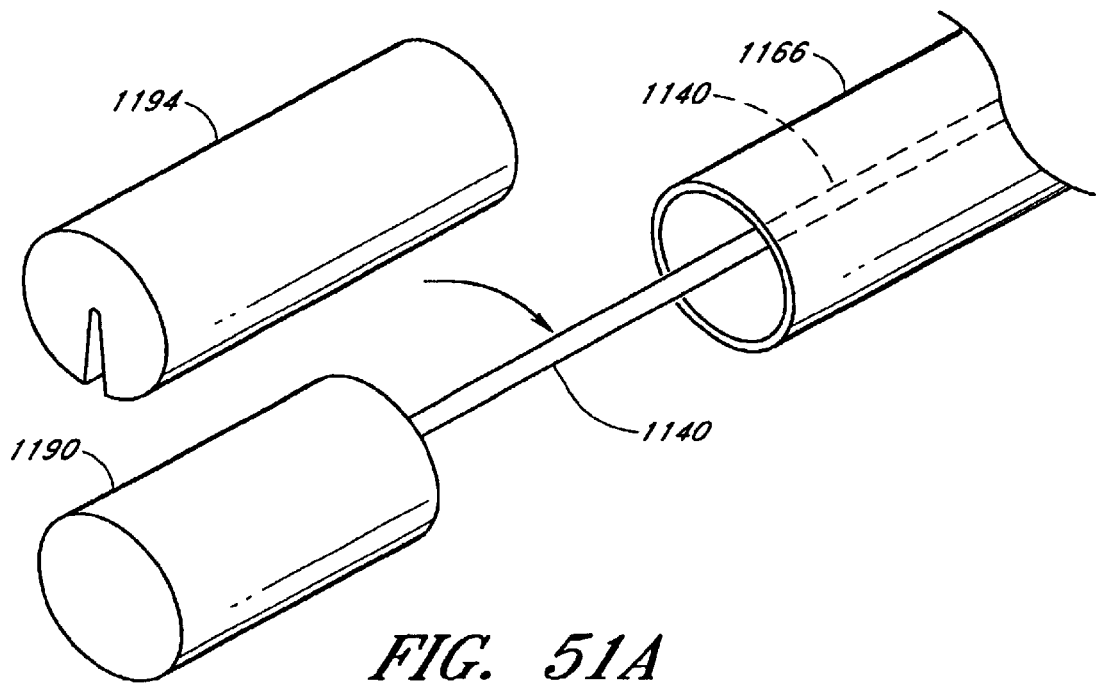
FIG. 51A is a perspective view of an alternative locking mechanism used with a wire that deploys an expansion member.

FIG. 51A shows an alternative pull wire mechanism wherein a spacer 1194 is placed between a handle 1190 and elongate body 1166 to pull wire 1140 and deploy the sealing mechanism. Because the handle 1190 and the spacer 1194 have the same diameter as the elongate body 1166, the exchange method as described above may be performed over the elongate body 1166 with catheters having relatively small inner diameters.

D. Speed of Exchange

Figure 8:
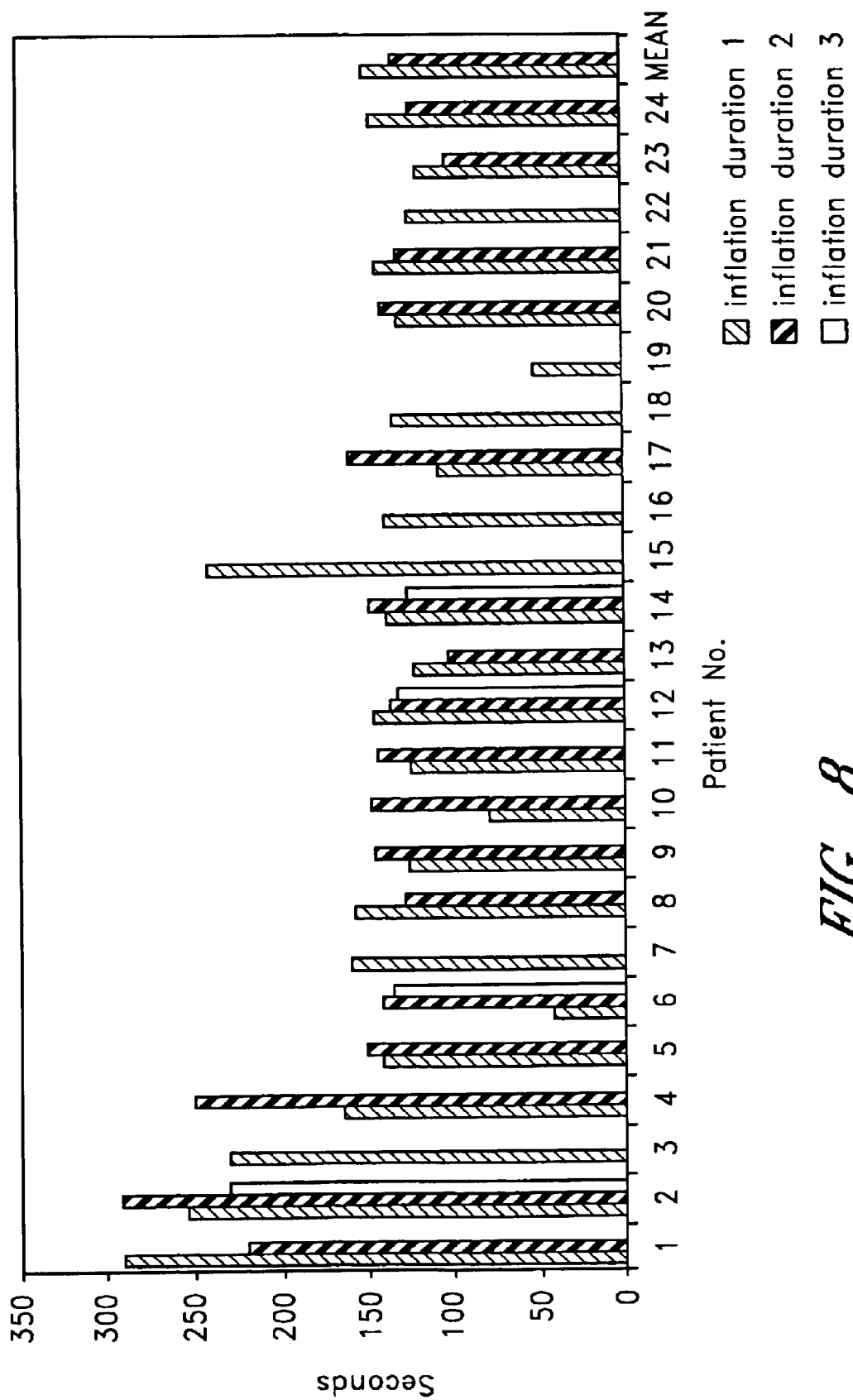
FIG. 8 is a chart showing the inflation times of a distal occlusion balloon for 24 patients being treated in a preferred aspect of the exchange method of the present invention.

The method described by a preferred aspect of the present invention is particularly advantageous in that it allows for a rapid exchange of catheters to reduce the time that a blood vessel is occluded by a balloon or other occlusive device. FIG. 8 shows experimental results for 24 patients undergoing percutaneous transluminal coronary angioplasty (PTCA) and subsequent stenting treatments in saphenous vein grafts. More particularly, FIG. 8 shows the inflation durations of occlusion balloon 20 during the treatment procedure, i.e., the time that the balloon 20 is inflated to occlude the vessel. The preferred method minimizes the times that the occlusion balloon is inflated by conducting the treatment in stages. For instance, a first stage, corresponding to a first inflation time, may comprise a sequence of therapy and aspiration treatments. After occlusion balloon inflation, a therapy catheter carrying a dilatation balloon may be used to compress the lesion. Exchanges with subsequent therapy catheters may then be performed, as long as end organs positioned downstream can tolerate the loss of blood due to blockage by the occlusion balloon. At the end of this first stage of treatment, the therapy catheter positioned on the guidewire is exchanged for an aspiration catheter. After aspiration is completed, the balloon is deflated.

Second and third inflation durations as indicated in FIG. 8 may similarly correspond to subsequent sequences of therapy and aspiration treatments. After the occlusion balloon is deflated and the first sequence ends, the aspiration catheter is exchanged for another therapy catheter. Once the second therapy catheter is in place, the occlusion balloon is reinflated and the lesion is treated in the same manner as described above. Alternatively, the second and third inflation durations may refer to a therapy catheter which deploys a stent. In this embodiment as well, the occlusion balloon is not inflated until the aspiration catheter has been exchanged with the stent deploying catheter. By performing the treatment in such a manner, the amount of time that blood flow is blocked in the treated vessel is minimized.

Thus, the inflation durations as shown in FIG. 8 generally represent the amount of time it takes to perform a therapy treatment using one or more therapy catheters exchanged over the guidewire, exchange the therapy catheter for an aspiration catheter, and aspirate emboli. As shown in FIG. 8, the mean time to accomplish this procedure was about 150 seconds. FIG. 8 also shows a general reduction in inflation durations from patient 1 to patient 24 as the clinician improved in performing the exchange over time. Accordingly, in a preferred aspect of the present invention, providing a rapid exchange method for use during emboli containment allows the clinician to quickly perform a treatment procedure while minimizing the risk to the patient due to blockage of blood flow.

Figure 16:
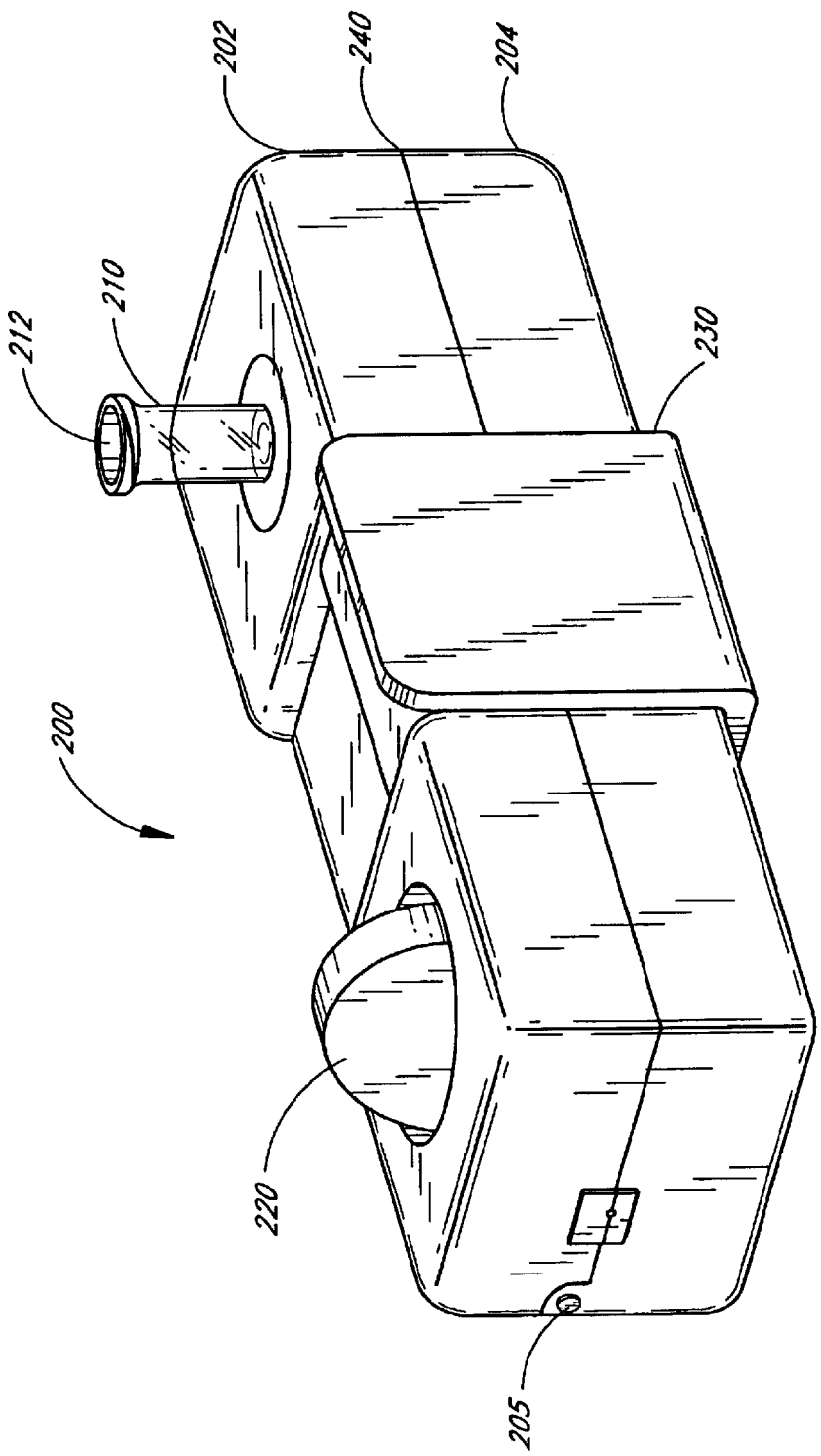
FIG. 16 is a perspective view of an inflation adaptor used to manipulate the low profile valve in a preferred aspect of the present invention.

The preferred method also reduces the treatment time by providing the catheter 10 with a side-access inflation port 22, as shown in FIG. 9. To inflate the occlusion balloon 20, the guidewire 10 is preferably inserted into an inflation adaptor, as described below with respect to FIGS. 16–19, 24–28C. By providing the inflation port 22 on the side of the guidewire 10, the adaptor can easily be attached to the guidewire and quickly inflate or deflate the balloon 20 by a simple movement such as moving actuator 220, as shown in FIG. 16. This in turn reduces the amount of time that the balloon 20 occludes a treated blood vessel.

Furthermore, use of an adaptor makes the catheter much easier to handle. Because the guidewire 10 is so small, it may difficult to handle by clinicians. By using an adaptor, however, the clinician need only insert the wire into the adaptor, close the adaptor, and actuate the adaptor, as described in further detail below.

Figure 17A:
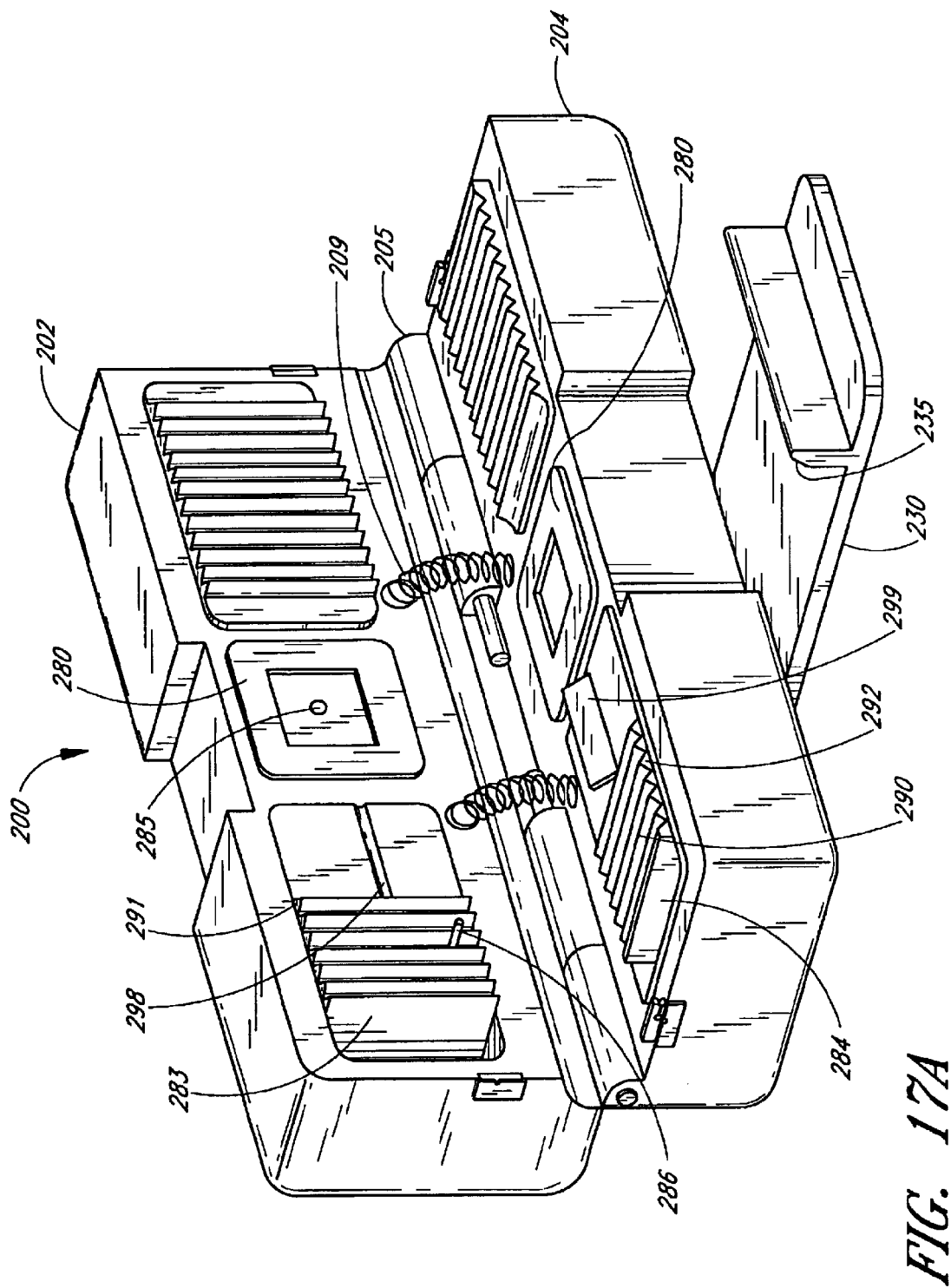
FIG. 17A is a perspective view of the interior of the inflation adaptor of FIG. 16.
Figure 17B:
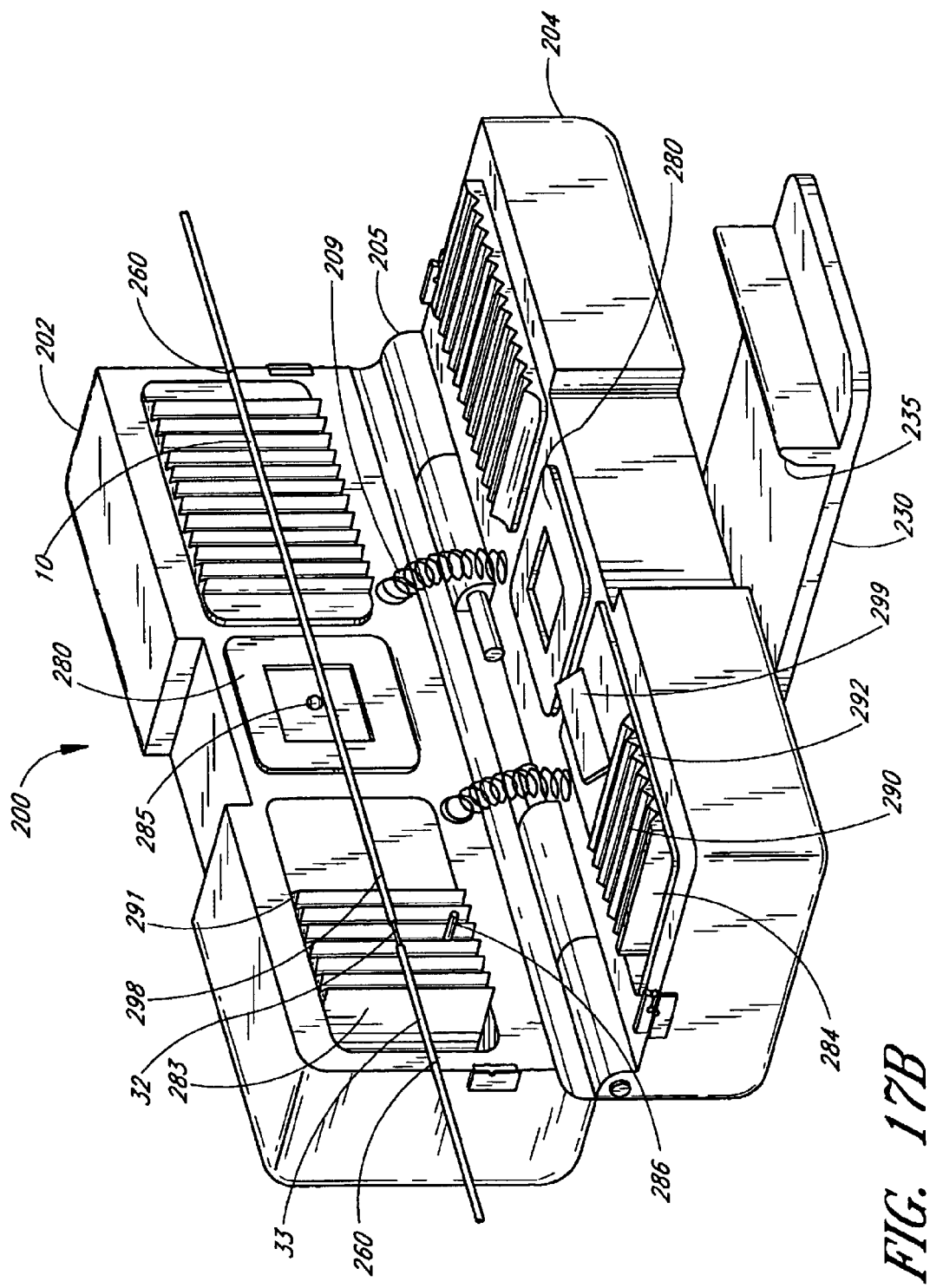
FIG. 17B is a perspective view of a catheter with a sealing member and alignment indicia being positioned in the inflation adaptor of FIG. 17A.
Figure 17C:
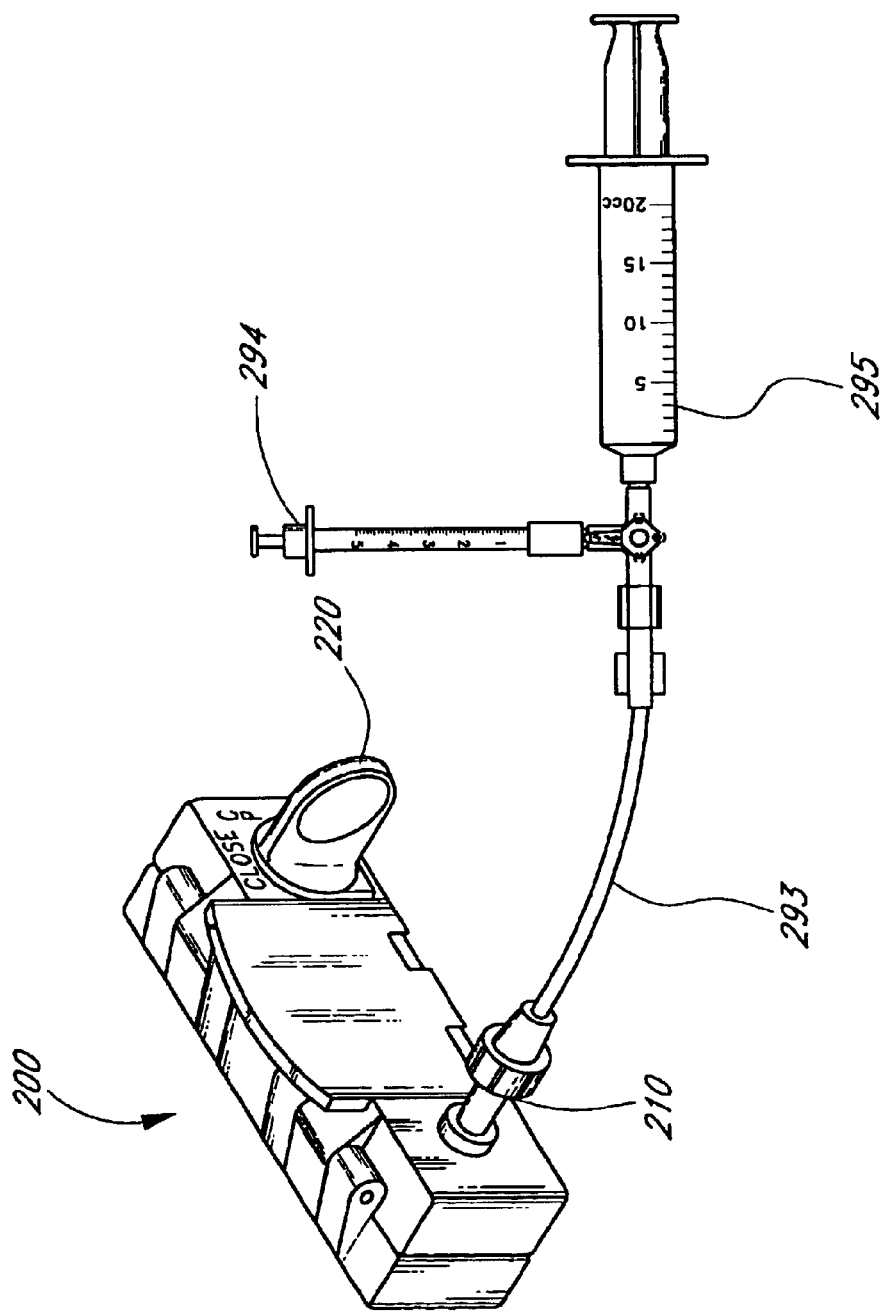
FIG. 17C is a perspective view of an inflation adaptor attached to a syringe system.

Additionally, as shown in FIG. 17C, an adaptor 200, described in further detail below, is preferably attached to a low volume syringe 294 and a high volume syringe 295. An extension line 293 is attached to fitting 210 to allow fluid flow to and from adaptor 200. Low volume syringe 294 is provided for accurate inflation of balloon 20. More particularly, low volume syringe is provided so that inflation can be performed safely and quickly. High volume syringe 295 is provided for rapid deflation of balloon 20. By using this syringe system, inflation and deflation of balloon 20 through an adaptor can be performed quickly and efficiently. Further details regarding a syringe system are described in assignee's pending application entitled SYRINGE AND METHOD FOR INFLATING LOW VOLUME CATHETER BALLOONS, application Ser. No. 09/025,991, filed Feb. 19, 1998, now abandoned the entirety of which is hereby incorporated by reference.

Moreover, by providing an access port on the side of the tubular body 18, the port 22 can be made with a large cross-section to increase the amount of fluid passing through the port. This in turn decreases the time necessary for inflating or deflating balloon 20. In addition, as described in more detail below, the use of a side-access port allows for more efficient opening and closing of the port 22. Preferably, a sealing member 30 moves slidably within tubular body 18 to plug and unplug port 22. Because member 30 remains attached to the catheter 10 even when the port 22 is open, the operator never has to remove the sealing member. Accordingly, the sealing member is always in place, thereby reducing the time that it takes to open or close inflation port 22.

Figure 17D:
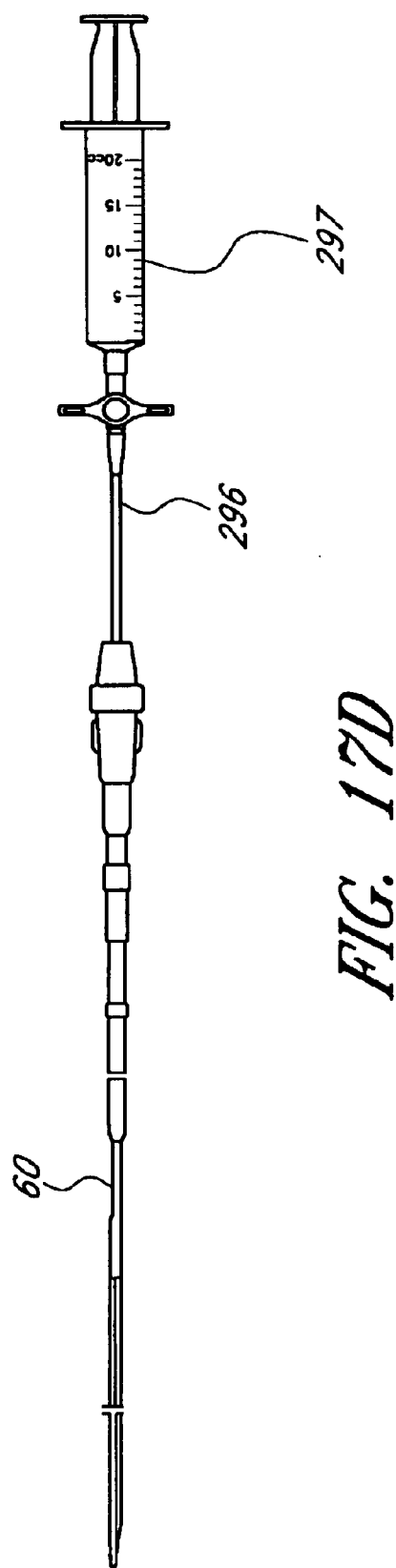
FIG. 17D is a side view of an aspiration catheter attached to a syringe system.

The speed of exchange is also increased by using an aspiration catheter with a high volume syringe. As shown in FIG. 17D, aspiration catheter 60 is attached to an aspiration line 296, connecting the aspiration catheter 60 with a high volume syringe 297. The high volume syringe allows rapid aspiration of emboli from the treated vessel, thereby reducing the time that the occlusion balloon 20 must be inflated. Further details regarding aspiration are disclosed in the above-referenced application entitled ASPIRATION SYSTEM AND METHOD.

E. Diagnostic Methods

The preferred exchange method of the present invention is also applicable to diagnostic methods. In one preferred aspect of the present invention, a method is provided wherein emboli found or created in the body are removed from the body for diagnostic testing. A guidewire with a distal occlusive device is inserted into the body to a point distal of plaque. A therapy catheter is advanced over the guidewire to the location of the plaque. After the distal occlusion device is deployed, a therapy treatment, such as inflation of a dilatation balloon or any other means as described above, is performed to break up the plaque and produce emboli. The therapy catheter is then exchanged with an aspiration catheter while the occlusion device remains deployed, and the aspiration catheter removes the particulate matter for analysis.

In the procedures conducted on the 24 patients described above in FIG. 8, particulate matter was retrieved in all but 1 of 23 procedures and 45 of 48 aspirations. Mean particle size was 168 $\mu$m (range 8 to 3,427 $\mu$m) in the major axis, 80 $\mu$m (range 6 to 815 $\mu$m) in the minor axis, with an area of 32,117 $\mu$m$^2$ (range 42 to 4,140,000 $\mu$m$^2$). Particulate material consisted predominantly of cholesterol clefts, lipid-rich macrophages, fibrous caps, necrotic core and fibrin material.

Atherosclerotic material in the precipitate sections was quantified as maximal in 5 aspirates, moderate in 9, minimal in 26, and none in 3.

Vein graft aspirate was collected in tubes containing EDTA-citrate buffer and treated with 1% saporin to lyse interfering red blood cells. The remaining material was fixed in 10% neutral buffered formalin or glutaraldehyde and processed for light microscopy and scanning electron microscopy, respectively. Immunohistochemical staining was performed in some cases to confirm the presence of foam cells, smooth muscle cells and endothelial cells. A semiquantitative analysis of particulate bulk was performed. Particulate matter examined by scanning electron microscopy was measured in its major and minor access and the resultant two dimensional area calculated. This suspended particulate matter may play a role in the pathogenesis of distal emoblization, no-reflow, infarction, and morbidity and mortality following vein graft intervention.

Tables 1 and 2 below show the results of quantitative analyses performed on vein graft aspirates. Table 1 shows the frequency of acellular plaque material in vein graft aspirates. Table 2 shows the frequency of cellular plaque material in vein graft aspirates. Values are expressed as the frequency of positive samples per case. Numbers in parentheses represent the percentage of positive samples.

TABLE 1

Frequency of Acellular Plaque Material in Vein Graft Aspirates.

| Samples | Necrotic Debris | Cholesterol Clefts | Collagen | Plaque Hemorrhage |
|---|---|---|---|---|
| PTCA | 15/15 (100) | 8/15 (23) | 4/15 (27) | 3/15 (20) |
| Stent 1 | 15/18 (83) | 6/18 (33) | 6/18 (33) | 4/18 (22) |
| Stent 2 | 7/7 (100) | 4/7 (57) | 1/7 (14) | 1/7 (14) |

TABLE 2

Frequency of Cellular Plaque Material in Vein Graft Aspirates.

| Samples | Foam Cells | Smooth Muscle Cells | Platelet Aggregates |
|---|---|---|---|
| PTCA | 14/15 (93) | 0/15 (0) | 2/15 (13) |
| Stent 1 | 17/18 (94) | 0/18 (0) | 4/18 (22) |
| Stent 2 | 6/7 (86) | 0/7 (57) | 2/7 (29) |

II. Inflatable Guidewire Apparatus

One preferred embodiment for a catheter for use in the preferred method is shown in FIG. 9. In FIG. 9, there is depicted a catheter 10 incorporating the low profile valve in a preferred aspect of the present invention. Although illustrated in the context of a simple occlusion balloon catheter, having a single inflation lumen and a single inflatable balloon, it is to be understood that the low profile valve can be readily adapted to a wide variety of balloon catheters, including those having additional functionalities, structures, or intended uses. For example, the low profile valve could be easily adapted to catheters having expandable members other than occlusion balloons, such as therapeutic dilatation balloons. Furthermore, the low profile valve may also be incorporated into catheters having two or more lumens. The manner of adapting the low profile valve to catheters having these various functionalities, structures, or intended uses will become readily apparent to those of skill in the art in view of the description which follows.

Catheter 10 generally comprises an elongate flexible tubular body 18 extending between a proximal control end 12 and a distal functional end 14. Tubular body 18 has a central lumen 40 which extends between ends 12 and 14. Lumen 40 has an opening 23 at proximal end 12, and is sealed fluid tight at distal end 14. The length of tubular body 18 may be varied considerably depending upon the desired application. For example, where catheter 10 is to be used as a guidewire for other catheters in a conventional percutaneous transluminal coronary angioplasty procedure involving femoral artery access, lengths of tubular body 18 in the range of from about 120 to about 300 centimeters are preferred, with a length of about 180 centimeters often being used. Alternately, for a different treatment procedure, not requiring as long a length of tubular body 18, shorter lengths of tubular body 18 may be provided.

Typically, tubular body 18 will have a generally circular cross-sectional configuration with an outer diameter within the range of from about 0.010 inches to 0.044 inches. Optimally, in most applications where catheter 10 is to be used as a guidewire for other catheters, the outer diameter of tubular body 18 ranges from 0.010 inches to 0.038 inches, and preferably is 0.020 inches in diameter or smaller, more preferably 0.014 inches in outer diameter or smaller. The diameter of lumen 40 will be dictated, in part, by the outside diameter of tubular body 18. For example, where tubular body 18 has an outer diameter of 0.014 inches, central lumen 40 may have an inner diameter of from about 0.008 inches to about 0.010 inches. The diameter of lumen 40 should be large enough to incorporate the low profile valve described below, and large enough to permit sufficient fluid passage for balloon inflation.

Noncircular cross-sectional configurations of lumen 40 can also be adapted for use with the low profile valve described in a preferred embodiment of the present invention. For example, triangular rectangular, oval, and other noncircular cross-sectional configurations are also easily incorporated for use with present invention, as will be appreciated by those of skill in the art. The manner of adapting the valve of the present invention will become readily apparent in view of the description which follows.

In the preferred embodiment, the tubular body 18 functions as a guidewire, and thus, tubular body 18 must have sufficient structural integrity, or "pushability," to permit catheter 10 to be advanced through vasculature to distal arterial locations without buckling or undesirable bending of tubular body 18. It is also desirable for tubular body 18 to have the ability to transmit torque, such as in those embodiments where it may be desirable to rotate tubular body 18 after insertion into a patient. A variety of biocompatible materials, known by those of skill in the art to possess these properties and to be suitable for catheter manufacture, may be used to fashion tubular body 18. For example, tubular body 18 may be made of stainless steel, or may be made of polymeric materials such as nylon, polyamide, polyimide, polyethylenes, or combinations thereof. In one preferred embodiment, the desired properties of structural integrity and torque transmission are achieved by forming tubular body 18 out of an alloy of titanium and nickel, commonly referred to as nitinol. In a more preferred embodiment, the nitinol alloy used to form tubular body 18 is comprised of about 50.8% nickel and the balance titanium, which is sold under the trade name Tinel (™) by Memry Corp. It has been found that a catheter tubular body having this composition of nickel and titanium exhibits great flexibility and improved kink resistance in comparison to other materials. One preferred embodiment of tubular body 18 is disclosed in our copending application entitled HOLLOW MEDICAL WIRES AND METHODS OF CONSTRUCTING SAME, application Ser. No. 08/812,876, filed on Mar. 6, 1997, now U.S. Pat. No. 6,068,623 the entirety of which is incorporated herein by reference.

The distal end 14 of catheter 10 is provided with an atraumatic distal tip 16, and an inflatable balloon 20, as illustrated in FIG. 9. Inflatable balloon 20 may be made from any of a variety of materials known by those of skill in the art to be suitable for balloon manufacture. For example, inflatable balloon 20 may be formed of materials having a compliant expansion profile, such as polyethylene or latex. In one preferred embodiment, where inflatable balloon 20 is to be used as an occlusion balloon, it is preferably formed of a block copolymer of styrene-ethylene-butylene-styrene (SEBS), sold under the trade name C-Flex (™). One preferred embodiment of a C-Flex occlusion balloon is disclosed in our copending application entitled BALLOON CATHETER AND METHOD OF MANUFACTURE, application Ser. No. 09/026,225, filed on Feb. 19, 1998, now U.S. Pat. No. 6,554,795 the entirety of which is incorporated herein by reference. Alternately, in those embodiments where inflatable balloon 20 is to serve as a dilatation balloon, it may be formed of materials having a noncompliant expansion profile, such as polyethylene terephthalate. Inflatable balloon 20 may be attached to tubular body 18 in any manner known to those of skill in the art, such as heat bonding or through use of adhesives.

As shown in FIG. 9, catheter 10 is provided with a side-access inflation port or opening 22 formed in tubular body 18 at a point several centimeters distal from opening 23. Inflation port 22 is in fluid communication with central lumen 40 extending through tubular body 18. A fill hole (not shown) is formed in tubular body 18 within the region enclosed by inflatable balloon 20, such that fluid passing through inflation port 22 and into lumen 40 may inflate balloon 20. Conversely, an inflated balloon 20 can be deflated by withdrawal of fluid from balloon 20, through lumen 40, and out of side-access inflation port 22.

The low profile valve may be used with catheters such as that described above, all well as with different catheters having different structures. In one preferred embodiment, the low profile valve comprises a sealing member which is movably positioned within the inner lumen of a catheter. The catheter has an inflation port, which, in some embodiments, is also an opening to the inner lumen at the proximal end of the catheter. An inflatable balloon is positioned on the distal end of the catheter, which is in fluid communication with the lumen and inflation port. The sealing member is inserted through the proximal opening into the lumen, with a portion of the sealing member extending outwardly from the proximal end of the catheter. The portion of the sealing member inserted into the lumen has a sealer portion which forms a fluid tight seal with the inner lumen to prevent fluid from passing past the sealer portion.

By application of a pushing or pulling force on the extending sealing member portion, the sealing member may be partially advanced within or withdrawn from the lumen, thereby moving the sealer portion within the lumen. In this manner, the sealer portion may be positioned within the lumen either proximally or distally of the inflation port. When the sealer portion is positioned proximally of the port, the valve is in the "open" position. When the valve is open, an unrestricted fluid pathway is established between the inflation port and the balloon, such that an external pressurized fluid source may be connected to the inflation port to inflate the balloon, or if the balloon is already inflated, the balloon may be deflated by application of a vacuum to the inflation port to withdraw fluid from the balloon. When the sealer portion is positioned distally of the inflation port, the valve is in the closed position, as the fluid tight seal between the lumen and the sealer portion prevents fluid from passing either to or from the balloon through the inflation port. Furthermore, when the valve is closed after balloon inflation, the fluid tight seal created by the sealer portion maintains the balloon in the inflated state in the absence of an external fluid source, by preventing the pressurized fluid within the balloon from escaping.

Referring to FIGS. 10, 11A and 11B, there is depicted one embodiment of the low profile valve of the present invention, as used with the catheter of FIG. 9. Catheter 10, as described above, has a side-access inflation port 22 which is in fluid communication with central lumen 40, and through which fluid may be introduced to inflate balloon 20. Central lumen 40 has an opening 23 at proximal end 12. A sealing member 30 is inserted into lumen 40 through opening 23. Sealing member 30 may be partially advanced within or withdrawn from lumen 40 by the application of a longitudinal force on sealing member 30 directed toward or away from proximal end 12, respectively.

Sealing member 30 comprises a main shaft 33, a tapering region 31, and a wire 32. Sealing member 30 may be formed as solid piece out of suitable metals, such as stainless steel, nitinol and the like. For example, sealing member 30 may be formed as a solid cylindrical piece, and then be coined down at points along its length to form tapering region 31 and wire 32. Alternately, one or more of the main shaft 33, tapering region 31, or wire 32 may be formed separately, and then attached to the other piece(s) by conventional means, such as soldering, to form sealing member 30. Polymeric materials, such as Delron (™), nylon, and the like, may also be used to form sealing member 30, either as a solid piece, or as separate pieces which are later joined to form the sealing member.

Although not required, in one preferred embodiment, main shaft 33 has an outer diameter no larger than the outer diameter of the catheter tubular body 18. Thus, if the outer diameter of tubular body 18 is 0.014 inches, the diameter of main shaft 33, and thus the largest diameter of sealing member 30, is no larger than 0.014 inches. Furthermore, it is also preferred that main shaft 33 extend proximally from opening 23 by a distance of at least several centimeters to facilitate the application of longitudinal forces on main shaft 33 to manipulate the position of wire 32 in lumen 40. Moreover, after catheter 10 has been fully inserted into a patient, an extending main shaft 33 advantageously functions much like a conventional guidewire extension, providing a starting point for the clinician to insert other catheters over main shaft 33 and catheter 10.

The combined length of catheter 10 and extending main shaft 33 may be varied considerably at the point of manufacture, and may be adapted to the requirements of the other catheters which are to be used with catheter 10 and main shaft 33. For example, where catheter 10 is to be used as a guidewire for other catheters in an "over-the-wire" embodiment, it is preferred that the total length of catheter 10 with extending main shaft 33 be about 300 centimeters. Alternately, when catheter 10 is to be used as a guidewire for other catheters in a single operator embodiment, or "RAPID-EXCHANGE" embodiment, it is preferred that the total length of catheter 10 with extending main shaft 33 be about 180 centimeters. As can be readily appreciated, the individual lengths of catheter 10 and extending main shaft 33 can be varied considerably and yet still achieve the overall desired combined length. For example, a catheter 10 having a length of 180 centimeters can be provided with an extending main shaft 33 having a length of 120 centimeters, to achieve the 300 centimeter total desired length for over-the-wire embodiments.

In another embodiment, where it is undesirable to have a long main shaft extending proximally from catheter 10, a main shaft extending proximally only several centimeters may be provided. The shorter main shaft may be provided with an attachment (not shown), which is adapted to releasably secure longer extensions to the main shaft, such that it can also be used to facilitate the use of catheter 10 as a guidewire for other catheters.

It is preferred that main shaft 33 have a larger diameter than the other portions of sealing member 30, to make it easier to apply moving forces to sealing member 30. Thus, a tapering region 31 may be disposed between main shaft 33 and wire 32, to transition the outer diameter of sealing member 30 from the larger diameter of main shaft 33 to the smaller diameter of wire 32. For the embodiment illustrated in FIGS. 9–11B, it is wire 32 which is slidably inserted through opening 23 and into lumen 40. Accordingly, the outer diameter of wire 32 must be less than the inner diameter of lumen 40, so that wire 32 may be slidably accommodated therein. Moreover, in those embodiments where the end of wire 32 extends distally past inflation port 22 when the valve is in the open position, the gap between the outer diameter of wire 32 and the inner diameter of lumen 40 must be sufficiently large so as not to significantly restrict the flow of fluid passing through lumen 40 to or from inflation port 22. Optimally, to facilitate the sliding of wire 32 within lumen 40 and to permit inflation fluid flow, wire 32 is from about 0.001 inches to about 0.004 inches smaller in outer diameter than the inner diameter of lumen 40.

In a preferred embodiment, wire 32 and catheter 10 are provided with positive stops to prevent the withdrawal of wire 32 from the proximal end of catheter 10. For the embodiment depicted in FIGS. 11A and 11B, this consists of a pair of cooperating annular rings mounted on wire 32 and lumen 40, respectively. A first annular ring 34 is coaxially and fixedly mounted on wire 32 at a point on wire 32 contained within lumen 40. A second corresponding fixed annular ring 35 projects inwardly from the interior surface of lumen 40 near proximal end 12. The inner diameter of the opening of annular lumen ring 35 is slightly larger than the outer diameter of wire 32, so as not to restrict the movement of wire 32 within lumen 40. However, the outer diameter of annular wire ring 34 is greater than the inner diameter of the opening of ring 35, such that rings 34 and 35 cooperate to prevent wire 32 from being withdrawn from the proximal end of catheter 10.

Rings 34 and 35 may be formed of any material which may be attached to wire 32 and lumen 40, respectively, and which possesses sufficient structural rigidity to act as a stop. Examples of suitable materials are metals and various hard polymers, such as stainless steel and Teflon (™). In one preferred embodiment, where wire 32 and tubular body 18 are both formed of nitinol, rings 34 and 35 are also formed of nitinol and are soldered to wire 32 and the inner surface of lumen 40, respectively.

As will be appreciated by those of skill in the art, cooperating stopping structures other than those described herein may also be used to prevent full withdrawal of wire 32 from catheter 10. For example, annular ring 34 may be replaced by one or more protrusions extending radially outwardly from wire 32, which are also adapted to cooperate with ring 35 to prevent withdrawal of wire 32. Alternately, annular ring 35 might be replaced by crimping tubular body 18 slightly to restrict movement of ring 34 to points proximal of the crimp.

A lumen sealer portion 36 is coaxially and fixedly mounted on wire 32. Sealer portion 36 is positioned on wire 32 at a point distal to ring 34, such that by partial withdrawal of wire 32 from catheter 10, as depicted in FIG. 11A, sealer portion 36 is capable of being positioned within lumen 40 at a point proximal to inflation port 22. Sealer portion 36 is also located on wire 32 at a point such that when wire 32 is fully inserted into lumen 40, as depicted in FIG. 11B, sealer portion 36 either fully covers inflation port 22, or is located within lumen 40 at a point distal to inflation port 22. The leading edge 36a and trailing edge 36b of sealer portion 36 are preferably tapered, so that the edges of sealer portion 36 do not catch upon inflation port 22 when sealer portion 36 passes by port 22.

It is preferred that sealer portion 36 form a fluid tight seal with the outer diameter of wire 32 and the inner diameter of lumen 40, such that fluid in lumen 40 is prevented from flowing past sealer portion 36. In the embodiment illustrated in FIGS. 11A and 11B, this is achieved by providing wire 32 with a sealer portion 36 that firmly contacts the entire inner circumference of a section of lumen 40 along a substantial portion of the length of sealer portion 36. The fit between the outer surface of sealer portion 36 and the inner surface of lumen 40 is tight, such that a fluid tight seal is created which prevents fluid from passing past sealer portion 36. However, sealer portion 36 must be capable of being moved within lumen 40 upon movement of main shaft 33, tapering region 31, and wire 32. Thus, the fit between sealer portion 36 and lumen 40 must not be so tight as to prevent movement of sealer portion 36 in lumen 40 upon application of sufficient longitudinal force on main shaft 33. Moreover, the fluid tight seal created by the fit between lumen 40 and sealer portion 36 must be maintained as sealer portion 36 is moved back and forth within lumen 40.

Sealer portion 36 must also be capable of maintaining a seal at fluid pressures conventionally used to inflate catheter balloons, and should be capable of maintaining a seal at pressures which exceed conventional inflation pressures. Preferably, sealer portion 36 is capable of maintaining a seal at pressures up to about 10 atmospheres, more preferably pressures up to about 30 atmospheres, and most preferably at pressures up to about 60 atmospheres. Sealer portion 36 is also preferably capable of undergoing multiple valve-opening and valve-closing cycles without losing the structural integrity required to form seals capable of withstanding pressures of from about 10 atmospheres to about 60 atmospheres. Optimally, sealer portion 36 is capable of undergoing at least 10, and preferably at least 20, valve-opening and closing events and still be capable of maintaining a fluid tight seal at a pressure of 10 atmospheres.

In one embodiment, the desired properties of sealer portion 36 are attained by forming sealer portion 36 out of an extruded polymeric tubing. Pebax (™) tubing having an inner diameter of 0.008 inches and an outer diameter of 0.017 inches, and a hardness of 40 durometers, is first necked by heating the extruded tubing to a temperature of between 210 and 250 degrees Fahrenheit. Tube pieces of about 0.5 mm in length are then cut from the larger tubing. The cut Pebax (™) tubes are then placed on a nitinol wire having an outer diameter of about 0.006 inches, and are heated and shaped to recover a tube that has an outer diameter of between 0.010–0.011 inches. The adhesive Loctite 4014 (™) may then be used to bond the heat-shaped Pebax (™) tubing to the nitinol wire. When the adhesive dries, the leading and trailing edges of the bound Pebax (™) seal may be trimmed, leaving an annular lumen contact length of about 0.010 inches (0.25 mm). The wire bearing the Pebax (™) sealer portion may then be inserted into the opening of a nitinol catheter having a lumen with an inner diameter of about 0.0096 inches. Sealer portions of this type have been observed to hold pressures of up to 30 atmospheres, and are capable of undergoing multiple valve-opening and closing events without significantly diminishing the seal strength.

As will be appreciated by those of skill in the art, different forms of Pebax (™) starting materials may be used to form sealer portion 36. For example, in another preferred embodiment, similar steps were used with a Pebax (™) tube having similar dimensions but a hardness of 70 durometers, to create a sealer portion.

It is contemplated by the present inventors that methods and materials other than those described above may be used to make a lumen sealer portion having the desired properties. For example, materials other than Pebax (™), silicone, latex rubber, C-Flex (™), Nusil (™) and gels, which are known to possess adequate surface properties to function as a sealer portion, and also be lubricous enough to be moved within lumen 40, may also be used to form sealer portion 36. In addition, sealer portion 36 may be attached to wire 32 by alternate means, such as by integrally molding sealer portion 36 to wire 32, dip forming sealer portion 36 to wire 32, as well as other means of attaching a polymeric material to a wire known to those of skill in the art.

Other embodiments of sealer portion may not create a completely fluid tight seal between the sealer portion and the inner lumen at balloon inflation pressures. In these embodiments, however, the sealer portion creates a seal which prevents substantially all inflation fluid flow past the sealer portion, such that the inflatable occlusive device is maintained in an almost fully expanded state for extended periods of at least one minute, preferably 2 or more minutes, more preferably at least 10 minutes, and optimally at least 20 minutes or longer, and still be capable of providing clinically effective occlusion of any emboli particles in the blood vessel during this time period.

In a preferred embodiment, there is provided movement-force increasing structure, to increase the force required to move sealer portion 36 from the valve-closed to the valve-open position. Structure of this type advantageously minimizes the risk of an accidental opening of the valve, and subsequent balloon deflation, during a medical procedure. In the embodiment illustrated in FIGS. 11A and 11B, this is achieved by providing a biasing spring 37, which surrounds wire 32 between stops 34 and 35. Spring 37 exerts a force on stop 34, pushing it, and thus wire 32 and sealer portion 36, in the distal direction, so that sealer portion 36 forms a fluid tight seal by either covering port 22 or by being positioned within the lumen at a point distal to port 22. Consequently, in the absence of a competing force, spring 37 maintains sealer portion 36 in the valve-closed position. Sealer portion 36 may be moved proximally to the valve-open position by application of a longitudinal force on main shaft 33 directed proximally from end 12 of sufficient magnitude to overcome the force of spring 37. Optimally, spring 37 is selected so that the force that must be applied to main shaft 33 to overcome the force of spring 37 is from about 0.3 to about 1.0 pound-foot. In alternative embodiments, the movement force increasing structure may comprise waves introduced into the wire just proximal of the sealer portion, as described below, which also may require 0.3 to 1.0 pound-foot of force to overcome.

Figure 12:
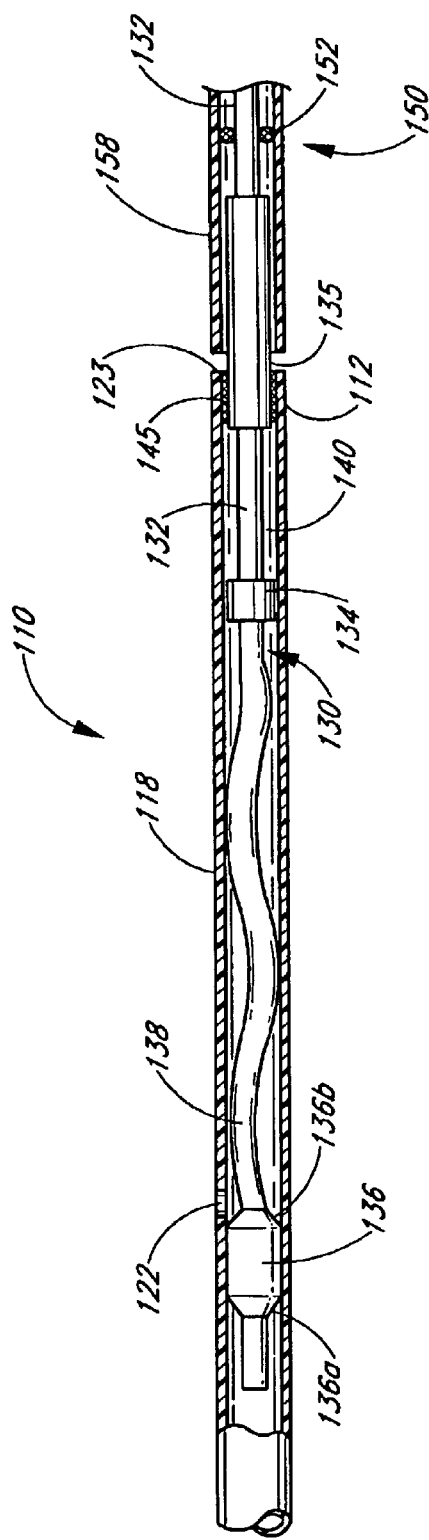
FIG. 12 is a longitudinal cross-sectional view of an alternative embodiment, showing the low profile valve in the closed position.
Figure 13:
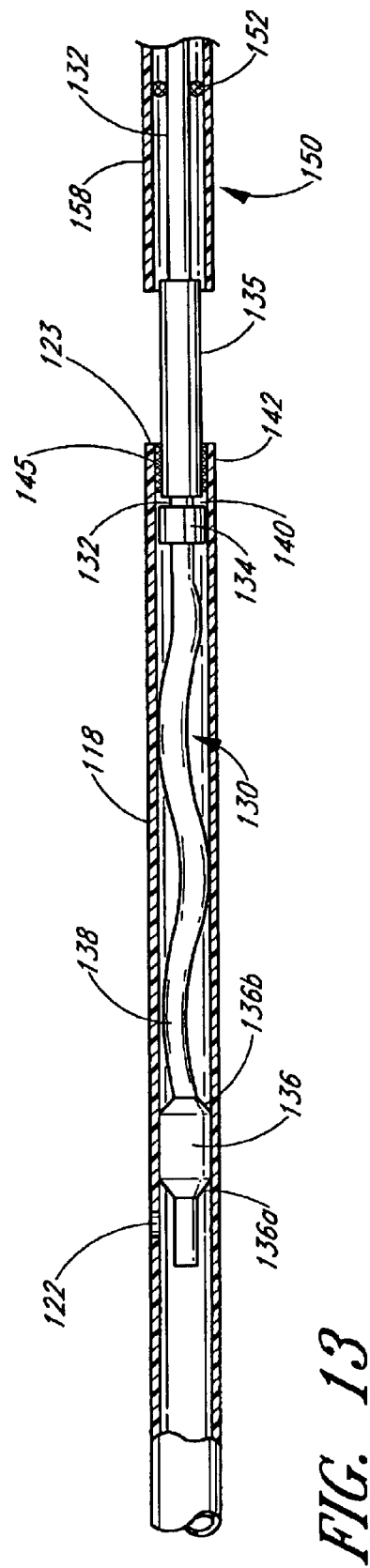
FIG. 13 is a longitudinal cross-sectional view of the embodiment of FIG. 12 showing the low profile valve in the open position.

Referring to FIGS. 12 and 13, there is illustrated in alternative embodiment of the valve of the present invention. The alternative embodiment comprises a catheter 110 which may have features which are substantially identical, in materials, structure, and function, as the catheter described in connection with FIGS. 9–11B. Catheter 110 has a proximal end 112, and a distal end (not shown) to which is mounted an expandable member, such as an inflatable balloon. A central lumen 140 extends within tubular body 118 between the proximal and distal ends. An opening 123 to lumen 140 is present at the proximal end 112 of catheter 110.

A sealing member 130 is inserted into lumen 140 through opening 123, as described previously. Sealing member 130 comprises a sealer portion 136, a wire 132, annular rings 134 and 135, and support member 150. Sealing member 130 may be formed out of materials and by methods as described previously.

As illustrated in FIGS. 12 and 13, the outer diameter of wire 132 is less than the inner diameter of lumen 140, such that sealing member 130 is slidably insertable into lumen 140. Furthermore, a lumen sealer portion 136 is coaxially and fixedly mounted to wire 132 near the distal end of wire 132. Sealer portion 136 forms a fluid tight seal with the outer diameter of wire 132 and the inner diameter of lumen 140, such that fluid introduced into lumen 140 through opening 122 is prevented from flowing past sealer portion 136 at normal balloon inflation pressures of 1 to 3 atmospheres for occlusive devices, and as much at 10 atmospheres or more for other types of balloons. Sealer portion 136 may be provided with leading edge 136a and trailing edge 136b, both tapered, to facilitate movement of sealing portion 136 proximally and distally of inflation port 122. Sealer portion 136 forms a fluid tight seal by firming contacting the entire inner circumference of a section of lumen 140 along a substantial portion of the length of sealer portion 136. As described previously, sealer portion 136 prevents substantially all fluid flow past the seal created by sealer portion 136, and the movement of sealer portion 136 proximally and distally of port 122 may be used to effect the valve-open and valve-closed positions.

Cooperating positive stops, consisting of hollow cylinders 134 and 135 are provided to prevent withdrawal of sealing member 130 from lumen 140. Hollow cylinder 135 is attached to the inner surface of lumen 140 by adhesives, soldering, crimping, or by other means known to those of skill in the art, such that the proximal portion of hollow cylinder 135 extends within lumen 140, and is secured therein, and the distal portion of cylinder 135 extends from proximal end 112. Cylinder 135 has a lumen (not shown) extending therethrough. The diameter of the cylinder lumen is larger than the outer diameter of wire 132, so that movement of wire 132 is not restricted. A second hollow cylinder 134, preferably of shorter length, is placed over wire 132 and is fixedly mounted to wire 132, by soldering, or other means, at a point distal to cylinder 135. The outer diameter of cylinder 134 is less than the inner diameter of lumen 140, so as not to restrict the movement of wire 132 within lumen 140. However, the outer diameter of cylinder 134 is greater than the inner lumen diameter of cylinder 135, so that cylinders 134 and 135 act as cooperating stops, to prevent wire 132 from being withdrawn from lumen 140. Cylinders 134 and 135 may be formed of any material which may be attached to wire 132 and lumen 140, respectively, and which possesses sufficient structural rigidity to act as a stop. Examples of suitable materials are metals and various hard polymers, such as stainless steel, Teflon (™), and the like. In one preferred embodiment, where wire 132 and tubular body 118 are both formed of nitinol, cylinders 134 and 135 are also formed of nitinol, and are soldered to wire 132 and the inner surface of lumen 140, respectively.

The distal portion of cylinder 135 extending from proximal end 112 is inserted into support member 150. Support member 150 comprises a tubular body 158 having an outer diameter and inner lumen diameter which are approximately the same as tubular body 118. Consequently, because the outer diameter of cylinder 135 is less than the inner lumen diameter of support member 150, the extending portion of cylinder 135 is slidably disposed within the support member 150 inner lumen.

Wire 132 extends proximally from cylinder 135 within support member 150, as shown in FIGS. 12 and 13. A segment of wire 132 within support member 150 is secured to support member 150 at point 152. Wire 132 may be secured to support member 150 by any means known to those of skill in the art, including use of adhesives, crimping, soldering or welding. Because wire 132 is secured to support member 150, the application of longitudinal forces on support member 150 results in movement of sealing member 130 within lumen 140, to open or close the valve, as described above with respect to FIGS. 9–11B. Advantageously, use of support member 150 protects wire 132 from undesirable kinking or bending when sealing member 130 is moved.

As illustrated in FIGS. 12 and 13, sealing member 130 has movement-force increasing structure which increases the force required to move sealing member 130 within lumen 140. The movement-force increasing structure consists of waves 138 formed in wire 132 just proximal to sealer portion 136. Waves 138 contact the inner surface of lumen 140, thereby increasing the frictional forces which must be overcome to move wire 132 within lumen 140. In one preferred embodiment, where wire 132 is made of nitinol and has an outer diameter of 0.006 inches, and is inserted into a nitinol catheter which has an inner lumen 140 with the diameter of about 0.010 inches, waves are formed on wire 132 for one and one-half cycles with an amplitude of about 0.016 inches to increase the valve-opening movement force.

Referring to FIGS. 14 and 15, there is illustrated another embodiment of the present invention. Referring to FIG. 14, there is provided a catheter 400 having a tubular body 418 and inflatable balloon (not shown) as described above. Catheter 400 may be formed of materials and methods as described above, and may have structural aspects identical to those described previously, except where otherwise noted. In particular, as shown in FIGS. 14 and 15, catheter 400 is not provided with a side-access port on the catheter tubular body, nor is there provided cooperating positive stops on the wire and lumen. Instead, the sealer portion may be fully withdrawn from the lumen. Once the sealer portion is removed, the proximal opening serves as an access port for attached devices to inflate or deflate the balloon. The sealer portion can be inserted through the proximal opening into the lumen after balloon inflation to maintain the balloon in the inflated state.

Catheter 400 has a proximal end 412, and a distal end (not shown) to which is mounted an inflatable balloon. A central lumen 440 extends within tubular body 418 between the proximal and distal ends. An opening 423 to lumen 440 is present at the proximal end 412 of catheter 400.

A sealing member 430 is inserted into lumen 440 through opening 423. Sealing member 430 has a main shaft 433, a tapering region 431, and a wire 432. Sealing member 430 may be formed of materials and by methods as described previously. As illustrated in FIGS. 14 and 15, the outer diameter of main shaft 433 is less than the inner diameter of lumen 440, such that main shaft 433 is slidably insertable into lumen 440. In addition, the outer diameters of tapering region 431 and wire 432 are also smaller than main shaft 433, and thus lumen 440, such that tapering region 431 and wire 432 are also slidably insertable in lumen 440. A portion of main shaft 433 preferably extends proximally from end 412, to facilitate application of moving forces upon sealing member 430 to move wire 432 within lumen 440, as described previously.

As illustrated in FIGS. 14 and 15, sealing member 430 has movement-force increasing structure which increases the force required to move sealing member 430 within lumen 440. The movement-force increasing structure consists of waves 438a and 438b formed in wire 432 near its distal end. Waves 438a and 438b contact the inner surface of lumen 440, thereby increasing the frictional force which must be overcome to move wire 432 within lumen 440. In one preferred embodiment, where wire 432 is made of nitinol and has an outer diameter of 0.006 inches, and is inserted into a nitinol catheter which has an inner lumen 440 with a diameter of about 0.010 inches, waves are formed on wire 432 for 1½ cycles with an amplitude of about 0.016 inches to increase the valve-opening movement force.

A lumen sealer portion 436 is coaxially and fixedly mounted on wire 432. Sealer portion 436 forms a fluid tight seal with the outer diameter of wire 432 and the inner diameter of lumen 440, such that fluid introduced into lumen 440 through opening 423 is prevented from flowing past sealer portion 436 when sealer portion 436 is inserted into lumen 440. Sealer portion 436 forms the fluid tight seal by firmly contacting the entire inner circumference of a section of lumen 440 along a substantial portion of the length of sealer portion 436, and may be formed of materials and by methods as previously described.

In some removable sealing member embodiments, the sealing member is not provided with a separate sealing portion, as described above. In these embodiments, the sealing member itself functions as a sealing portion which is inserted into the proximal opening to restrict fluid flow, and which may be partially or wholly removed to provide for a fluid pathway between the proximal opening and an expandable member on the distal end of the catheter. Preferably, the sealing members of these embodiments comprise a tapering rod, which at its distal end, has an outer diameter smaller than the inner lumen diameter of the catheter in which it is inserted as a plug, such that the distal end of the rod may be easily inserted into the catheter lumen through the proximal opening. The tapering rod increases in outside diameter at points proximal to the distal end. Consequently, one or more points of the rod have an outside diameter greater than the inner lumen diameter of the catheter in which it is inserted as a plug, such that by forcing the rod into proximal opening, the larger outer diameter of the rod forms a relatively fluid tight seal with the catheter lumen at the proximal opening of the catheter. An O-ring, or other polymeric structure, may be mounted in the inner lumen of the catheter at or near the proximal opening, to cooperate with the tapering rod in the creation of the seal. Thus, in this embodiment, the point where the seal is created does not move with respect to the catheter, but is instead stationary at or near the proximal opening of the catheter.

Figure 20:
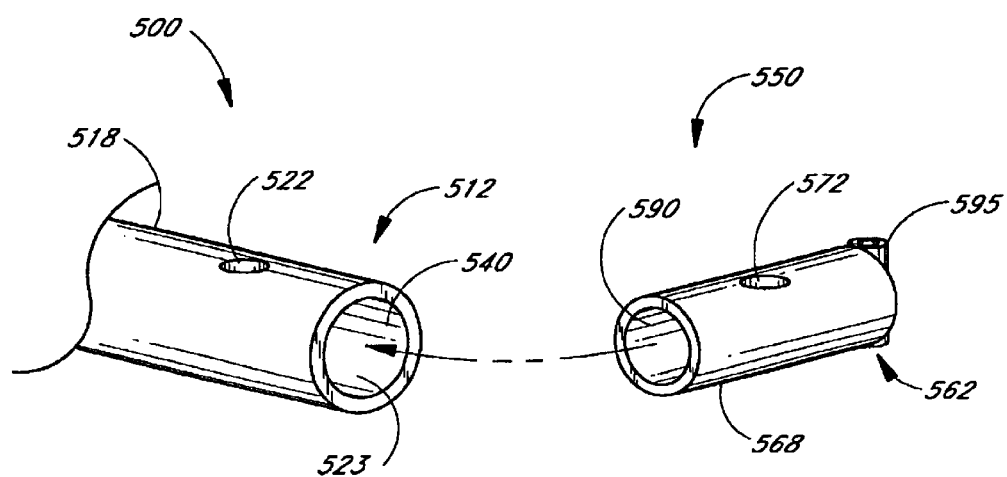
FIGS. 20 and 21 are exploded views of alternative embodiments of the low profile valve in a preferred aspect of the present invention.

Referring to FIG. 20, there is depicted an alternative embodiment of the valve the present invention. The alternative embodiment is provided to a catheter 500, formed of a tubular body 518 and having a proximal end 512. Catheter 500 has an opening 523 at is proximal end, and a lumen 540 extending the length of the tubular body. Lumen 540 is in fluid communication with an expandable member (not shown) mounted on the distal end of tubular body 518. A side-access port 522 is provided in tubular body 518 at a point distal to proximal end 512. Catheter 500 may have aspects identical, both in structure, dimensions, materials, and construction, to catheters described previously.

A sealing member 550 is positioned within lumen 540 near proximal opening 523 and side-access port 522. Sealing member 550 is formed from a short tubular body 568, having a lumen 590, which is sealed at end 562, but open at the other end. Sealing member 550 has an outer diameter slightly larger that the inner diameter of lumen 540, but smaller than the outer diameter of tubular body 518, such that sealing member 550 may be tightly fit within lumen 540 through opening 523, to form a fluid tight seal over catheter proximal opening 523. Cooperating stopping structures (not shown) may be provided to sealing member 550 and catheter 500 to prevent removal of sealing member 550 from lumen 540 at elevated pressures. Sealing member 550 may be formed out of the same materials as tubular body 518.

Tubular body 568 is provided with an opening 572 extending therethrough. Opening 572 is positioned on tubular body 568 such that opening 572 is capable of aligning with side-access port 522 when sealing member 550 is rotated within lumen 540, or is moved proximally or distally within lumen 540. A rotation element 595, such as a perpendicular attachment, may be provided facilitate rotation of sealing member 550 within lumen 540. Other rotation elements, such as notches or grooves, may be used in place of the perpendicular attachment, as will be appreciated by those of skill in the art.

Sealing member 550 functions as a valve within catheter 500, controlling fluid flow through side-access port 522. When sealing member 550 is rotated so that port 522 and opening 572 are aligned, fluid may flow through port 522 through lumen 540 to inflate the occlusive device. Upon the desired inflation, sealing member 550 may be rotated, as for example by ninety degrees, or moved proximally or distally within lumen 540, such that opening 572 is no longer aligned with port 522, and tubular body 568 blocks fluid flow through port 522.

Figure 21:
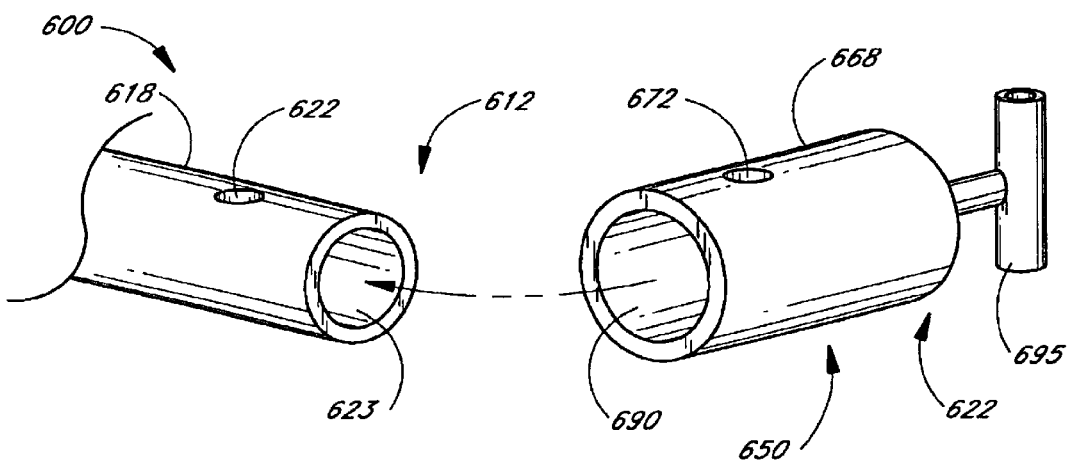

Shown in FIG. 21, is an alternative embodiment of the rotatable sealing member. Numerals corresponding to those of the embodiment of FIG. 20 have been used to illustrate the similar structural aspects between the two embodiments. Sealing member 650 is identical in construction to the sealing member of FIG. 20, except that sealing member 650 is somewhat larger, and is adapted to be slipped over tubular body 618. The respective diameters of tubular body 618 and sealing member lumen 690 are such that a fluid tight seal is created over lumen 623. Side-access inflation port 622 may be aligned with opening 672, as above, by rotation or longitudinal movement, to provide fluid access to lumen 640 through port 622.

In certain embodiments, it may be desirable for sealing members 550 and 650 to have a longer length, such that they may function as an extension for other catheters to be inserted over catheters 500 and 600. In these embodiments, sealing members 550 and 650 may be formed with longer tubular bodies, or be provided with attachments so that extension members may be releasably secured thereto.

Figure 22:
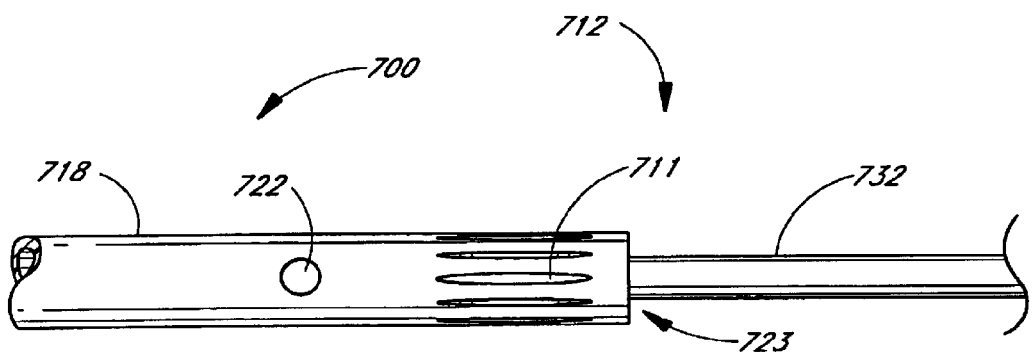
FIG. 22 is an alternative embodiment of the valve in a preferred aspect of the present invention featuring a built in spring bias.
Figure 23A:
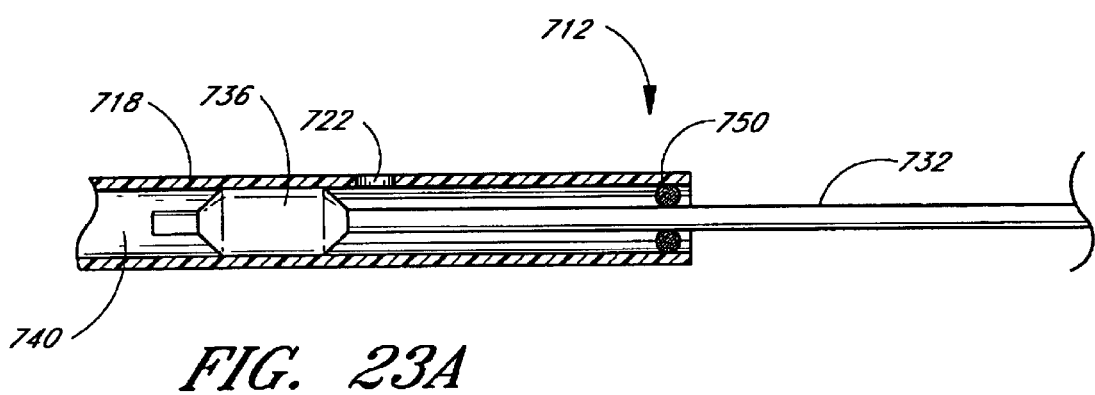
FIGS. 23A and 23B are longitudinal cross-sectional views of the catheter proximal end of FIG. 22 showing the valve in the closed and open position, respectively.
Figure 23B:
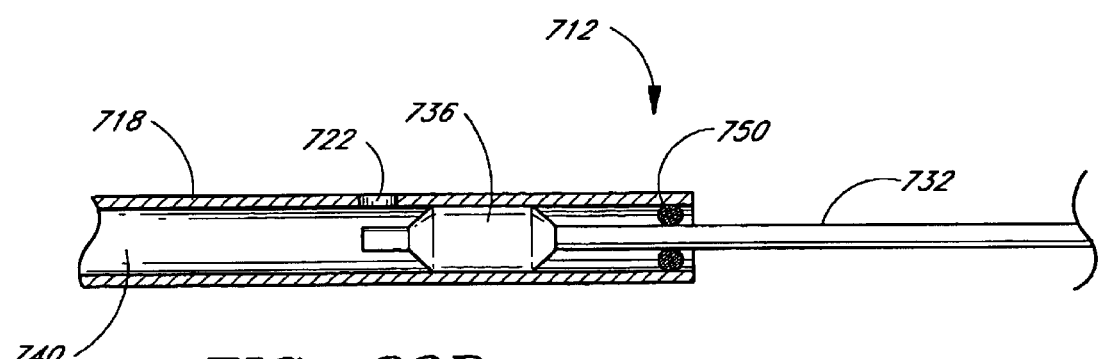

Referring to FIGS. 22, 23A and 23B, there is illustrated an alternative embodiment of the present invention featuring a self-closing valve. The alternative embodiment comprises a catheter 700 having an elongate flexible tubular body 718 extending between a proximal control end 712 and a distal functional end (not shown), and having a balloon (not shown) as described previously. Tubular body 718 has central lumen 740 which extends between the proximal and distal ends. Lumen 740 has an opening 723 at proximal end 712, and is sealed fluid tight at the distal end. A side access inflation port 722 is formed in tubular body 718 at a point distal of opening 723. Inflation port 722 and lumen 740 are in fluid communication with the distal inflatable balloon, as described previously.

A wire 732 is inserted into opening 723, and is slidably disposed within lumen 740. Accordingly, the outer diameter of the wire 732 must be less than the inner diameter of lumen 740, so that wire 732 may be slidably accommodated therein. A sealer portion 736 is coaxially mounted on wire 732. Sealer portion 736 is of similar type and construction to the sealer portion described in connection with FIGS. 9–11B. Sealer portion 736 is positioned on wire 732 at a point distal to inflation port 722, and forms fluid-tight seal with the outer diameter of wire 732 and the inner diameter of lumen 740, such that fluid introduced into lumen 740 is prevented from flowing past sealer portion 736. Consequently, because sealer portion 736 is positioned with lumen 740 distal to inflation port 722, sealer portion 736 is in the valve-closed position.

In the embodiment depicted in FIGS. 22–23B, tubular body 718 is formed from a material having a certain degree of elasticity, such that if the proximal end 712 of tubular body 718 is secured to wire 732 at point 750, and a longitudinal force is applied to tubular body 718 in a direction distal to end 712, the elasticity of tubular body 718 results in the shifting of inflation port 722 in the distal direction. Moreover, slits 711 may be formed in tubular body 718 near proximal end 712 to enhance the elastic response of tubular body 718, thereby increasing the distal translocation of inflation port 722 upon application of an axial force to tubular body 718. Wire 732 may be secured to tubular body 718 by any means known to those of skill in the art, such as adhesives, welding, soldering, or crimping.

In a preferred embodiment, tubular body 718 is made out of nitinol, and has at least 8% elasticity when longitudinal slits 711 are introduced at the proximal end. As can be observed in FIG. 23A, in the absence of any longitudinal force applied to tubular body 718, sealer portion 736 is positioned within lumen 740 at a point distal to inflation port 722, such that fluid may not pass through port 722 to inflate or deflate the balloon. However, if a longitudinal force is applied to tubular body 718 in the distal direction, and the proximal end of tubular body 718 and wire 732 are held in position, tubular body will stretch, as shown in FIG. 23B, and inflation port 722 will be translocated in the distal direction so that sealer portion 736 will be located within the lumen proximally of port 722. This will establish an unrestricted fluid pathway between inflation port 722 and the distal balloon, so that the balloon may be either inflated or deflated by passage of fluid through port 722. Upon removal of the longitudinal force, the elastic response of tubular body 718 will result in proximal translocation of inflation port 722, and sealer portion 736 will once again be in the valve-closed position.

Referring to FIGS. 16 and 17A, there is illustrated an inflation adaptor 200 which may be used to inflate and to open and close the low profile valve depicted in FIGS. 9–13. Inflation adaptor 200 comprises a housing having a first half 202 and a second half 204, which are preferably formed of metal, medical grade polycarbonate, or the like. Halves 202 and 204 are attached to one another by a pair of hinges 205 positioned on one of the lateral edges of each half, such that halves 202 and 204 may be separated or joined in a clam shell manner as depicted in FIGS. 16 and 17. A locking clip 230 secures half 202 to half 204 while inflation adaptor 200 is in use. Locking clip 230 may be provided with an angled leading edge 235 to facilitate closing of clip 230 to secure halves 202 and 204 together. Springs 209 may also be provided to facilitate opening of adaptor 200.

A groove 240 separates first half 202 from second half 204 when the halves are closed and clip 230 is secured. Groove 240 is of sufficient width to accept the proximal end of a catheter having the low profile valve, as described in detail above. A fitting 210 is positioned on half 202, to create an inflation passageway 212 which terminates in opening 285 on the interior surface of first half 202. Fitting 210 is preferably a standard luer connector which may be attached to a variety of existing external pressurized fluid sources, although other types of fittings, such as tubings, quick connects, and Y-site connections, may be easily substituted for a luer fitting.

A seal comprising a pair of gaskets 280 is positioned around opening 285 on the interior surfaces of halves 202 and 204. Gaskets 280 are in alignment, such that when halves 202 and 204 are brought together and secured by locking clip 230, a fluid tight inflation chamber is created within the interior region defined by gaskets 280. The fluid tight inflation chamber is in fluid communication with fitting 210 via inflation passageway 212, so that a pressurized inflation fluid may be introduced into the fluid tight inflation chamber by attaching an external pressurized fluid source to fitting 210. Moreover, gaskets 280 are preferably formed of resilient materials, such as silicone, C-Flex (™) and Pebax (™), so that gaskets 280 may form-fit over a catheter tubular body which extends across the lateral edges of gaskets 280, to create the fluid tight chamber.

An actuator 220 is positioned on the external surface of half 202. In the embodiment illustrated in FIGS. 16 and 17, actuator 220 controls a cam which operates a sliding panel 283 on the interior surface of half 202. Sliding panel 283 moves back and forth along a line which bisects opening 285. When actuator 220 is moved to a first position, sliding panel 283 moves toward opening 285 along this line. When actuator 220 is moved to a second position, sliding panel 283 moves away from opening 285 along the same line. A corresponding sliding panel 284 is positioned on half 204, such that panels 283 and 284 are aligned and move together when the position of actuator 220 is changed. To facilitate coordinated movement of panels 283 and 284, a pin 286, or such other similar engagement structure, may be provided to releasably secure panel 283 to panel 284 when the adaptor is closed. The length of travel of panels 283 and 284 is preferably adjusted to provide the minimum sufficient distance to position the sealing member in the valve open or valve closed position, as desired.

Panels 283 and 284 each have a roughened surface 290, to facilitate the frictional engagement of panels 283 and 284 with the main shaft portion of the low profile valve. In a preferred embodiment, panels 283 and 284 are both made of silicone, and roughened surface 290 comprises teeth 291 and grooves 292 formed on each of panels 283 and 284. The teeth 291 and grooves 292 cooperate, to permit the teeth of one panel to fit into the grooves of the opposite panel when the adaptor is closed.

For ease of understanding, the operation of inflation adaptor 200 to inflate the balloon of the catheter of FIGS. 9–11B will now be described. Actuator 220 is moved to the first position, so that sliding panels 283 and 284 are moved closer to opening 285. Locking clip 230 is then undone, exposing groove 240. Halves 202 and 204 are then partially separated, and catheter 10, with the balloon 20 deflated, is inserted into the inflation adaptor. As described previously, catheter 10 has an inflation port 22 located near proximal end 12, and a main shaft 33 extending from proximal end 12. Catheter 10, with the low profile valve in the closed position, is placed within groove 240 of partially open adaptor 200, and catheter 10 and main shaft 33 are placed within securing clips 271 and 272, such that when halves 202 and 204 are closed, inflation port 22 will lie within the fluid tight inflation chamber created by gaskets 280, and the extending portion of main shaft 33, but not proximal end 12, will rest between sliding panels 283 and 284. An alignment slot 298 and overlying shelf 299 may be provided to facilitate alignment and prevent buckling or kinking of the catheter and sealing member during use.

As shown in FIG. 17B, in one embodiment, indicia 260 are provided on catheter 10 and main shaft 33, which when aligned with indicia 270 on inflation adaptor 200, result in alignment of inflation port 22 with the fluid tight inflation chamber of adaptor 200, and alignment of main shaft 33 with sliding panels 283 and 284, when catheter 10 and sealing member 30 are inserted into groove 240. Indicia 260 and 270 may take the form of markings, grooves or notches, or any other suitable means of aligning the valve with the inflation adaptor alignment indicia, may be provided. Preferably, the gap between indicia 260 on catheter 10 and main shaft 33 is approximately equal to the space between clips 271 and 272, such that by placing indicia 260 within clips 271 and 272, catheter 10 and main shaft 33 are properly aligned within adaptor 200.

Indicia solely on the catheter tubular body may also be used to facilitate correct alignment. For example, two visible markings may be place on the catheter on either side of the catheter inflation access port. By inserting the catheter into lower half 204 so that both of these markings are place within lower half gasket 280, the catheter inflation access port will be within the fluid tight inflation chamber created by gaskets 280 when halves 202 and 204 are secured to one another.

Once main shaft 33 and inflation port 22 are properly aligned within adaptor 200, locking clip 230 is secured. Inflation port 22 now lies within the fluid tight inflation chamber created by gaskets 280, and main shaft 33 rests between sliding panels 283 and 284. The clinician may then attach an external pressurized fluid source to fitting 210.

To inflate balloon 20, the clinician moves actuator 220 from the first position to the second position, thereby causing sliding panels 283 and 284 to move away from opening 285. Because main shaft 33 is firmly secured between panels 283 and 284, a longitudinal force directed away from proximal end 12 is applied to main shaft 33. The longitudinal force on main shaft 33 results in wire 32 being partially withdrawn from lumen 40, which causes sealer portion 36 on wire 32 to be moved to a position within lumen 40 which is proximal of inflation port 22. The movement of sealer portion 36 proximally of inflation port 22 opens the low profile valve, by establishing an unrestricted fluid pathway between inflation port 22 and balloon 20.

The external pressurized fluid source may then be activated, as for example by pushing the plunger on a syringe, such that pressurized fluid passes through passageway 212 and opening 285 into the fluid tight inflation chamber. The pressurized fluid then passes through inflation port 22 and lumen 40, to inflate balloon 20.

Inflated balloon 20 may be maintained in the inflated state, in the absence of the pressurized fluid source, by closing the low profile valve. This is accomplished by moving actuator 220 back to the first position, thereby causing sliding panels 283 and 284 to move toward opening 285. The moving panels apply a longitudinal force, directed toward proximal end 12 to main shaft 33, causing wire 32 to be further inserted into lumen 40. Consequently, sealer portion 36 is moved from a position within lumen 40 which is proximal to inflation port 22 to a position in lumen 40 which is distal to inflation port 22. The fluid tight seal created by sealer portion 36 traps the pressurized fluid within lumen 40 and balloon 20, thereby maintaining balloon 20 in the inflated state. The external pressurized fluid source may then be deactivated and removed. Once the low profile valve is closed, inflation adaptor 200 may be removed by unlocking clip 230, and removing catheter 10 and main shaft 33 from groove 240.

Figures 18, 19:
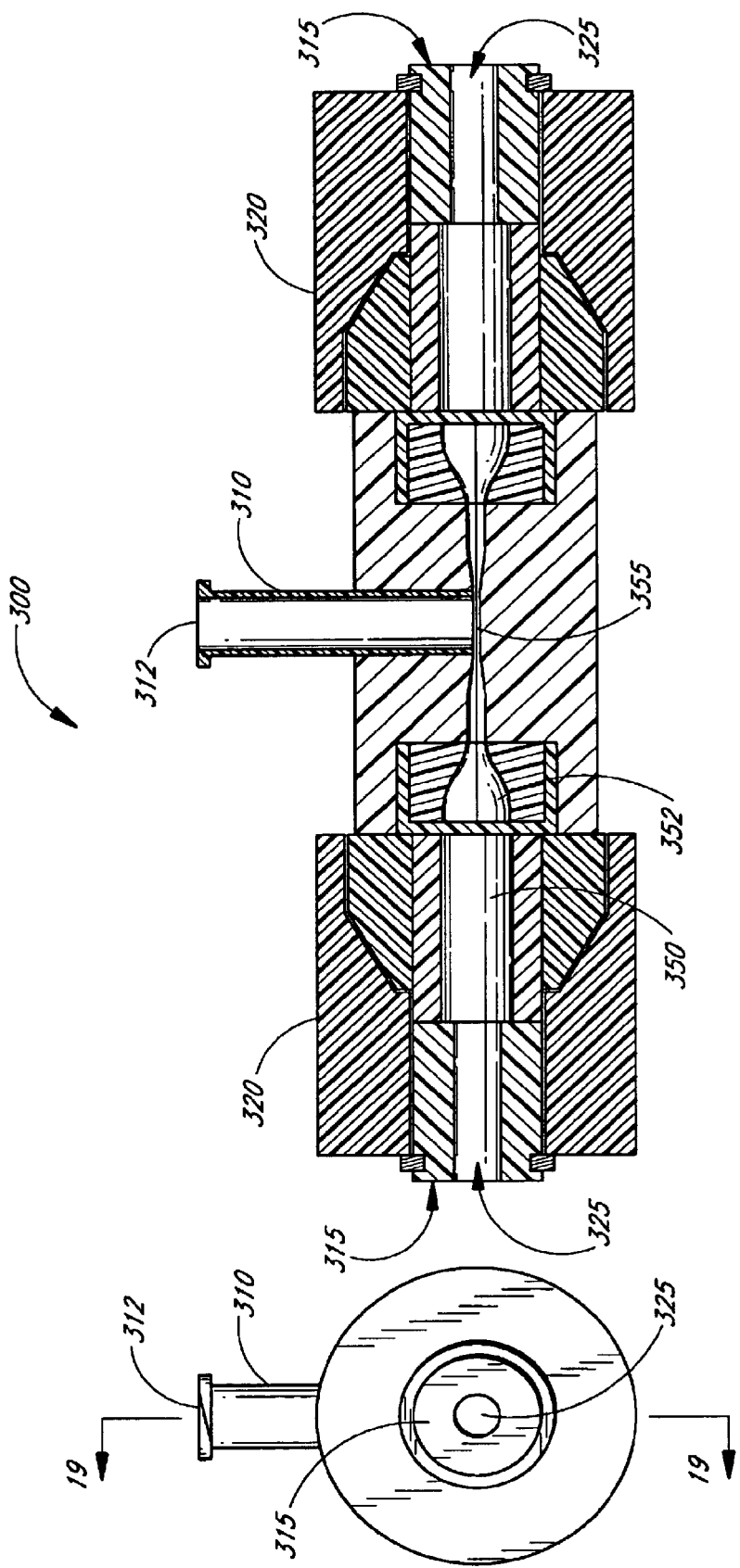
FIG. 18 is an end view of an alternative embodiment of the inflation adaptor.
FIG. 19 is a cross-sectional view of the inflation adaptor of FIG. 18 along lines 19—19.

Referring to FIGS. 18 and 19, there is illustrated an alternative embodiment of an inflation adaptor especially adapted for manipulating removable low profile valves, although it may be used with side-access embodiments as well.

Moreover, it should also be appreciated that adaptor 200 and similar type adaptors may also be used to manipulate removable valve embodiments.

Adaptor 300 comprises an outer sleeve 320 formed of metal, medical grade polycarbonate, or similar such materials. Outer sleeve 300 defines a tapering inner lumen 350. Lumen 350 tapers from large diameter 352 which is significantly greater than the outer diameter of the catheter tubular bodies inserted into lumen 350, to a smaller diameter 355, which is slightly larger the outer diameter of the catheter tubular body. Lumen 350 is in fluid communication with an inflation passageway 312 formed by fitting 310, so that a pressurized inflation fluid may be introduced into lumen 350. Releasable seals 315 are positioned at each end of lumen 350, such as to create a fluid tight inflation chamber within lumen 350 when a pressurized fluid source is attached. Releasable seals 350 may comprise any type of seal known to those of skill in the are, such as Toughy Borst connectors, hemostatic valves, and the like. Releasable seals 350 may also act to secure any catheters and sealing members inserted within the releasable seal openings 325

In use, a catheter and sealing member, such as that described in connection with FIGS. 14–15, is inserted into opening 325 after seals 315 have been opened. The catheter and sealing member are positioned under passageway 312, and the sealing member is removed from the proximal opening of the catheter. A fluid passageway is thereby created between the proximal catheter opening and the expandable member of the distal end of the catheter. Seals 350 are closed to create a fluid tight chamber, and a vacuum and/or pressurized inflation fluid is applied, to inflate or deflate the balloon. After the desired inflation or deflation has occurred, the sealing member may be introduced into the proximal opening of the catheter tubular body to seal the lumen, either by hand or by a movable actuator (not shown). Seals 350 may then be loosened, and the end access adaptor 300 removed by sliding the adaptor off the end of the catheter and sealing member.

Referring to FIGS. 24–26B, there is illustrated an alternative embodiment inflation adaptor 800 which may also be used in conjunction with the low profile valves of the present invention, of the type depicted in FIGS. 9–13, to inflate or deflate catheter balloons. Inflation adaptor 800 comprises a housing having a first half 802 and a second half 804, which are preferably formed of a medical grade polycarbonate. However, as will be appreciated by those of skill in the art, a great many other materials may by used to form adaptor 800, including metals such as 300 series stainless steel and 400 series stainless steel, and polymeric materials such as Acrylonitrile-butadiene-styrene (ABS), Acrylics, and Styrene-acrylonitriles. Furthermore, the individual halves 802 and 804 may be manufactured in a variety of different ways. For example, where polymeric materials are used, it is preferable to use a mold to manufacture each of the halves. Moreover, in some embodiments, more than one molded piece may be used to form an individual half, with the various pieces being joined together by bonding or mechanical means to form a half. Alternately, as is known in the art, the individual halves can be formed through machining processes performed on larger blocks of the raw materials.

Figure 24:
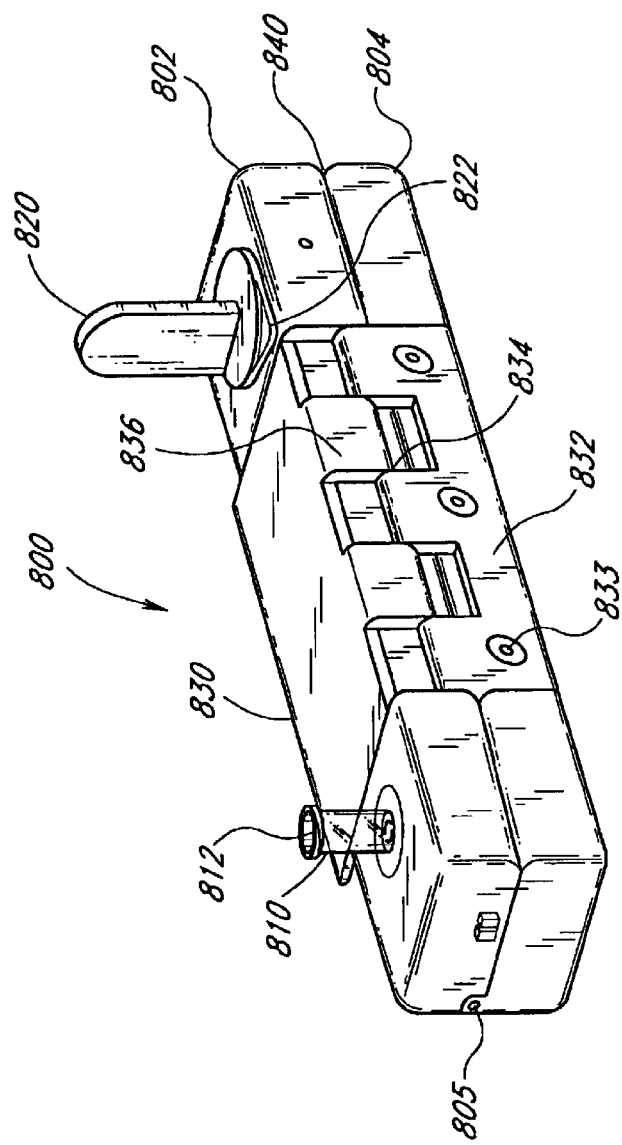
FIG. 24 is a perspective view of an alternative embodiment of an inflation adaptor used to manipulate the low profile valve in a preferred aspect of the present invention.
Figure 25:
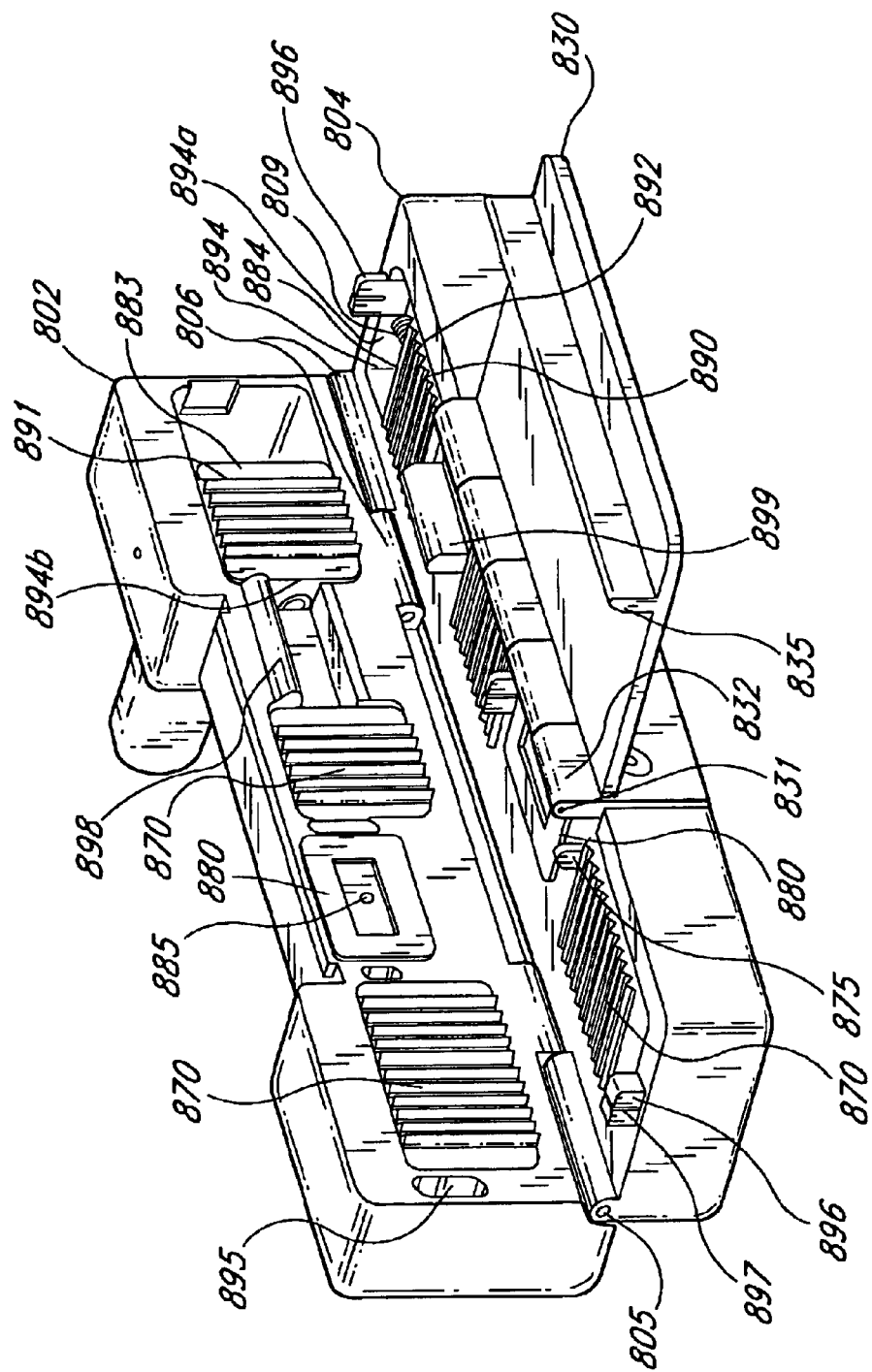
FIG. 25 is a perspective view of the interior of the inflation adaptor of FIG. 24.

Halves 802 and 804 are attached to one another by hinges 806 positioned on one of the lateral edges of each half, through which a joining pin 805 is inserted, such that halves 802 and 804 may be opened or closed in a clam shell manner as depicted in FIGS. 24 and 25. Preferably, the cross-sectional angle formed by halves 802 and 804 in the open position, as shown in FIG. 25, is 90° or greater, and more preferably from 120°–180°, to facilitate insertion of a catheter into adaptor 800.

As shown in FIGS. 24 and 25, a plate 832 is secured to the front portion of housing half 804 by three screws 833. Plate 832 is provided with two or more pin receptacles 834. A cam latch 830 is mounted on plate 832 and is secured thereto by pin 831 which runs through pin receptacles 834 and a corresponding cam latch pin receptacles 836, to form a hinge between cam latch 830 and plate 832. Cam latch 830 and plate 832 may be made from any of the same variety of materials as housing halves 802 and 804, and for any particular embodiment, are preferably made of identical materials, although combinations of materials may also be used. Also, as is appreciated by those of skill in the art, the corresponding hinge structure provided by plate 832 and cam latch 830 may also be achieved by many other methods. For example, plate 832 may be integrally molded with housing half 804 at the time of manufacture as a single piece, thereby eliminating the need for screws 833, but with cam latch 830 mounted thereon as described above.

Cam latch 830 is designed to secure halves 802 and 804 together when adaptor 800 is in use, to assist in the creation of an the inflation seal as described above. Advantageously, by placing cam latch on half 804 as shown, the adaptor interior is more accessible to the clinician during a procedure, and it is easier for the clinician to insert catheters into adaptor 800. Cam latch 830 also serves the important function of preventing accidental opening of the adaptor 800 during use. An important feature of cam latch 830 is the manner in which it cooperates with housing half 802 to create a releasable locking mechanism which applies great force to halves 802 and 804 upon closing, while at the same time using the principles of mechanical advantage to minimize the force the user must exert to close cam latch 830. This is achieved by providing latch 830 with a cammed surface 838 and also providing the front edge of housing half 802 with a rounded lip 837 to accept cammed surface 838, as shown in cross-sectional schematic form in FIGS. 27A–27C.

Figure 27A:
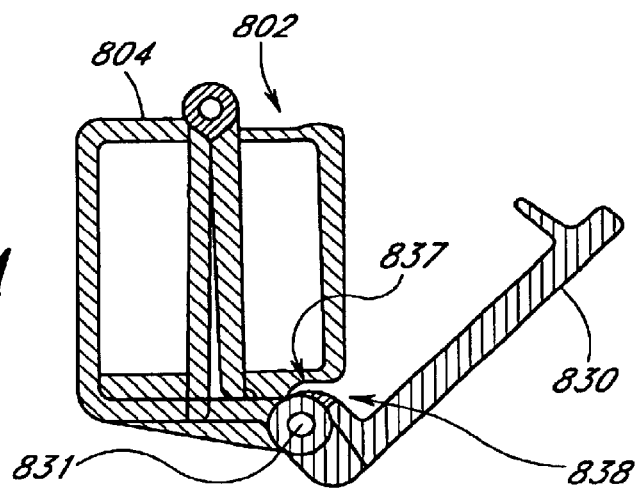
FIGS. 27A–27C are schematic cross-sectional views of the adaptor of FIG. 24 which illustrate the cam locking door mechanism which provides mechanical advantage to the adaptor locking latch.
Figure 27B:
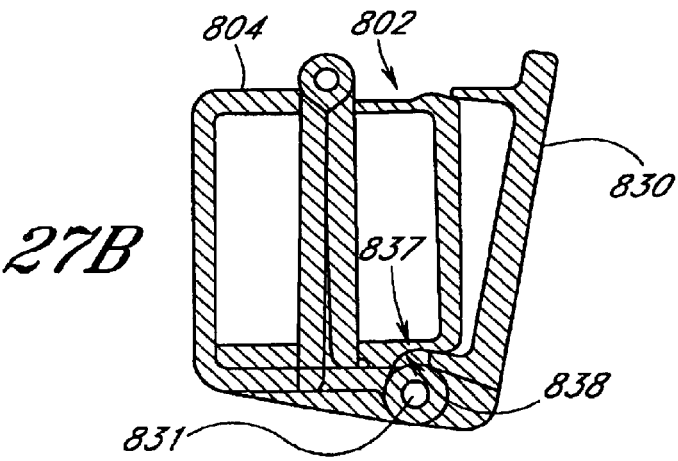
Figure 27C:
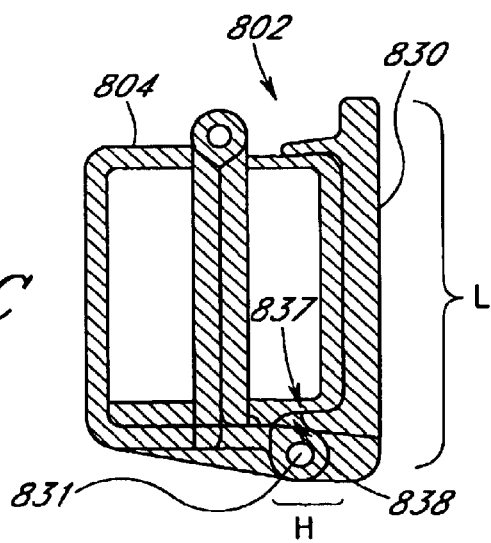

Referring to FIG. 27A, halves 802 and 804 have been brought together, with cam latch 830 in its open position. As cam latch 830 begins to be closed, as shown in FIG. 27B, cammed surface 838 contacts rounded lip 837 and exerts a closing force thereon. Upon further closing, and to the fully closed position shown in FIG. 27C, cam latch 830 acts as a lever, with the closing force between cammed surface 838 and lip 837 being a function of the force of exerted by the user, the length of the lever (length of cam latch door), and the height of the cam surface, as defined by the following well known mathematical equation:

$$F_u = F_c \frac{H}{L}$$

$F_u$ = User applied force
$F_c$ = Closing force
$L$ = length of lever (width of door)
$H$ = height of cam However, as can be appreciated, because the lever length, which in the adaptor embodiment is the length of cam latch 830 in its closing direction, is much greater than the height of the cam created by surface 838 and lip 837, the closing force exerted is always greater than the force the user exerts on cam latch 830. Thus, very tight seals may easily be created by the clinician when the device is used.

Cam latch 830 is also preferably provided with a shelf 835 to secure halves 802 and 804 together. Shelf 835 is positioned on latch 830 at a point such that when latch 830 is in its closed position, shelf 835 firmly contacts housing half 802 along the side bearing hinges 806. Preferably, shelf 835 has an angled leading edge to facilitate closing of latch 830.

A gap 840 separates first half 802 from second half 804 when the halves are closed and latch 830 is secured. Gap 840 is of sufficient width to accept the proximal end of a catheter having the low profile valve, as described in detail above, without crimping the catheter to impair its function. A fitting 810 is positioned on half 802, to create an inflation passageway 812 which terminates in opening 885 on the interior surface of first half 802. Fitting 810 is preferably a standard luer connector which may be attached to a variety of existing external pressurized fluid sources, although other types of fittings, such as tubings, quick connects, and Y-site connections, may be easily substituted for a luer fitting.

A seal comprising a pair of gaskets 880 is positioned around opening 885 on the interior surfaces of halves 802 and 804. Gaskets 880 are in alignment, such that when halves 802 and 804 are brought together and secured by cam latch 830, a fluid tight inflation chamber is created within the interior region defined by gaskets 880. The fluid tight inflation chamber is in fluid communication with fitting 810 via inflation passageway 812, so that a pressurized inflation fluid may be introduced into the fluid tight inflation chamber by attaching an external pressurized fluid source to fitting 810. Gaskets 880 are preferably formed of resilient materials, such as silicone, C-Flex (™) and Pebax (™) or Kraton (™), silicone, and other elastomeric materials, so that gaskets 880 may form-fit over a catheter tubular body which extends across the lateral edges of gaskets 880, to create the fluid tight chamber.

An actuator 820 is positioned on the external surface of half 802. In the embodiment illustrated in FIGS. 24–26B, actuator 820 is a rotatable knob controlling a cam which operates a sliding panel 883 on the interior surface of half 802. As will be appreciated by those of skill in the art, however, a great many different actuating structures other than rotatable knobs and sliding panels may be used to achieve the movement of the catheter sealing members described herein. Furthermore, where catheter valves require rotational movement, such as those of FIGS. 20 and 21, rotational actuating mechanisms may be provided as well.

Figure 26A:
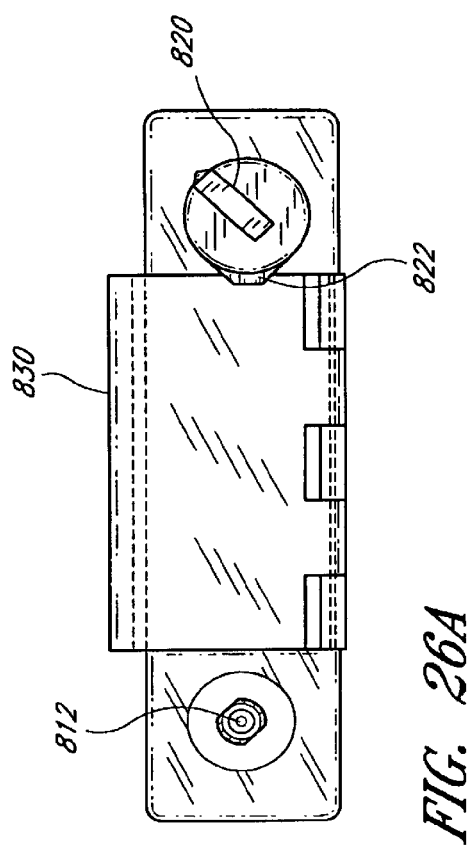
FIGS. 26A and 26B are top views of the inflation adaptor of FIGS. 24 and 25, illustrating the latch locking mechanism.
Figure 26B:
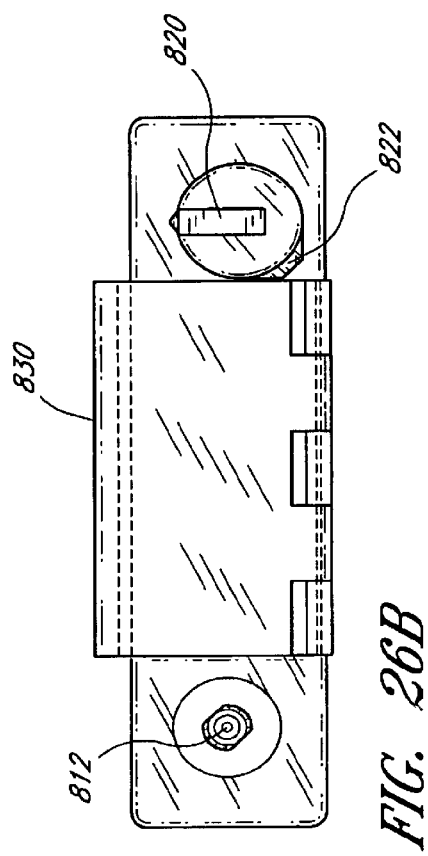

Sliding panel 883 moves back and forth along a line which bisects opening 885. When actuator 820 is moved to a first position, shown in FIG. 26A, sliding panel 883 moves away from opening 885 along this line. When actuator 820 is moved to a second position, as shown in FIG. 26B, sliding panel 883 moves toward opening 885 along the same line. A corresponding sliding panel 884 is positioned on half 804, such that panels 883 and 884 are aligned and move together when halves 802 and 804 are closed and the position of actuator 820 is changed.

In actual clinical practice, the movement of panels 883 and 884 results in the opening and closing of a catheter valve placed within adaptor 800. When actuator 820 is moved to the position shown in FIG. 26A, panels 883 and 884 move away from opening 885. This would result in the opening of the valve described in connection with FIGS. 9–13, as the sealer portion of the valve would be positioned proximally of the access port to establish a fluid pathway between the access port and the inflatable balloon at the distal end of the catheter. Conversely, when actuator 820 is moved to the position shown in FIG. 26B, panels 883 and 884 move toward opening 885. This would result in the closing of the valve, as the sealer portion of the valve would be positioned distally of the access port, thereby preventing substantially all fluid flow between the access port and those portions of the catheter distal to the sealer portion. Preferably, detents (not shown) are provided on the actuator camming mechanism to provide the user with tactile and audible feedback when the panels are nearest or farthest from opening 885 (i.e., catheter valve is closed or open, respectively).

Adaptor 800 is also preferably provided with a safety lock, to prevent accidental opening when the adaptor is being used and the catheter valve is open. As shown in FIGS. 26A and 26B, this may be achieved by providing an extending flanged portion 822 to actuator knob 820. When actuator knob 820 is in the valve open position, as shown in FIG. 26A, extending flange 822 extends over latch 830, preventing the latch from being opened. In the valve closed position, as shown in FIG. 26B, flange 821 is rotated away from latch 830, which may then be opened.

Panels 883 and 884 each have a roughened surface 890, to facilitate the frictional engagement of panels 883 and 884 and their coordinated travel with the moving portions of the low profile valve. Panels 883 and 884 may be made from any of a variety of polymeric or metallic materials, but must possess sufficient frictional force to engage and move the catheter sealing member without slippage. Consequently, depending on the type of catheter used, those of skill in the art may desire to select different materials for panels 883 and 884 to maximize the frictional forces between the panels and their intended use catheter. In a preferred embodiment, in which panels 883 and 884 are to engage a catheter sealing member made from stainless steel, panels 883 and 884 are both made of Kraton 90A (™), and roughened surface 890 comprises teeth 891 and grooves 892 formed on each of panels 883 and 884. The teeth 891 and grooves 892 cooperate, to permit the teeth of one panel to fit into the grooves of the opposite panel when the adaptor is closed. Furthermore, alternative cooperating structure, such as dimples and ridges, may also be used to coordinate travel of panels 883 and 884.

One problem that has been recognized with low profile valves is the phenomenon of plug walk-out. That is, after the valve has been placed in its closed position, with the sealer portion of the sealing member distal to the inflation access port, and the adaptor removed, the internal forces on the sealing member tend to cause very small portions of the sealing member to be pushed out of the catheter proximal end. Plug walk out is undesirable as it has an adverse impact on the ability of the sealed catheter to act as a guidewire for other devices. It has been found, however, the plug walk out can be minimized or eliminated if the sealing member is initially "overdriven", or forced slightly further in the catheter, during the sealing step.

Advantageously, adaptor 800 is provided with an overdrive system to overdrive a sealing member into a catheter. Referring to FIG. 25, panel 884 travels back and forth within housing recess 894 along a which bisects opening 885, as described above. A spring 809 is mounted in recess 894 and is attached to the wall of recess 894 and panel 884. Spring 809 is biased so as to push panel 884 toward opening 885, and forces panel 884 against the wall of recess 894 which is opposite to that which spring 809 is attached.

Figure 28A:
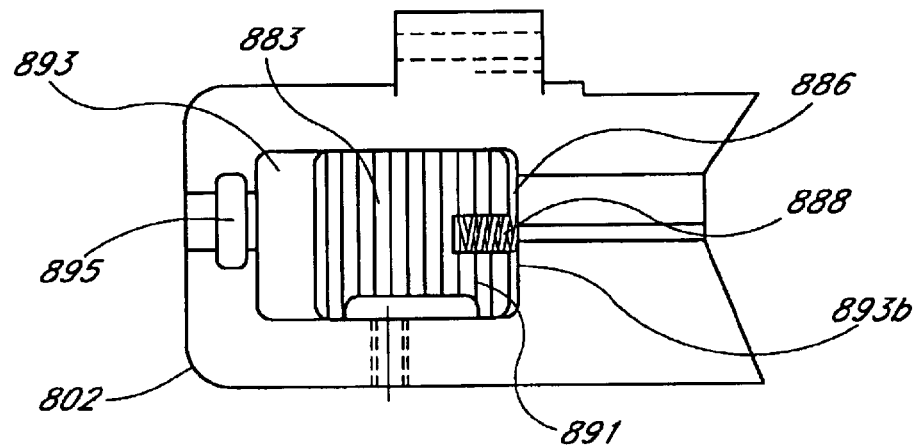
FIGS. 28A–28C are close-up views of an embodiment of the adaptor having a sliding top panel biased by a spring mechanism.
Figure 28B:
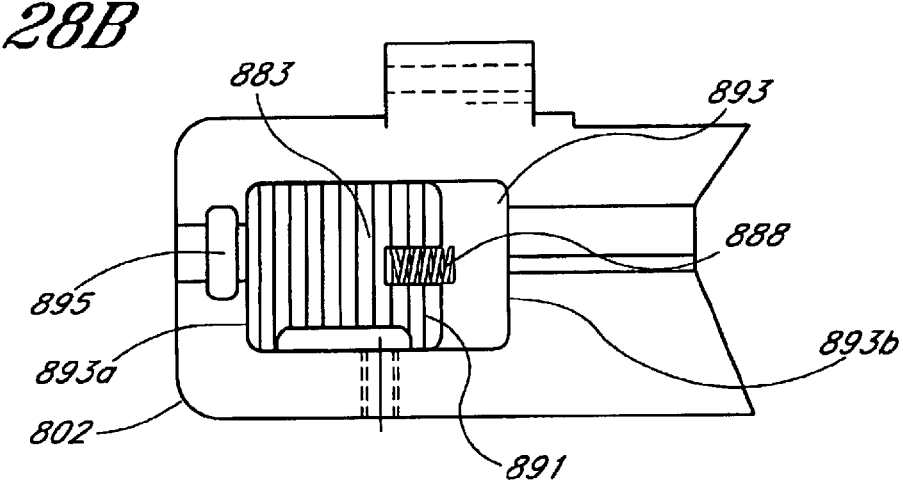
Figure 28C:
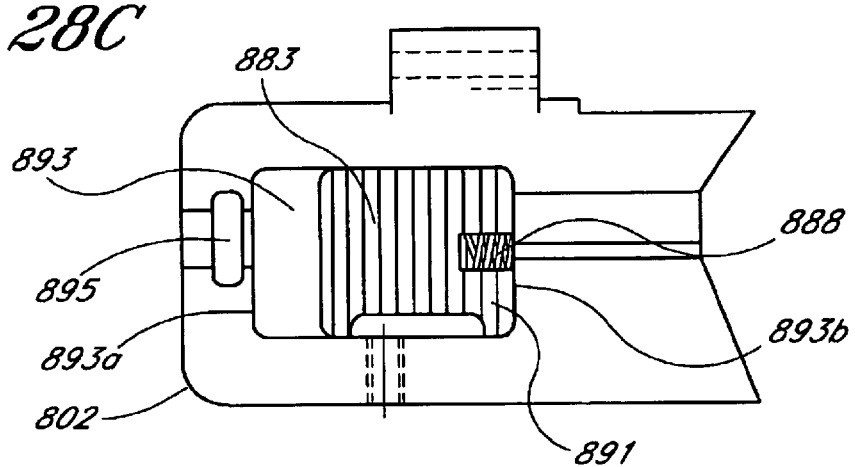

Referring to FIGS. 28A–28C, there is shown the top portion of half 802 containing panel 883. Panel 883 resides in housing recess 893, and travels back and forth along a line which bisects opening 885, as described above. The movement of panel 883 is controlled by actuator 820, as described above. An expanded spring 888 is attached to panel 883, as shown in FIGS. 28A–28C. Spring 888 has a strength which exceeds that of lower spring 809. In the adaptor open position, as shown in FIG. 25, expanded spring 888 contacts the wall of recess 893, and pushes panel 883 away from the recess wall to create an overdrive gap 886, as shown in FIG. 28A.

When a catheter with a valve in a closed position is loaded into half 804, and halves 802 and 804 are closed and latched, the teeth 891 of panel 883 contact the grooves of panel 884. The superior spring force of spring 888 then forces spring 809 to compress a small amount, such that panel 884 no longer is forced against the recess wall, and now has an overdrive gap (not shown) approximately equal to overdrive gap 886. The actuator may then be engaged to drive panels 883 and 884 away from opening 885 toward recess walls 893a and 894a, respectively, thereby opening the valve mechanism. The inflatable balloon on the catheter may then be inflated as described above.

Upon closure of the valve, by rotating actuator 820 in the opposite direction, panels 883 and 884 are moved toward opening 885 until the sealer portion of the sealing member is distal to the catheter inflation access port. Overdrive of the sealing member is then achieved when actuator 820 is adjusted so that panels 883 and 884 are forced against recess walls 893b and 894b, as shown for panel 883 in FIG. 28C. That is, the force of actuator 820 overcomes the force of spring 888, and drives the sealing member into the catheter by a distance farther than it initially resided before the valve was opened, the distance being approximately equal to the width of gap 886. It has been found that by overdriving the sealing member to a closed position further than its initial closed position compensates for plug walk-out. Preferably, the sealing member is overdriven by a distance of about 0.020 inches.

Alternative overdrive mechanisms may be used for other adaptor embodiments. For example, rather than mounting spring 888 on panel 883, the spring might be mounted in a slot wall 893b, with a plunger (not shown) attached to panel 883 and aligned with the spring. In its unforced state, the spring would exert force on the plunger, pushing panel 883 away from wall 893a to create overdrive gap 896. However, as before, the actuator mechanism 820 could be used to overcome the spring force in the valve closing cycle, thereby creating the overdrive. Numerous other overdrive mechanisms may also be employed, as will be appreciated by those of skill in the art.

As illustrated in FIG. 25, adaptor 800 is also provided with immovable pads 870 on both halves 802 and 804. Pads 870 function to secure the catheter within adaptor 800 when it is closed, and to prevent movement of the catheter during valve opening and valve closing procedures. Accordingly, the material used for pads 870 is selected to have a high degree of frictional force with respect to the surface of the catheter body to which pads 870 will contact. A wide variety of polymeric and metallic materials are thus suitable to form pads 870 such as Kraton (™), C-Flex (™) or Pebax (™). In one embodiment, pads 870 are integrally molded with halves 802 and 804 out of medical grade polycarbonate, and are intended to contact a catheter tubular body formed from nitinol.

It is also preferred that half 804 be provided with guiding means to facilitate correct positioning of the catheter into the adaptor. For the embodiment illustrated in FIG. 25, these guiding means consist of two or more clips 896 to facilitate positioning of a catheter into the adaptor. Clips 896 are provided with grooves 897 in which the catheter is inserted and secured prior to closure of adaptor 800. Clips 896 may be formed of any material flexible enough to be capable of releasably securing the catheters to be used in adaptor 800. In one preferred embodiment, clips 896 are formed of C-Flex 70A (™). On half 802, and aligned with clips 896, there are provided recesses 895, to accept clips 896 when halves 802 and 804 are brought together and closed. Preferably, alignment indicia on the catheters to be used with adaptor 800 coincide with the spacing of clips 896, so that by placing the catheter portion bearing the indicia directly in clips 896, the catheter is properly inserted in the adaptor with its inflation access port contained in the fluid tight inflation chamber created by gaskets 880 upon closure of adaptor 800. A projecting ridge 875 may also be provided to facilitate placement of the catheter, and direct its orientation during placement in the adaptor so that alignment is proper.

Alternately, other guiding means may be used as well. For example, clips 896 may comprise one or more magnetic elements which cooperate with gold-plated stainless steel rings (or other plated ferromagnetic substances) incorporated into the catheter tubular body to guide the catheter into the correct alignment position.

In one preferred embodiment, as shown in FIG. 25, halves 802 and 804 are also provided with projecting shelves 898 and 899, respectively, which come together when halves 802 and 804 are closed to form a slot therebetween in which the catheter resides. Advantageously, the slot created by shelves 898 and 899 acts to provide reinforcement to a catheter used in adaptor 800 during the valve opening and closing procedures, and helps to prevent buckling or kinking of the catheter tubular body when panels 883 and 884 are moved to open or close the catheter valve.

In clinical practice, there is a direct correlation between the distance that panel 884 moves and the distance moved by the sealer portion of a catheter valve when adaptor 800 is used. Consequently, a controlled and known movement of panel 884 over a set direction and distance results in a movement of the valve sealer portion in the same direction and for substantially the same distance. Thus, with a controlled movement adaptor such as adaptor 800, there is no need to require a catheter having positive cooperating stops to prevent removal of the sealer portion from the catheter, as was described for the catheter of FIGS. 9–13. The adaptor itself prevents accidental withdrawal of the sealer portion from the catheter, by precisely controlling the movement of the sealer portion within the catheter.

Accordingly, in one preferred embodiment, adaptor 800 is used with catheter 900, which lacks positive cooperating stops, and is depicted in FIGS. 29 and 30. Catheter 900 has a tubular body 918 and inflatable balloon (not shown) as described above. Catheter 900 may be formed of materials and methods as described above, and may have structural aspects identical to those described previously, except where otherwise noted.

Catheter 900 has a proximal end 912, and a distal end (not shown) to which is mounted an inflatable balloon. A central lumen 940 extends within tubular body 918 between the proximal and distal ends. An opening 923 to lumen 940 is present at the proximal end 912 of catheter 900. A side-access port 922 in fluid communication with lumen 940 is provided on tubular body 918.

A sealing member 930 is inserted into lumen 940 through central lumen opening 923. Sealing member 930 has a first region 935 which has an outer diameter substantially the same as the outer diameter of the proximal end 912 of catheter tubular body. Region 935 has a taper 934, reducing in diameter to a second region 933 which has an outer diameter less than the inner diameter of lumen 940. Region 933 tapers over length 931 to form a plug mandrel wire 932. As a consequence, region 933 and plug mandrel wire 932 are slidably insertable into the proximal opening 923 of catheter 900 and may freely move within lumen 940. In one preferred embodiment, region 935 has an outer diameter of about 0.013 inches, region 933 has an outer diameter of about 0.0086 inches, and plug mandrel wire has a diameter of about 0.005 inches, with region 933 and plug mandrel wire 932 being inserted into a catheter having a central lumen 940 with an inner diameter of about 0.009 inches.

The length of sealing member region 935 extending proximally of catheter 900 may vary in length depending upon the intended use environment. For example, where catheter 900 is to be used as a guide for other catheters in an "over-the-wire" embodiment, it is preferred that the total length of catheter 900 and sealing member region 935 be about 300 centimeters. Alternately, where catheter 900 is to be used in a single operator or rapid exchange embodiment, it is preferred that the total length of catheter 900 and region 935 be about 180 centimeters. Accordingly, with a known catheter length and use environment, an appropriate length for region 935 may be chosen.

The elements of sealing member 930 may be formed of materials and by methods as described previously. For example, regions 935 and 933 and plug mandrel wire 932 may all be made out of metals such a stainless steel. Alternately, combinations of materials may be used as well. For example, in some applications it may be desirable to manufacture regions 935 and 933 out of stainless steel, while manufacturing plug mandrel wire 932 out nitinol. Furthermore, the various sealing member regions may be made from a single metal wire strand coined at various points to achieve the desired dimensional tolerances, or multiple segments may be joined together to form sealing member 930.

Where multiple segments are joined, region 935, region 933, and plug mandrel wire 932 are attached to one another by any suitable means of bonding metal to metal, such as soldering, brazing, adhesives and the like. In one preferred embodiment, cyanoacrylate adhesives are used to adhere these various parts of sealing member 930 to one another.

As illustrated in FIGS. 29 and 30, the outer diameter of sealing member region 933 is less than the inner diameter of lumen 940, such that region 933 is slidably insertable into lumen 940. In addition, the outer diameters of the tapered portions 931 and wire 932 are also small enough such that they too are slidably insertable in lumen 940. However, the outer diameter of region 935 is greater than the inner diameter 940, and thus only a small portion of tapered portion 934 of sealing member 930 between region 935 and region 933 is insertable into lumen 940 through opening 923. Advantageously, this provides for a snug interference fit when sealing member 930 is fully inserted into catheter 900. This interference fit provides a frictional force which counteracts the tendency of the pressurized fluids and internal wire flexing in the catheter to push sealing member 930 out of opening 923.

As illustrated in FIGS. 29 and 30, sealing member 930 has movement-force increasing structure which increases the force required to move sealing member 930 within lumen 940. The movement-force increasing structure consists of waves 938a and 938b formed in wire 932 near its distal end. Waves 938a and 938b contact the inner surface of lumen 940, thereby increasing the frictional force which must be overcome to move wire 932 within lumen 940. In one preferred embodiment, where wire 932 is made of nitinol and has an outer diameter of about 0.005 inches, and is inserted into a nitinol catheter which has an inner lumen 940 with a diameter of about 0.090 inches, waves are formed on wire 932 for 1½ cycles with an amplitude of about 0.016 inches to increase the valve-opening movement force.

A lumen sealer portion 936 is coaxially and fixedly mounted on wire 932. Sealer portion 936 forms a fluid tight seal with the outer diameter of wire 932 and the inner diameter of lumen 940, such that fluid introduced into lumen 940 through side-access port 922 is prevented from flowing past sealer portion 936 when sealer portion 936 is inserted into lumen 940 distally of side-access port 922. Sealer portion 936 forms the fluid tight seal by firmly contacting the entire inner circumference of a section of lumen 940 along a substantial portion of the length of sealer portion 936, and may be formed of materials and by methods as previously described.

As shown in FIG. 29, sealer portion 936 is positioned proximally of side-access opening 922, so that an unrestricted fluid passageway exists between port 922 and the inflatable balloon at the distal end of catheter 900. This is the valve open position described above. In this position, region 933 is shown partially withdrawn from opening 923. Referring to FIG. 30, sealer portion 936 is positioned distally of port 922, so that fluid flow between port 922 and the inflatable balloon at the distal end of catheter 900 are substantially blocked. This is the valve closed position described above.

Catheter 900 is changed from the valve open position to the valve closed position by the movement of sealing member 930 and its various components. Preferably, the exact length of movement needed to change catheter 900 from the valve closed to the valve open position is built into the movement function of the adaptor used to manipulate sealing member 930 thereby opening and closing the catheter valve. In this regard, it is preferred that catheter 900 be used with an adaptor such as adaptor 800, which provides for such controlled precise movement.

The "stroke-length", or overall movement in one dimension, of sealing member 930 required to open or close the valve may be varied depending upon the catheter requirements. When relying upon the inflation adaptor to control movement, however, it is important that the movement of the controlling elements of the adaptor be coordinated with those of sealing member 930. With respect to adaptor 800, this is accomplished by selecting a recess 893 dimension which precisely defines the distance that sealing member 930 is to travel to achieve the valve open and valve closed positions, without accidentally removing sealing member 930 from opening 923. In one embodiment, where access port 922 is positioned 36 mm from opening 923, a stroke length of 5.5 mm was found to be suitable.

III. Expansion Members

The expansion members discussed herein include braids, coils, ribs, ribbon-like structures, slotted tubes, and filter-like meshes. These expansion members may be partially covered or completely surrounded by a membrane or other covering to provide occlusion or sealing of the vessel. As used herein, "occlusion" or "sealing", and the like, mean partial or complete blockage of fluid flow in a vascular segment, as it is sometimes preferable to allow perfusion. Moreover, such expansion members may be deployed by various mechanical means, electrical means or thermomechanical means, etc., as described herein. Expansion members that are deployed mechanically are preferably "spring-like" in nature, i.e. they are preferably resilient to facilitate their deployment or retraction.

A. Catheter Apparatuses and Self-expanding Braids

One embodiment of a catheter apparatus incorporating the present invention for treating occluded vessels is shown in FIGS. 31 and 32. As shown therein, the catheter apparatus 1651 consists of a flexible elongate member 1652 which is provided with proximal and distal extremities 1653 and 1654. A conventional adaptor 1656 is mounted on the proximal extremity and is provided with a Touhy-Borst fitting 1657 which is in communication with a large central lumen 1658 extending from the proximal extremity 1653 to the distal extremity 1654. An aspiration fitting 1661 is provided on the adaptor 1656 as well as an irrigation fitting 1662, both of which are in communication with the central lumen 1658. However, it should be appreciated that if desired, separate lumens can be provided in the flexible elongate member 652 for both of the fittings 1661 and 1662.

Self-expanding sealing mechanism 1666 is mounted on the distal extremity 1654. This self-expanding sealing mechanism 1666 can take any suitable form. For example, as shown it can consist of a braided structure 1667 formed of a suitable shape memory material such as a nickel titanium alloy that will attempt to expand to a predetermined shape memory. Other than shape memory materials, other materials such as stainless steel, Elgiloy™, titanium or other materials can be utilized in the braid 1667 as long as they have the capability of expanding when the self-expanding seal mechanism is released. Also it should be appreciated that the self-expanding seal mechanism 1666 can be comprised of an absorbent material which when it absorbs saline or blood expands to form a seal. Such seals can be readily accomplished because it is only necessary to form a seal of approximately 1.5 psi to prevent small particles from moving downstream.

In order to prevent abrasion of a vessel, it is desirable to cover the braided structure 1667 with a covering 1668 of a suitable material such as a polymer or a biocompatible coating which extends over the braided structure 1667 and which moves with the braided structure 1667 as it expands and contracts. The polymer can be of a suitable material such as silicone, C-flex, polyethylene or PET which would form a good sealing engagement with the wall of the artery. The covering 1668 may be perforated to allow perfusion.

A mechanism is provided for compressing the self-expanding sealing mechanism 1666 so that the apparatus can be inserted into the vessel 1481 and consists of an elongate sleeve 1771 having proximal and distal extremities 1772 and 1773 and a bore 1774 extending from the proximal extremity 1772 to the distal extremity 1773. A collar 1776 is mounted on the proximal extremity 1772 of the sleeve 1771 and is positioned near the adaptor 1656. The collar 1776 serves as a mechanism for retracting the sleeve as shown in FIG. 32 to uncover the self-expanding sealing mechanism 1666 after the catheter has been deployed to permit the self-expanding sealing mechanism 1666 to expand and form a seal with the arterial vessel adjacent the stenosis to be treated.

Another embodiment of a catheter apparatus for treating occluded vessels incorporating the present invention is shown in FIGS. 33 and 34. As shown therein, the apparatus 1781 consists of a guiding catheter 1782 having proximal and distal extremities 1783 and 1784. As shown, the distal extremity 1784 is provided with a pre-formed bend of a conventional type. A conventional attachment 1786 is mounted on the proximal extremity 1783. Self-expanding seal mechanism 1791 is mounted on the distal extremity 1784 and is of the type hereinbefore described in connection with the embodiments shown in FIGS. 31 and 32. A sleeve 1796 similar to the sleeve 1771 of the previous embodiment is provided in the present embodiment for encasing the self-expanding seal mechanism 1791 and for releasing the same after it has been disposed in an appropriate position within a vessel adjacent the occlusion to be treated. Thus, a sleeve 1796 is provided having proximal and distal extremities 1797 and 1798 and having a bore 1799 extending from the proximal extremity to the distal extremity which is sized so that it can receive the guide catheter 1782. It is provided with a collar 1801 on its proximal extremity which is adapted to be disposed outside the patient and which is adapted to be grasped by the physician for pulling the sleeve 1796 proximally to uncover the self-expanding seal 1791 after the apparatus has been deployed to permit the self-expansion of the sealing mechanism 1791 to form a seal with the vessel wall as shown in FIG. 34.

In accordance with the hereinbefore described descriptions, it is apparent that the apparatus can be readily deployed and serve the same function as the main catheter. To accomplish this, the assembly 1781 can be introduced into the femoral artery and the distal extremity advanced into the desired location in the arterial vessel. After it has been properly positioned, the physician can retract the sleeve 1796 to permit the self-expanding seal mechanism 1791 to expand and to form a seal with the wall of the arterial vessel to occlude the arterial vessel and interrupt the flow of blood in the vessel to provide a working space distal of the occlusion formed. This prevents small particles which may thereafter be dislodged from moving downstream. Since a central lumen is available, the therapeutic procedures hereinbefore described can be employed with the catheter apparatus shown in FIGS. 31–34.

Although the self-expanding sealing mechanism 1666 (1791) can be deployed by retracting the sleeve 1771 (1796) as previously described, the sealing mechanism can also be deployed by pushing the flexible elongate member 1652 (guiding catheter 1782) through the sleeve so that the sealing mechanism can expand. This may be the preferred way of deploying the sealing mechanism 1666 (1791), if there is little clearance between the apparatus 1651 (1781) and the vessel within which the apparatus resides, to reduce the risk of damaging the patient's vessel. As discussed below in connection with subsequent figures, the sealing mechanism 1666 (1791) may alternatively comprise members such as a coil, a ribbon-like structure, a slotted tube, or a filter-like mesh. In each case, the sealing mechanism expands to partially or completely occlude the vessel in question, or alternatively, to anchor an intravascular device to the vessel.

Furthermore, although the embodiments described in FIGS. 31–34 are illustrated with an adaptor 1656 or attachment 1786, these may be easily removed to allow an exchange of catheters over the member 1652 or 1782. Such an embodiment is shown in FIG. 35. When retracting the sleeve 1796 to deploy the sealing mechanism 1791, the sleeve 1796 may remain on the member 1782, or may be completely removed as shown in FIG. 36. By removing the sleeve completely, the catheters exchanged over the guiding member can have a lower profile to allow insertion into smaller vessels.

B. Alternative Self-expanding Members

Figure 37:
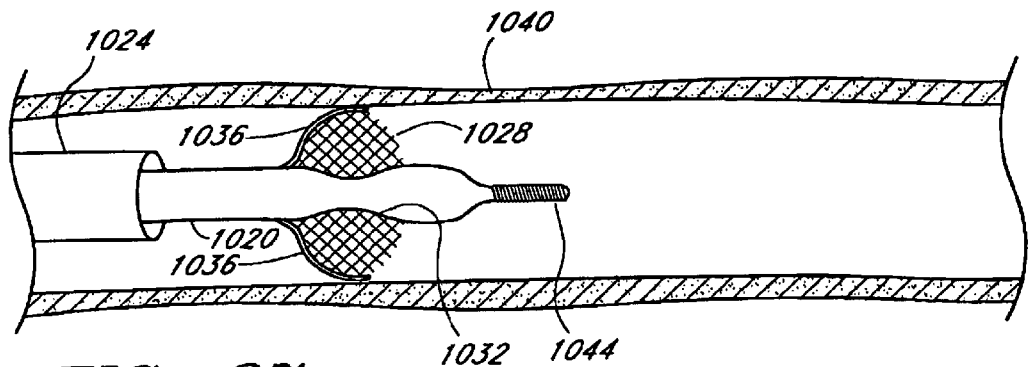
FIG. 37 is a schematic, longitudinal cross sectional view of an embodiment in which a membrane only partially surrounds a braid used as the expansion member.
Figure 38A:
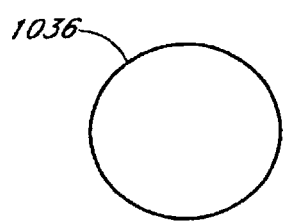
FIGS. 38A and 38B show end views of unperforated and perforated membranes, respectively.
Figure 38B:
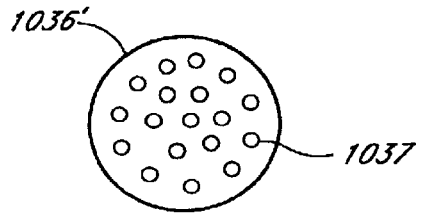

Another embodiment using a braided structure is shown schematically in FIG. 37, in which a flexible elongate member 1020 is disposed within a second elongate member 1024 such as a hypotube. A self expanding mechanism 1028 such as a braided structure is secured to the distal end of the elongate member 1020, preferably within an indentation 1032 of member 1020. The braided structure 1028 is only partially encapsulated by a preferably elastomeric membrane 1036 that makes a seal with the patient's vessel 1040. (Alternatively, a coating such as a polymeric coating may be used in place of the membranes disclosed herein.) In this and the other embodiments, adhesive may be used to secure the self-expanding mechanism 1028 and the membrane 1036 to the elongate member 1020. In the embodiment of FIG. 37, the braided structure 1028 and membrane 1036 are designed to be asymmetrical, with more material being concentrated at the proximal side of the structure 1028. The braids of the embodiments disclosed herein may be stainless steel 304 or 400, superelastic or heat activated Nitinol, an iron base shape memory alloy, or a polymer base, such as polyethylene or polypropylene. They may be constructed, for example, by using standard equipment such as a braider.

Although the embodiment of FIG. 37 shows the flexible elongate member 1020 connected to a guidewire tip 1044, other technologies for guiding the device through the patient's vessel 1040 may be used in this and the other embodiments, such as a guidewire (either over the wire or single operator) or the exchange catheter method, as is well known in the art. Also, although not explicitly shown in the embodiment of FIG. 37 and the other embodiments herein, these embodiments may include lumens, aspiration and irrigation fittings, and collars like those illustrated in FIGS. 31–34.

The membrane 1036 is preferably impervious to the flow of blood (FIG. 38A) for those applications not requiring perfusion, although a perforated membrane 1036' (FIG. 38B) having numerous holes 1037 therein may be used in other applications to allow the passage of blood. The holes 1037 are preferably greater than 10 microns in diameter and may be up to 80 microns or more in diameter to permit the passage of blood cells (nominally 6–10 microns in diameter) through the membrane 1036' while blocking larger particulates such as emboli. Likewise, a perforated membrane 1036' may be used in the other embodiments disclosed herein. Antithrombogenic coatings can be used (e.g., heparin) to prevent thrombosis formation.

Figure 39:
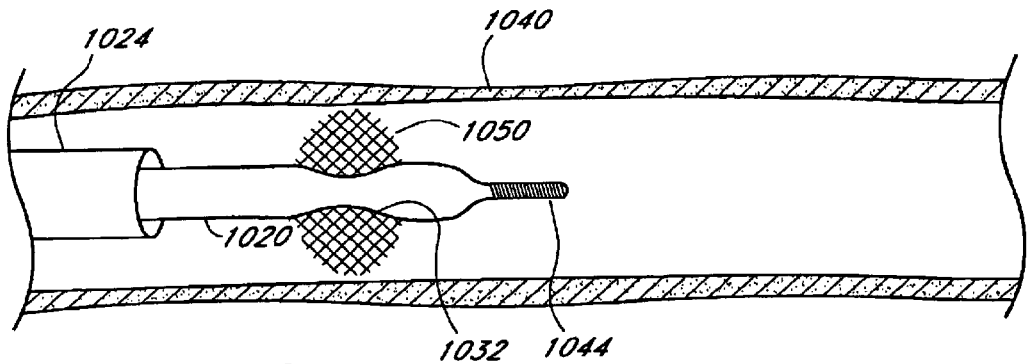
FIG. 39 is a schematic, longitudinal cross sectional view of an embodiment in which a braid without a membrane is used.

FIG. 39 shows an embodiment in which a braided structure 1050 is not enclosed by a membrane. When the braided structure 1050 comprises, for example, a diamond mesh pattern in which adjacent wires are separated by about 10–80 microns, the braided structure permits the passage of red blood cells, while blocking the flow of matter that may be undesirable, e.g., emboli or other particulates that may be formed or dislodged during medical procedures. Thus, this embodiment is well suited for applications for which perfusion is required.

Figure 40:
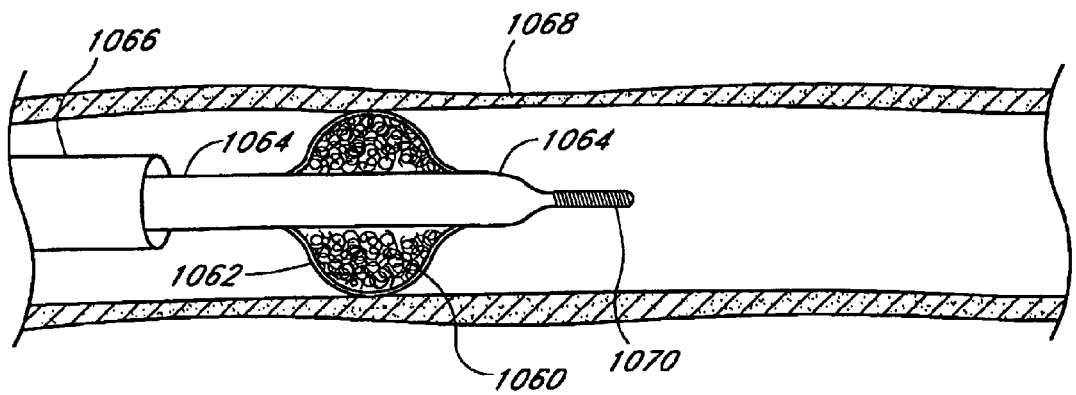
FIG. 40 is a schematic, longitudinal cross sectional view of an embodiment in which a filter-like mesh is used as the expansion member.
Figure 41:
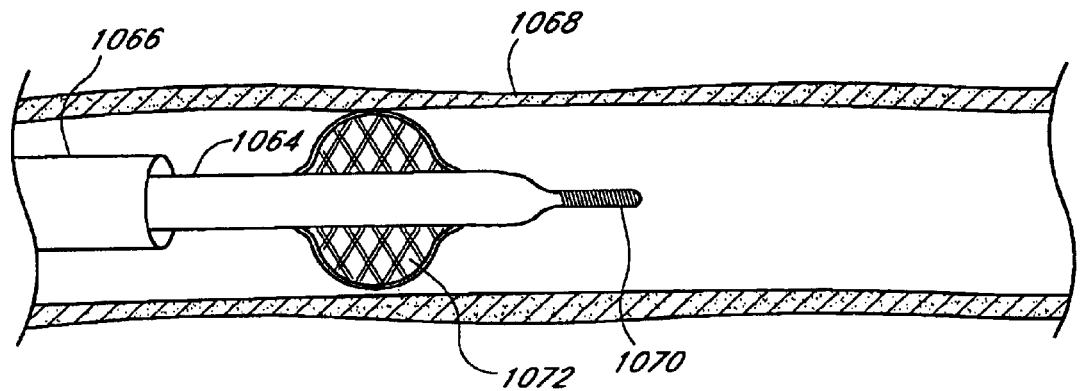
FIG. 41 is a schematic, longitudinal cross sectional view of an embodiment in which a slotted tube is used as the expansion member.
Figure 42:
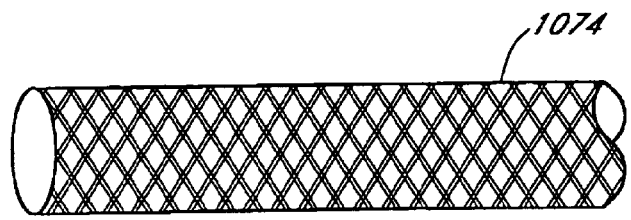
FIG. 42 is a perspective view of the slotted tube used in the embodiment of FIG. 41.

Alternative self-expanding media are shown in FIGS. 40 and 41. In FIGS. 40 and 41, a self-expanding filter-like mesh 1060 and a self-expanding slotted tube 1072, respectively, are surrounded by a membrane 1062 that is preferably elastomeric. The filter-like mesh 1060 (or slotted tube 1072) and membrane 1062 are bonded or otherwise secured to a flexible elongate member 1064, e.g., to an indentation therein. As with the other self-expanding media disclosed herein, the filter-like mesh 1060 (or slotted tube 1072) expands from its unexpanded state when the flexible elongate member 1064 is pushed through a second elongate member 1066, or alternatively, when the second elongate member 1066 is retracted over the first elongate member 1064. The filter-like mesh 1060 (or slotted tube 1072) then expands so that the membrane 1062 forms a seal with the surrounding vessel 1068. A guidewire tip 1070 aids in guiding the device through the vessel 1068. The filter-like mesh 1060 and slotted tube 1072 are of a suitable shape memory material such as Nitinol or (304 or 400) stainless steel. The filter-like mesh 1060 is fibrous in nature, being somewhat analogous to steel wool. The slotted tube 1072 has a lattice-like appearance. The slotted tube 1072 may be constructed, for example, by irradiating a thin-walled tube with a laser beam to form holes in the tube in the shape of polygons such as oblong quadrilaterals. An unexpanded, slotted tube 1074 is shown in FIG. 42.

Figure 43:
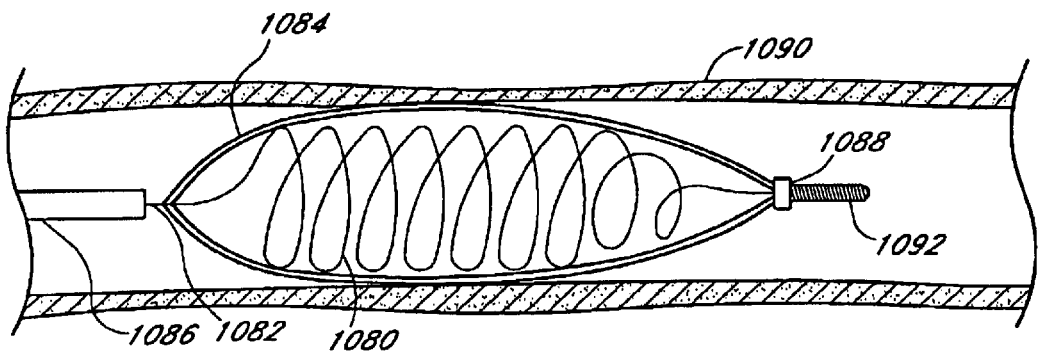
FIG. 43 is a schematic, longitudinal cross sectional view of an embodiment in which a coil is used as the expansion member, and the proximal end of a membrane surrounding the coil adjoins the coil.

FIG. 43 illustrates another embodiment, in which a coil 1080 serves as the self-expanding mechanism. The coil 1080 may be integrally formed with a first elongate member 1082 or be otherwise specially joined to it, e.g., by welding or brazing the coil to the elongate member 1082. The coil 1080 is surrounded by a membrane 1084 that expands with the coil when it is pushed out of a second elongate member 1086, or alternatively, when the second elongate member 1086 is retracted from the coil 1080. Thus, the membrane forms a seal with the surrounding vessel 1090. The membrane 1084 may be attached directly to the first elongate member 1082, or to a member 1088 such as a disk that is in turn secured to the coil 1080 or the first elongate member 1082. A guidewire tip 1092 for guiding the device through the vessel 1090 may be attached to the first elongate member 1082 or to the member 1088, if one is used.

Figure 44:
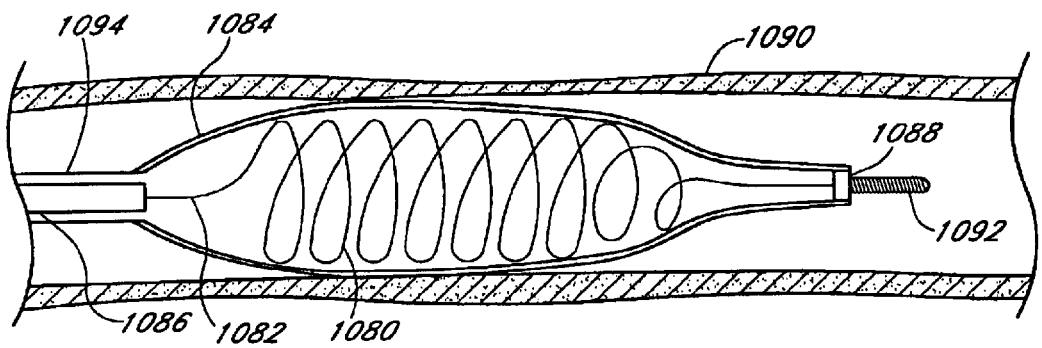
FIG. 44 is a schematic, longitudinal cross sectional view of an embodiment in which a coil is used as the expansion member, and the proximal end of a membrane surrounding the coil adjoins a sheath that surrounds both first and second elongate members.

An embodiment similar to that shown in FIG. 43 is illustrated in FIG. 44, in which the membrane 1084 is secured at the proximal end to a separate sheath 1094. In this case, the sheath 1094 and the first elongate member 1082 are extended together over and through, respectively, the second elongate member 1086. Assembly may require preloading the coil 1080 through the distal end of the second elongate member 1086.

Figure 45:
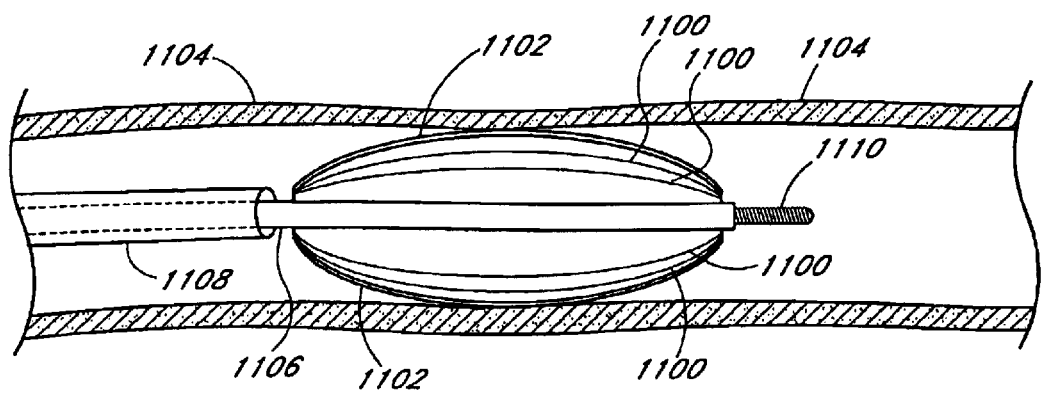
FIG. 45 is a schematic, side cross sectional view of an embodiment in which a plurality of ribbons are used as the expansion member.

Another embodiment that employs a self-expanding medium is shown in FIG. 45, in which a plurality of ribbons 1100 make contact with a membrane 1102 while they expand to urge the membrane towards the wall of the vessel 1104 where it makes a seal. The ribbons 1100 of this embodiment are preferably secured to a first elongate member 1106 at both ends of the ribbons, by, for example, gluing them in place. The ribbons may be 0.001–0.004"× 0.005–0.020"×0.25–1.0" strips of Nitinol, stainless steel, or Elgiloy™ which expand when urged out of the second elongate member 1108. A guidewire tip 1110 may be used for guiding the device through the vessel and is preferably secured to the distal end of the first elongate member 1106.

Figure 46:
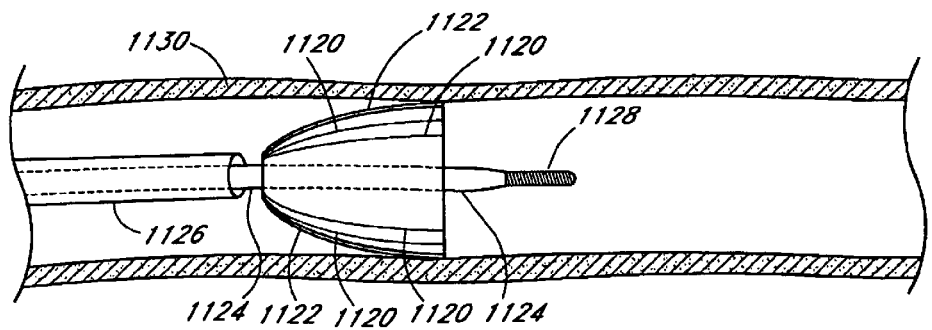
FIG. 46 is a schematic, side cross sectional view of an embodiment in which a plurality of ribs are used as the expansion member.

FIG. 46 illustrates an embodiment similar to the one in FIG. 45, in which ribs 1120 such as wires form a series of semicircular arcs when they expand. The ribs 1120 are surrounded by a membrane 1122 that expands with the ribs to form a seal with the vessel 1124. The number of ribs 1120 is preferably at least three. The ribs 1120 are preferably attached directly to a first elongate member 1124 that is surrounded by a second elongate member 1126. The ribs 1120 themselves are preferably made of a shape memory material such as Nitinol or stainless steel. A guidewire tip 1128 aids in guiding the device through the vessel 1130.

As in the other self-expanding embodiments, the self-expanding mechanism 1100 (1120) is in an unexpanded state when enclosed by the second elongate member 1108 (1126), and expands when pushed or pulled beyond the second elongate member 1108 (1126).

C. Non-self-expanding embodiments

1. Heat Activated Embodiments

Figure 44A:
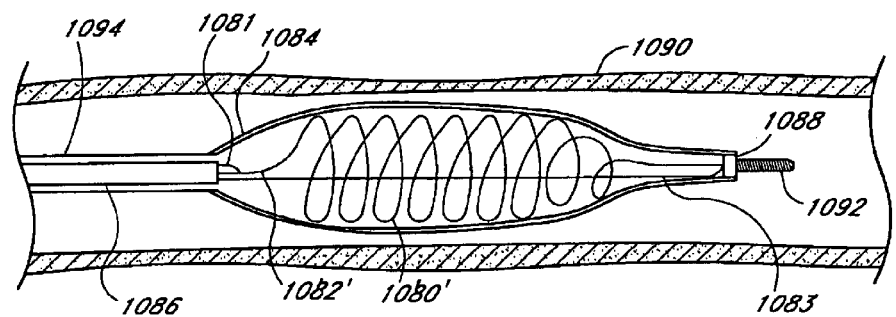
FIG. 44A is an embodiment similar to that shown in FIG. 44 in which resistive heating is used to expand the expansion member, with current being conducted through wires being attached to either side of the expansion member. The expansion member as shown is partially deployed.
Figure 44B:
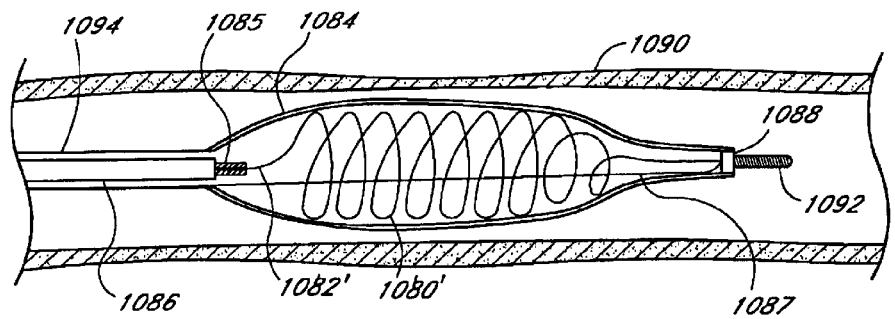
FIG. 44B is an embodiment similar to that shown in FIG. 44A in which resistive heating is used to expand the expansion member, with current being conducted through a wire being attached to the distal end of the expansion member and through a coating on the first elongate member. The expansion member as shown is partially deployed.

FIGS. 44A and 44B illustrate how electrical means can be used to generate heat to expand an expansion member. A first elongate member 1082' (and a coil 1080' which adjoins it, coil 1080' and member 1082' being similar to their unprimed counterparts) is preferably made of heat activated Nitinol, an iron base shape memory alloy, or another material that expands when exposed to heat. As shown in FIG. 44A, low profile, low resistivity electrical lines 1081 and 1083 preferably pass either through or along the second elongate member 86 and are attached (e.g., soldered) to the first elongate member 1082' on either side of the coil 1080'. When current is applied through the electrical lines 1081 and 1083 (the power supply is not shown but is preferably outside the patient), the coil 1080' heats up through resistive heating, and the coil expands to urge the membrane 1084 to contact the vessel wall 1090. Alternatively, as shown in FIG. 44B, the first elongate member 1082' may have a coating 1085 of gold or silver. In this embodiment, the coated elongate member 1082' is used to pass current (with most of the current preferably being carried by the coating 1085, so that most of the energy is deposited in the coil 1080'), with the circuit being completed with a low resistivity wire 1087 that is preferably connected (e.g., soldered) to either the second elongate member 1086 or the sheath 1094. This principle of resistive heating to expand a expansion member can be applied to the other embodiments disclosed herein as well.

Figure 45A:
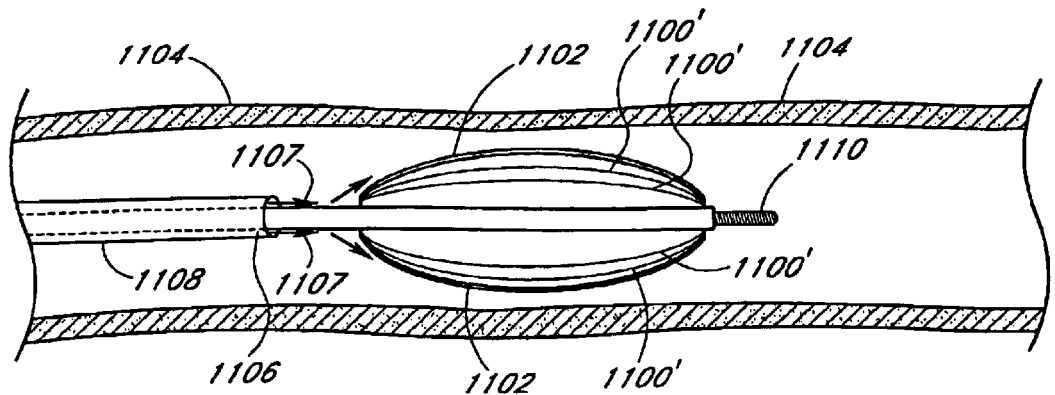
FIG. 45A is an embodiment similar to that shown in FIG. 45 in which a warm solution passes between the first and second elongate members to transfer heat to the expansion member, causing it to expand. The expansion member as shown is partially deployed.
Figure 45B:
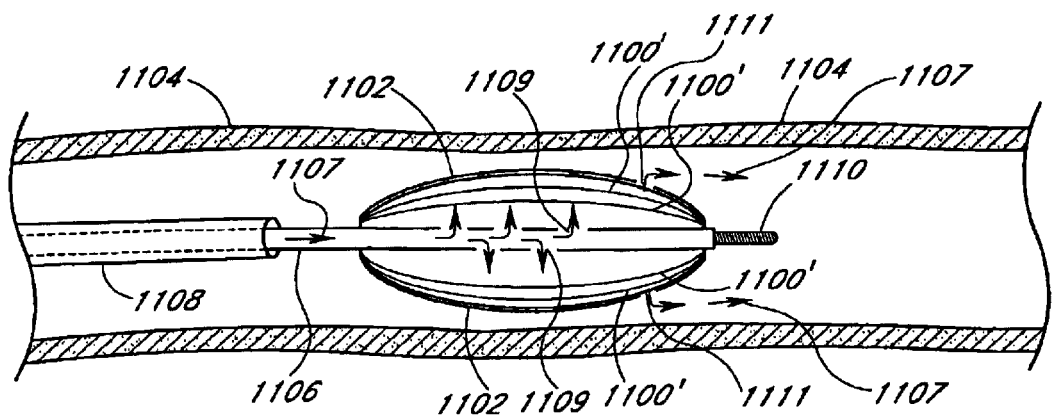
FIG. 45B is an embodiment similar to that shown in FIG. 45A in which a warm solution passes through the first elongate member to transfer heat to the expansion member, causing it to expand. The expansion member as shown is partially deployed.
Figure 45C:
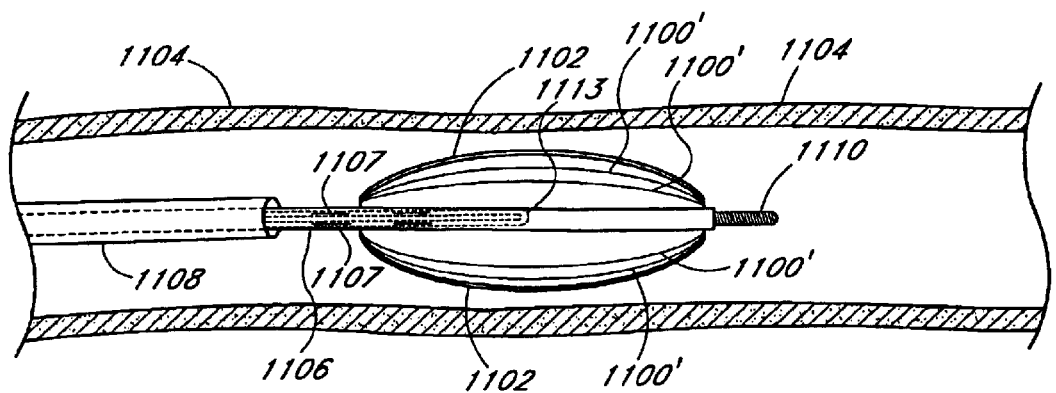
FIG. 45C is an embodiment similar to that shown in FIGS. 45A and 45B, in which a warm solution passes through one or more lumens in the first elongate member to transfer heat to the expansion member, causing it to expand. The expansion member as shown is partially deployed.

FIGS. 45A, 45B and 45C illustrate how heat transfer using a liquid can deploy an expansion member. The ribbons 1100' are preferably made of heat activated Nitinol, an iron base shape memory alloy, or another material that expands when exposed to heat. In the embodiment of FIG. 45A, a warm saline solution 1107 is passed between the first and second elongate members 1106 and 1108 and then over the membrane 1102, so that heat is transferred to the ribbons 1100'. As the ribbons 1100' heat up, they expand, thereby urging the membrane 1102 against the vessel wall 1104. As illustrated in FIG. 45B, the warm saline solution 1107 may also be passed through the first elongate member 1106 and then through holes 1109 in member 1106 so that the saline solution 1107 more directly transfers heat to the ribbons 1100'. In this embodiment, one or more holes 1111 in the membrane 1102 (distal to where the seal with the vessel wall 1104 is made) may be used to allow the saline solution 1107 to flow away beyond the ribbons 1100' after heat transfer to the ribbons occurs. As illustrated in FIG. 45C, the saline solution 1107 may also be passed through one or more closed loop coils or lumens 1113 within the first elongate member 1106. In this way, the ribbons 1100' and the patient's blood are not exposed directly to any solution. Using heat transfer can also be applied to the other embodiments disclosed herein, provided the expansion member is suitably constructed.

2. Mechanically Deployed Embodiments

Other non-self-expanding sealing mechanisms that can be used for occluding a vessel are described below. In the embodiment of FIGS. 47–49, a first elongate member 1140, preferably a pull wire, is (when the device is completely assembled) attached to a brace member 1144 that is in turn attached to a first ring member 1148. Adjoining the first ring member 1148 and a second ring member 1152 are a plurality of ribbons 1156 that extend between the two ring members. Surrounding the ribbons 1156 is a membrane 1160 that forms a seal with the patient's vessel 1162 when the ribbons are expanded. The membrane 1160 is joined to at least one and preferably both of the ring members 1148 and 1152. The membrane 1160 can be joined to only one of the ring members 1148 and 1152, for example, when the membrane 1160 extends far enough in the longitudinal direction to permit the membrane to make a good seal with the vessel 1162 when the ribbons 1156 are deployed.

To assemble the device, the first and second ring members 1148 and 1152, the ribbons 1156, and the membrane 1160 are placed as a unit around a second elongate member 1166, which has a pair of oppositely facing holes 1170 and 1172. The brace member 1144 is inserted through the holes 1170 and 1172 and secured to both the pull wire 1140 and the first ring member 1148. Further, the second ring member 1152 is secured to the second elongate member 1166. This assembled configuration, with the ribbons 1156 in their longitudinal orientation, is illustrated in FIG. 48. As illustrated in FIG. 49, when the pull wire 1140 is retracted, the ribbons 1156 (shown in phantom) and the membrane 1160 that surrounds them are urged towards the vessel 1162, where the membrane makes a seal with the vessel. The ribbons 1160 are preferably resilient enough so that they return to their longitudinal orientation when the pull wire 1140 is released. The elasticity and resilience of the pull wire 1140 also helps the ribbons 1156 return to their undeployed configuration. A guidewire tip 1171 may be used to assist in guiding the device to the desired location in the vessel 1162.

Figure 50A:
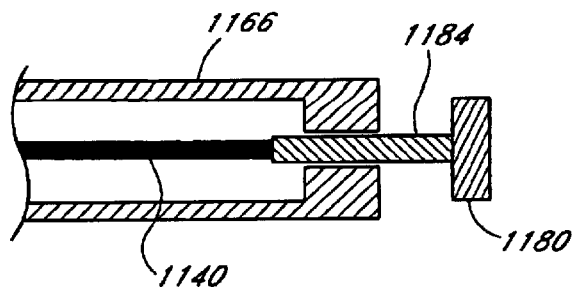
FIGS. 50A and 50B show longitudinal and end perspective views, respectively, of a locking mechanism used with a wire that deploys an expansion member.
Figure 50B:
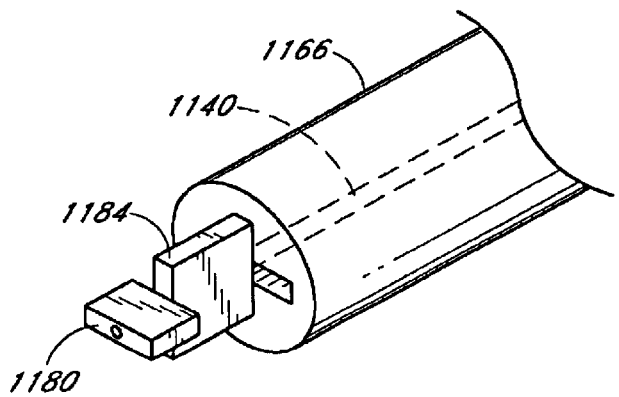

A preferred way of retracting the pull wire 1140 is shown in FIGS. 50A and 50B. FIG. 50A shows the pull wire 1140, which is attached to the brace member 1144. A rotatable handle 1180 is attached to a locking member 1184 which in turn is fastened to the pull wire 1140. When the locking member 1184 clears the second elongate member 1166 within which it resides (which is preferably outside the patient), the locking member and rotatable handle 1180 may be oriented as illustrated in FIG. 50B to keep the pull wire 1140 taught, thereby preventing the sealing mechanism from returning to its undeployed position. The pull wire 1140 may be made of stainless or nitinol and may have a diameter of 0.006–0.008 inches, for a catheter having an O.D. of 0.014", for example.

An alternative to the deployment apparatus illustrated in FIGS. 50A and 50B is shown in FIG. 51A, in which a handle member 1190 is grasped by the clinician to retract the pull wire 1140, thereby deploying the sealing mechanism. Once extended, the sealing mechanism preferably has the tendency to return to its undeployed position, which in the process pulls the pull wire 1140 back into the second elongate member 1166. This can be prevented by inserting a spacer member 1194 between the handle member 190 and the second elongate member 1166. After the medical procedure is complete, and occlusion of the vessel is no longer required, the spacer member 1194 can be removed and the pull wire 1140 and the sealing mechanism returned to their respective undeployed positions. The device can then be removed from the patient.

Figure 50C:
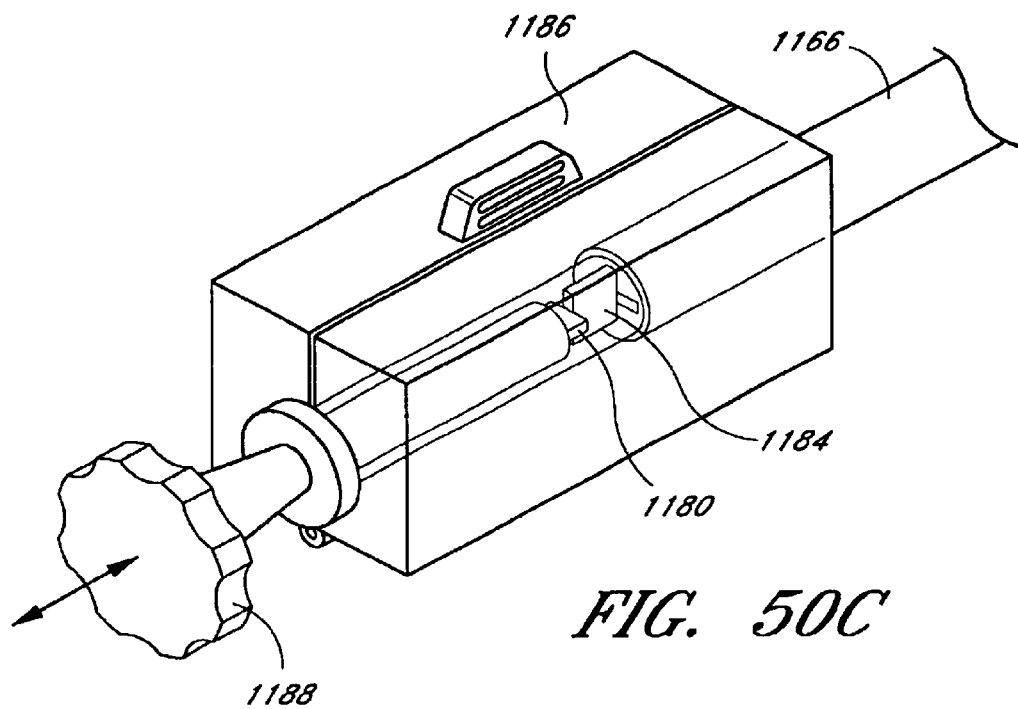
FIG. 50C is a perspective view of the locking mechanism of FIGS. 50A and 50B, further showing an adaptor for utilizing the locking mechanism.
Figure 51B:
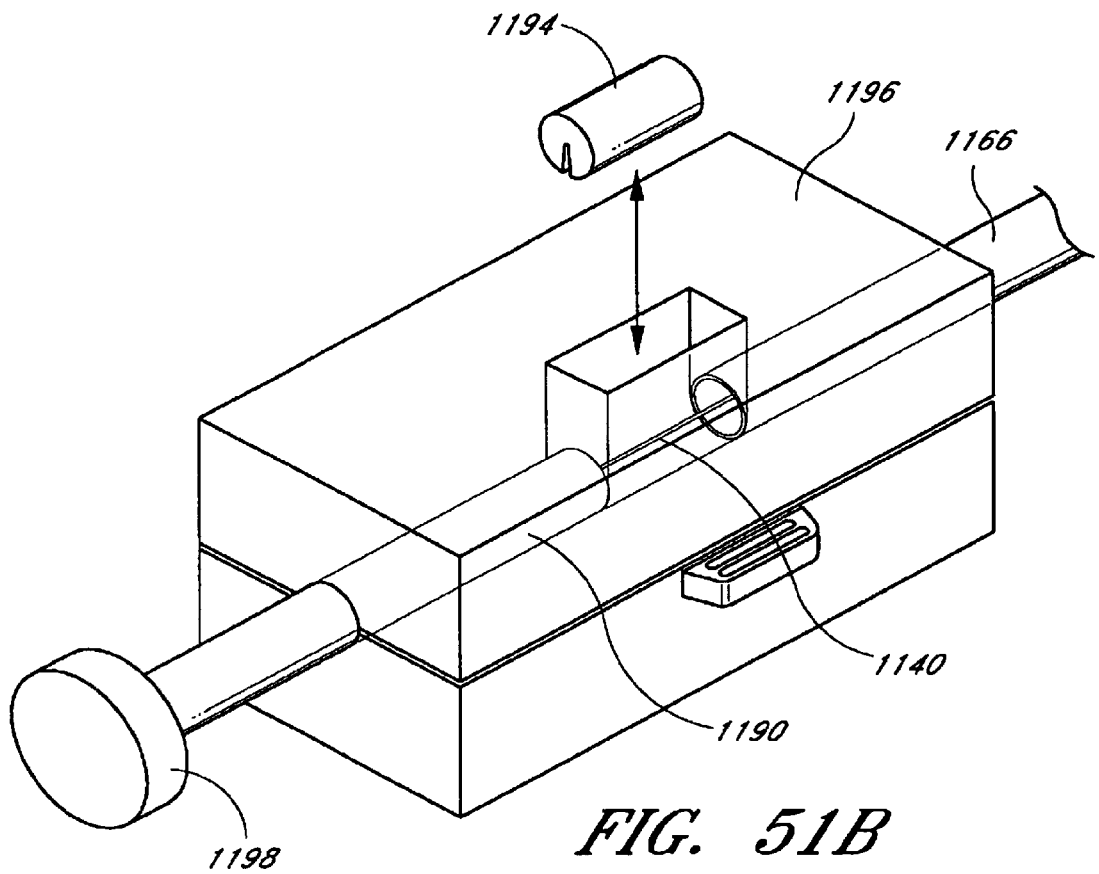
FIG. 51B is a perspective view of the alternative locking mechanism of FIG. 51A, further showing an adaptor for utilizing the locking mechanism.

Both pull wire mechanisms shown in FIGS. 50A and 51A are preferably engaged by use of an adaptor 1186 or 1196, as shown in FIGS. 50C and 51B, respectively. This adaptor 1186 or 1196 allows for easier control of the pull wire mechanism. In FIG. 50C, the knob 1188 is adapted to connect to the rotatable handle 1180 and locking member 1184. By turning and pulling the knob 1188, the pull wire 1140 may be retracted to deploy the sealing mechanism. In FIG. 51B, the handle 1198 can be grasped to pull handle member 1190 away from second elongate member 1166. This opens up a space between members 1190 and 1166 to allow spacer member 1194 to be inserted through a window in adaptor 1196 for holding the pull wire 1140 taut. Once the pull wire mechanism is engaged, the adaptor in both embodiments may be removed to allow for an exchange over the proximal end of the pull wire devices.

Although the principle of using a non-self-expanding mechanism has been illustrated in FIGS. 47–49 with respect to deformable ribbons, other non-self-expanding mechanisms, as illustrated in FIGS. 52A–52D, can be employed in conjunction with the brace member 1144 and the first and second ring members 1148 and 1152. For example, instead of using ribbons 1156, a non-self-expanding braided structure 1200 can be used, in which the braided structure 1200 adjoins first and second ring members 1148 and 1152 and is covered with a membrane 1160 to form the unit 1204 shown in FIG. 52A. The unit 1204 can be used in conjunction with an elongate member 1166, a brace member 1144, a guidewire tip 1171, a first elongate member 1140 such as a pull wire, a rotatable handle 1180, and a locking member 1184 to form a device analogous to the ribbon-based device of FIG. 47. Alternatively, other mechanisms can be used for securing the pull wire 1140, such as a handle member 1190 and a spacer member 1194.

Figure 52A:
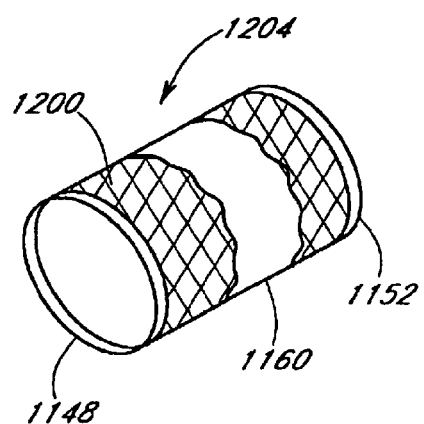
FIGS. 52A, 52B, 52C, and 52D show, respectively, a braid, a filter-like mesh, a slotted tube, and a plurality of coils, which can be used as alternative expansion members in place of the ribbons in the embodiment of FIG. 47.
Figure 52B:
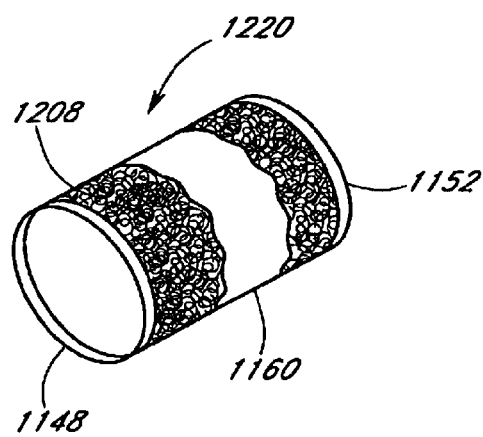
Figure 52C:
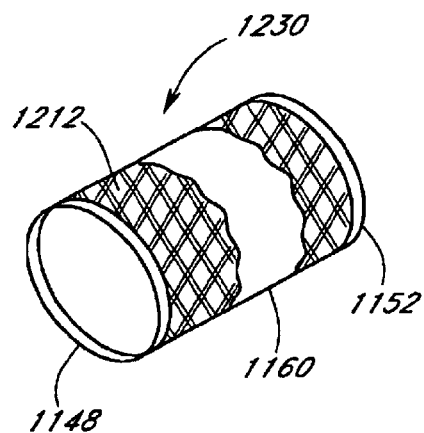
Figure 52D:
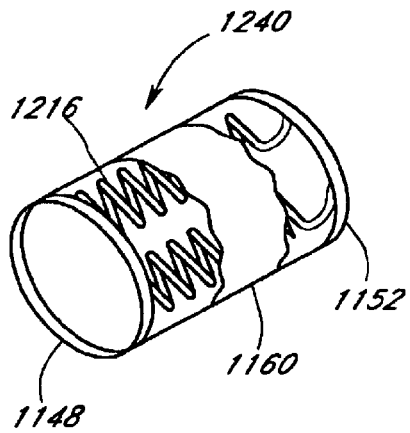

Other non-self-expanding mechanisms such as a filter-like mesh 1208, a slotted tube 1212, and coils 1216 can be used to form units 1220, 1230, and 1240 analogous to the braided structure unit 1204 as shown in FIGS. 52B, 52C and 52D. Units 1220, 1230, and 1240 can likewise be used to construct devices analogous to the ribbon-based device illustrated in FIGS. 47–51. Further, if unit 1204 is used without a membrane, it may assist in blood perfusion if the braided structure 1200 is suitably constructed. Alternatively, perforated membranes like membranes 1036' of FIG. 38B may be used to permit blood perfusion. Although the ribbons 1156, the braided structure 1200, the filter-like mesh 1208, the slotted tube 1212, and the coils 1216 must be actively deployed (e.g. with a pull wire 1140), they are nevertheless similar to their self-expanding counterparts.

It should be understood that the scope of the present invention is not be limited by the illustrations or the foregoing description thereof, but rather by the appended claims, and certain variations and modifications of this invention will suggest themselves to one of ordinary skill in the art.

What is claimed is:

1. A catheter system for emboli containment, comprising:
   a guidewire having a proximal end and a distal end;
   an occlusive device connected to the distal end of the guidewire, the occlusive device being actuatable between an expanded state in which the occlusive device engages at least a portion of the walls of a blood vessel, and a nonexpanded state in which the occlusive device does not engage the walls of the blood vessel;
   a first treatment catheter having a proximal end and a distal end and a lumen extending therethrough; and
   a second treatment catheter having a proximal end and a distal end and a lumen extending therethrough;
   wherein the first treatment catheter is adapted to be delivered over and then removed from the guidewire, and the second treatment catheter is adapted to be delivered over and then removed from the guidewire following removal of the first treatment catheter, and wherein the occlusive device is capable of maintaining its expanded state while the first treatment catheter is removed from the guidewire and while the second treatment catheter is delivered over the guidewire;
   wherein the occlusive device is a self-expanding sealing member.

2. The catheter system of claim 1, further comprising a sleeve provided over the self-expanding sealing member, wherein removal of the sleeve actuates the self-expanding sealing member.

3. A catheter system for emboli containment, comprising:
   a guidewire having a proximal end, a distal end, and a lumen extending therethrough;
   an occlusive device connected to the distal end of the guidewire, the occlusive device being actuatable between an expanded state in which the occlusive device engages at least a portion of the walls of a blood vessel, and a nonexpanded state in which the occlusive device does not engage the walls of the blood vessel;
   a first treatment catheter having a proximal end and a distal end and a lumen extending therethrough; and
   a second treatment catheter having a proximal end and a distal end and a lumen extending therethrough;
   wherein the first treatment catheter is adapted to be delivered over and then removed from the guidewire, and the second treatment catheter is adapted to be delivered over and then removed from the guidewire following removal of the first treatment catheter, and wherein the occlusive device is capable of maintaining its expanded state while the first treatment catheter is removed from the guidewire and while the second treatment catheter is delivered over the guidewire;
   wherein the occlusive device is actuated by a pull wire extending through the lumen of the guidewire.

4. The catheter system of claim 3, wherein the occlusive device is a filter.

5. The catheter system of claim 4, wherein the first treatment catheter is a therapy catheter.

6. The catheter system of claim 5, wherein the second treatment catheter is an aspiration catheter.

7. The catheter system of claim 4, wherein the second treatment catheter is a therapy catheter.

8. The catheter system of claim 4, wherein the second treatment catheter is an aspiration catheter.

9. The catheter system of claim 4, further comprising a third treatment catheter having a proximal end and a distal end and a lumen extending therethrough, wherein the third treatment catheter is adapted to be delivered over and then removed from the guidewire following removal of the first treatment catheter and prior to delivery of the second treatment catheter.

10. The catheter system of claim 9, wherein the first treatment catheter has a dilatation balloon of a first diameter on its distal end, the third treatment catheter has a dilatation balloon of a second diameter on its distal end, the second diameter being larger than the first diameter, and the second treatment catheter is an aspiration catheter.

11. The catheter system of claim 4, wherein the guidewire includes a lumen extending therethrough.

12. A catheter system for emboli containment, comprising:
    a guidewire having a proximal end and a distal end;
    an occlusive device connected to the distal end of the guidewire, the occlusive device being actuatable between an expanded state in which the occlusive device engages at least a portion of the walls of a blood vessel, and a nonexpanded state in which the occlusive device does not engage the walls of the blood vessel; and a catheter having a proximal end and a distal end and a lumen extending therethrough, the catheter being adapted to be delivered over and removed from the guidewire;

wherein the occlusive device is capable of maintaining its expanded state while the catheter is either advanced over or removed from the guidewire;

wherein the occlusive device is a self-expanding sealing member.

13. The catheter system of claim 12, further comprising a sleeve provided over the self-expanding sealing member, wherein removal of the sleeve actuates the self-expanding sealing member.

14. A catheter system for emboli containment, comprising:

a guidewire having a proximal end, a distal end, and a lumen extending therethrough;

an occlusive device connected to the distal end of the guidewire, the occlusive device being actuatable between an expanded state in which the occlusive device engages at least a portion of the walls of a blood vessel, and a nonexpanded state in which the occlusive device does not engage the walls of the blood vessel; and a catheter having a proximal end and a distal end and a lumen extending therethrough, the catheter being adapted to be delivered over and removed from the guidewire;

wherein the occlusive device is capable of maintaining its expanded state while the catheter is either advanced over or removed from the guidewire;

wherein the occlusive device is actuated by a pull wire extending through the lumen of the guidewire.

15. The catheter system of claim 14, wherein the occlusive device is a filter.

* * * * *